United States Patent [19]
Maes et al.

[11] Patent Number: 6,010,703
[45] Date of Patent: Jan. 4, 2000

[54] RECOMBINANT POXVIRUS VACCINE AGAINST FELINE RHINOTRACHEITIS

[75] Inventors: Roger K. Maes, Okemos; Stephen J. Spatz, Lansing, both of Mich.

[73] Assignee: Board of Trustees operating Michigan State University, East Lansing, Mich.

[21] Appl. No.: 08/911,321

[22] Filed: Aug. 14, 1997

Related U.S. Application Data

[63] Continuation of application No. 08/096,183, Jul. 26, 1993, abandoned.

[51] Int. Cl.$^7$ ..................... A61K 39/295; A61K 39/275; A61K 39/245; C12N 7/01
[52] U.S. Cl. .................................. 424/199.1; 424/229.1; 424/232.1; 435/235.1; 435/320.1
[58] Field of Search .............................. 424/199.1, 229.1, 424/232.1; 435/69.3, 235.1, 320.1; 935/65

[56] References Cited

U.S. PATENT DOCUMENTS

| | | | |
|---|---|---|---|
| 5,338,683 | 8/1994 | Paoletti | 435/320.1 |
| 5,494,807 | 2/1996 | Paoletti et al. | 435/69.3 |

OTHER PUBLICATIONS

Blacklaws, B.A., et al., Virology 177:727–736 (1990).
Maes, R.K., et al., J. Virol. 51:259–262 (1984).
Burgener, D.C. and R.K.Maes, American J. Vet. Res. 49:1673–1676 (1988).
Rota, P.A., et al., Virology 154:168–179 (1986).
Spear, P.G., Glycoproteins specified by herpes simples viruses.In"The Herpesviruses" (B. Roizman, ED.) vol. 3 pp. 315–356. Plenum, New York (1984).
Hutchinson, L., et al., J. Virol. 66, 2240–2250 (1992).
MacLean,C., et al., J. Gen. Virol. 72, 897–906 (1991).
Kyte, J. ad Doolittle, R., J. of Molecular Biology 157, 105–131 (1982).
Birnstiel,J., Busslinger, M. and Strub, K., Cell 41, 349–358 (1985).
Talens, L.T. and Y. Zee, Proc. Soc. Exp. Biol. Med. 151, 132–135 (1976).
Ausubel, F.,, et al., Current Protocols in Molecular Biology, J. Wiley & Sons, New York, pp. 1.7.1–1.7–2; 1.15.2–1.15.3; 4.2.1–4.2.3; and 10.8.1–10.8.6 (1988).
Sambrook, J., et al., Molecular Cloning: A Laboratory Manual. vol. II Cold Spring Harbor, N.Y.: Cold Spring Harbor Laboratory (1989).
Sanger,F., Nicklen, S. and Coulson, A., Proceedings of the National Academy of Science,U.S.A. 74, 5463–5467 (1977).
Chou,P. and Fasman, G., Empirical Predictions of protein conformation. Annual Review of Biochemistry 47, 251–275 (1978).
Hammerschmidt,W., et al., Virology 165, 406–418 (1988).
Robbins, A.K., et al., J. Virol. 61, 2691–2701 (1987.
Gidoni, D., et al., Nature 12, 409–413 (1984).
Pederson,N., et al., J. Virol. 65 ,3746–3758 (1991).
Addison, C., et al., J. Gen Virol. 71, 2377–2384 (1990).

Horimoto, T., et al., Jpn. J. Vet. Sci. 51, 607–612 (1989).
Fuller and Spear, J. of Virology 55:475–482 (1985).
Spear et al., Herpes simplex virus:pathway of entry into cells. In "Cell Biology of Virus Entry, Replication and Pathogenesis" pp. 163–175 (1989).
Johnson et al., J. of Virology 64: 2569–2576 (1990).
Davison, A., Virology 186:9–14 (1992).
Noble, A., et al., Virology 129:218–224 (1983).
Johnson, D., et al., J. of Virology 62:4605–4612 (1988).
Marchioli, C., et al., J. of Virology 61: 3977–3982 (1987).
Para, M., et al., J. of Virology 55:483–487 (1985).
Iglesias, G., et al., Vet. Micro. 24: 1–10 (1990).
Britt, W., et al., J. of Virology 64: 1079–1085 (1990).
Long, D., et al., Infection and Immunity 37: 761–763 (1984).
Eisenberg, R., et al., J. of Virology 56:1014–1017 (1985).
Eloit, M.,et al., J. of Gen Virology 71: 2425–2431 (1990).
Riviere, M., et al., J. of Virology 66: 3424–3433 (1992).
van Drunen littel–van den Hurk, S., et al., J. of Gen. Virology 71:2053–2063 (1990).
Petrovskis, E., et al., J. of Virology 59: 216–223 (1986).
Ghiasi, H., et al., Arch Virology 121: 163–177 (1991).
Bernstein, D., et al., J. of Immunology 146: 3571–3577 (1991).
Rooney, J., et al., J. of Virology 62:1530–1534 (1988).
Wachsman, M., et al., J. Gen. Virology 70:2513–2520 (1989).
Wachsman, M., et al., J. of Inf. Dis. 159: 625–634 (1989).
Nakagama, H., et al., FASEB J. 5:104–108 (1991).
Zarling, J., et al., J. of Immunology 136: 4669–4673 (1986).
Reddy, P., et al., Vet. Immuno. Immunopath. 23: 62–74 (1989).
Hughes, H., et al., Immunology 74:461–466 (1991).
Hinuma, S., et al., FEBS 288,138–142 (1991).
Devereaux, J., and Grinyer, I., Nucleic Acid Research 12: 387–395 (1984).
Felsenstein, J., Evolution 39:783–791 (1985).
McGeoch, D., et al., J. Mol. Biol. 181:1–13 1985).
McGeoch, D., et al., J. Gen. Virology 69: 1531–1551 (1988).
Scott, F., Racoon poxvirus in the cat—candidate carrier virus for recombinant vaccines. In: the proceedings of the 69th conference of research workers in animal disease. Chicago,I. (1988).
Audonnet, J.C. et al. 1990. Journal of General Virology, vol.71, p. 2969–2978.
Flowers, C.C. et al. 1992. Virology, vol. 190, p. 307–315.
Petrovskis, E.A. et al. 1986. Journal of Virology, vol. 59, p. 216–223.
Ross, L.J.N. et al. 1991. Journal of General Virology, vol. 72, p. 939–947, 949–954.

(List continued on next page.)

*Primary Examiner*—Mary E. Mosher
*Attorney, Agent, or Firm*—Ian C. McLeod

[57] ABSTRACT

A recombinant poxvirus vaccine against feline herpesvirus (FHV-1) is described. The recombinant poxviruses include synthetic genes encoding either a gB or gD precursor polypeptide or mixtures of the two recombinant poxviruses. The vaccine is used to provide immunity to FHV-1 in cats.

15 Claims, 24 Drawing Sheets

OTHER PUBLICATIONS

Tikoo, S.K. et al. 1990. Journal of Virology, vol. 64, p. 5132–5142.

Riviere, M. et al. Journal of Virology, vol. 66, p. 3424–3434, 1992.

van Drunen Littel–van den Hurk, S. et al, Vaccine, vol. 11, p. 25–35, 1993.

Aurelian, L. et al. Reviews of Infectious Diseases, vol. 13, Suppl. 1, p. S924–S934, 1991.

Spatz et al , Journal of General Virology 57:1235–1244, 1994.

Esposito and Murphy. Advances in Veterinary Science and Comparative Medicine, vol. 33, Vaccine Biotechnology, p. 195–247, "infectious Recombinant Vectored Virus Vaccines", 1989.

Esposito, J.J et al. Virology 165: 313–316 (1988).

Maeda, K et al. Arch. Virol. 127: 387–397 (1992).

Lodmell, D et al. J. Virol. 65(6): 3400–3405 (1991).

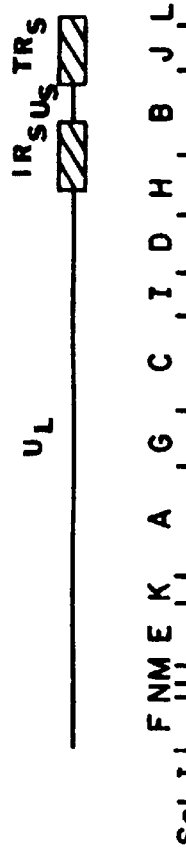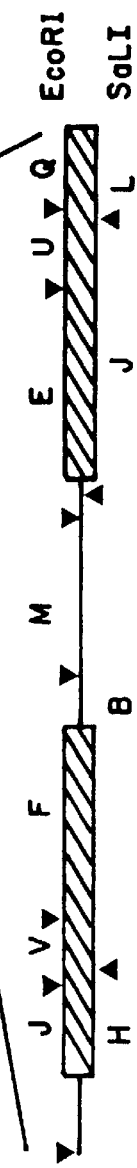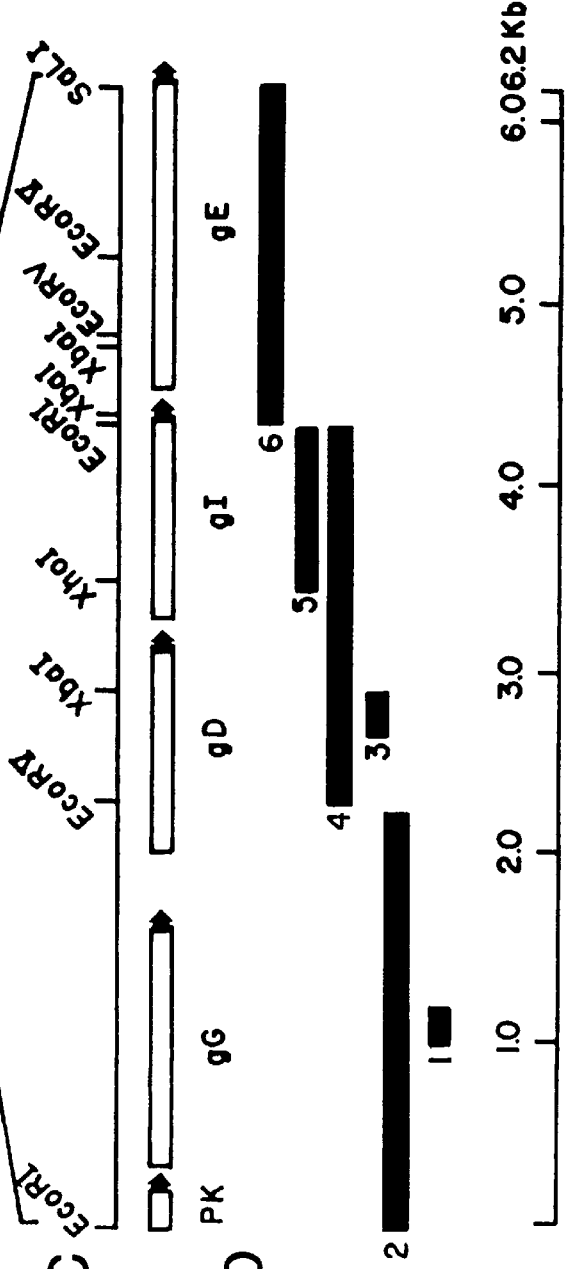
FIG. 8A
FIG. 8B
FIG. 8C
FIG. 8D

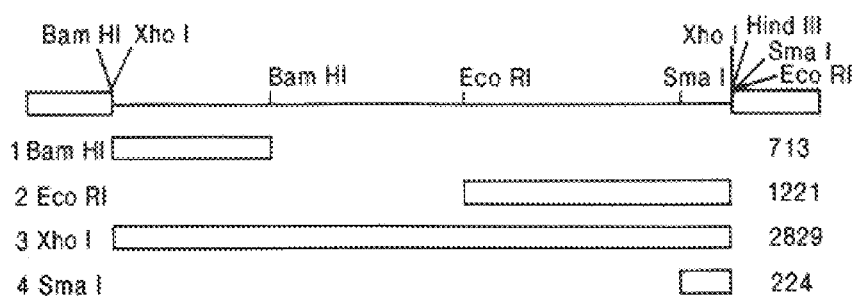
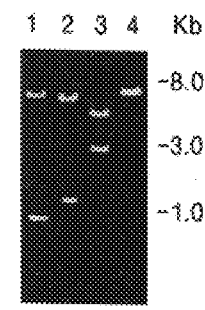
FIG. 16A
FIG. 16C
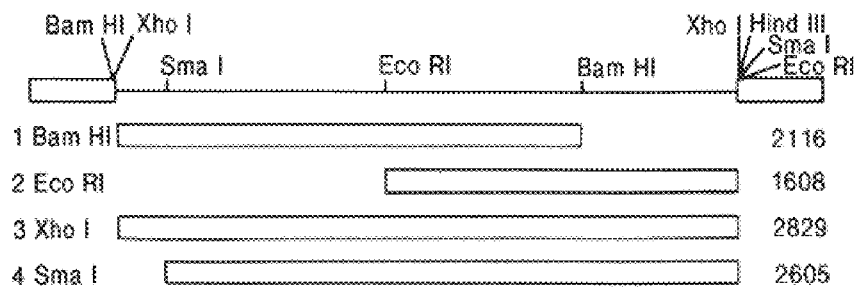
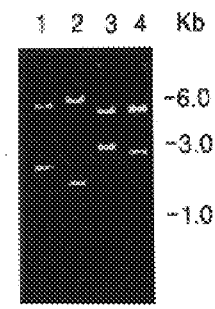
FIG. 16B
FIG. 16D

```
                              SEQUENCE LISTING (1) GENERAL INFORMATION:

(iii) NUMBER OF SEQUENCES:  11

(2) INFORMATION FOR SEQ ID NO:1:

(i) SEQUENCE CHARACTERISTICS:
          (A) LENGTH: 2829
          (B) TYPE:  Nucleic Acid
          (C) STRANDEDNESS: Double
          (D) TOPOLOGY:  Linear (ii) MOLECULE TYPE:
          (A) DESCRIPTION: DNA (iii) HYPOTHETICAL:  No (iv) ANTI-SENSE:  No (vi) ORIGINAL SOURCE:
          (A) ORGANISM:  Feline herpesvirus-1
          (B) STRAIN:  1
          (C) INDIVIDUAL ISOLATE:  C-27
          (G) CELL TYPE:  N/A (ix) FEATURE:
          (A) NAME/KEY:
          (B) LOCATION:
          (C) IDENTIFICATION METHOD:  Sequencing
          (D) OTHER INFORMATION:  DNA and deduced
               polypeptide (xi) SEQUENCE DESCRIPTION: SEQ ID NO:1:

ATG TCC ACT CGT GGC GAT CTT GGG AAG CGG CGA CGA GGG AGT CGT TGG        48
Met Ser Thr Arg Gly Asp Leu Gly Lys Arg Arg Arg Gly Ser Arg Trp
                  5                  10                  15

CAG GGA CAC AGT GGC TAT TTT CGA CAG AGA TGT TTT TTC CCT TCT CTA        96
Gln Gly His Ser Gly Tyr Phe Arg Gln Arg Cys Phe Phe Pro Ser Leu
```

-continued

```
            20                  25                  30
CTC GGT ATT GCA GCG ACT GGC TCC AGA CAT GGT AAC GGA TCG TCG GGA      144
Leu Gly Ile Ala Ala Thr Gly Ser Arg His Gly Asn Gly Ser Ser Gly
            35                  40                  45

TTA ACC AGA CTA GCT AGA TAT GTT TCA TTT ATC TGG ATC GTA CTA TTC      192
Leu Thr Arg Leu Ala Arg Tyr Val Ser Phe Ile Trp Ile Val Leu Phe
        50                  55                  60

TTA GTC GGT CCC CGT CCA GTA GAG GGT CAA TCT GGA AGC ACA TCG GAA      240
Leu Val Gly Pro Arg Pro Val Glu Gly Gln Ser Gly Ser Thr Ser Glu
65                  70                  75                  80

CAA CCC CGG CGG ACT GTA GCT ACC CCT GAG GTA GGG GTA CAC CAC CAA      288
Gln Pro Arg Arg Thr Val Ala Thr Pro Glu Val Gly Val His His Gln
                85                  90                  95

AAC CAA CTA CAG ATC CCA CCG ATA TGT CGA TAT GAG GAA GCT CTC CGT      336
Asn Gln Leu Gln Ile Pro Pro Ile Cys Arg Tyr Glu Glu Ala Leu Arg
            100                 105                 110

GCG TCC CAA ATA GAG GCT AAC GGA CCA TCG ACT TTT TAT ATG TGT CCA      384
Ala Ser Gln Ile Glu Ala Asn Gly Pro Ser Thr Phe Tyr Met Cys Pro
        115                 120                 125

CCA CCT TCA GGA TCT ACT GTC GTG CGT TTA GAG CCA CCA CGG GCC TGT      432
Pro Pro Ser Gly Ser Thr Val Val Arg Leu Glu Pro Pro Arg Ala Cys
130                 135                 140

CCA GAT TAT AAA CTA GGG AAA AAT TTT ACC GAG GGT ATA GCT GTA ATA      480
Pro Asp Tyr Lys Leu Gly Lys Asn Phe Thr Glu Gly Ile Ala Val Ile
145                 150                 155                 160

TTT AAA GAA AAT ATA GCG CCA TAT AAA TTC AAG GCA AAT ATA TAC TAT      528
Phe Lys Glu Asn Ile Ala Pro Tyr Lys Phe Lys Ala Asn Ile Tyr Tyr
                165                 170                 175

AAA AAC ATT ATT ATG ACA ACG GTA TGG TCT GGG AGT TCC TAT GCC GTT      576
Lys Asn Ile Ile Met Thr Thr Val Trp Ser Gly Ser Ser Tyr Ala Val
            180                 185                 190

ACA ACC AAC CGA TAT ACA GAC AGG GTT CCC GTG AAA GTT CAA GAG ATT      624
Thr Thr Asn Arg Tyr Thr Asp Arg Val Pro Val Lys Val Gln Glu Ile
        195                 200                 205

ACA GAT CTC ATA GAT AGA CGG GGT ATG TGC CTC TCG AAA GCT GAT TAC      672
Thr Asp Leu Ile Asp Arg Arg Gly Met Cys Leu Ser Lys Ala Asp Tyr
210                 215                 220

GTT CGT AAC AAT TAT CAA TTT ACG GCC TTT GAT CGA GAC GAG GAT CCC      720
Val Arg Asn Asn Tyr Gln Phe Thr Ala Phe Asp Arg Asp Glu Asp Pro
225                 230                 235                 240

AGA GAA CTG CCT CTG AAA CCT CCA AGT TCA ACA CTC TCC AGA GTC CGT      768
Arg Glu Leu Pro Leu Lys Pro Pro Ser Ser Thr Leu Ser Arg Val Arg
                245                 250                 255

GGA TGG CAC ACC AAT GAA ACA TAC ACA AAG ATC GTG CTG CTG GAT TTC      816
Gly Trp His Thr Asn Glu Thr Tyr Thr Lys Ile Val Leu Leu Asp Phe
            260                 265                 270

CAC CAC TCT GGG ACC TCT GTA AAT TGC ATC GTA GAG GAA GTG GAT GCA      864
His His Ser Gly Thr Ser Val Asn Cys Ile Val Glu Glu Val Asp Ala
        275                 280                 285

AGA TCT GTA TAT CCA TAT GAC TCA TTT GCT ATC TCC ACT GGT GAC GTG      912
Arg Ser Val Tyr Pro Tyr Asp Ser Phe Ala Ile Ser Thr Gly Asp Val
290                 295                 300

ATT CAC ATG TCT CCA TTC TTT GGG CTG AGG GAT GGA GCC CAT GTA GAA      960
Ile His Met Ser Pro Phe Phe Gly Leu Arg Asp Gly Ala His Val Glu
305                 310                 315                 320

CAT ACT AGT TAT TCT TCA GAC AGA TTT CAA CAA ATC GAG GGA TAC TAT     1008
His Thr Ser Tyr Ser Ser Asp Arg Phe Gln Gln Ile Glu Gly Tyr Tyr
                325                 330                 335

CCA ATA GAC TTG GAT ACC GAT TAC ACT GGG GCA CCA GTT TCT CGC AAT     1056
Pro Ile Asp Leu Asp Thr Asp Tyr Thr Gly Ala Pro Val Ser Arg Asn
```

-continued

```
                  340                    345                   350
TTT TTG GAA ACT CCG CAT GTG ACA GTG GCC TGG AAC TGG ACC CCA AAG        1104
Phe Leu Glu Thr Pro His Val Thr Val Ala Trp Asn Trp Thr Pro Lys
        355                 360                 365

TCT GGT CGG GTA TGT ACC TTA GCC AAA TGG AGG GAA ATA GAT GAA ATG        1152
Ser Gly Arg Val Cys Thr Leu Ala Lys Trp Arg Glu Ile Asp Glu Met
370                 375                 380

CTA CCG ATG AAT ATA GGC TCC TAT AGA TTT ACA GCC AAG ACC ATA TCC        1200
Leu Pro Met Asn Ile Gly Ser Tyr Arg Phe Thr Ala Lys Thr Ile Ser
385                 390                 395                 400

GCT ACT TTC ATC TCC AAT ACT TCA CAA TTT GAA ATC AAT CGT ATC CGT        1248
Ala Thr Phe Ile Ser Asn Thr Ser Gln Phe Glu Ile Asn Arg Ile Arg
                405                 410                 415

TTG GGG GAC TGT GCC ACC AAG GAG GCA GCC GAA GCC ATA GAC CGG ATT        1296
Leu Gly Asp Cys Ala Thr Lys Glu Ala Ala Glu Ala Ile Asp Arg Ile
        420                 425                 430

TAT AAG AGT AAA TAT AGT AAA ACT CAT ATT CAG ACT GGA ACC CTG GAG        1344
Tyr Lys Ser Lys Tyr Ser Lys Thr His Ile Gln Thr Gly Thr Leu Glu
            435                 440                 445

ACC TAC CTA GCC CGT GGG GGA TTT CTA ATA GCT TTC CGT CCC ATG ATC        1392
Thr Tyr Leu Ala Arg Gly Gly Phe Leu Ile Ala Phe Arg Pro Met Ile
450                 455                 460

AGC AAC GAA CTA GCA AAG TTA TAT ATC AAT GAA TTA GCA CGT TCC AAT        1440
Ser Asn Glu Leu Ala Lys Leu Tyr Ile Asn Glu Leu Ala Arg Ser Asn
465                 470                 475                 480

CGC ACG GTA GTG GAT CTC AGT GCA CTC CTC AAT CCA TCT GGG GAA ACA        1488
Arg Thr Val Val Asp Leu Ser Ala Leu Leu Asn Pro Ser Gly Glu Thr
                485                 490                 495

GTA CAA CGA ACT AGA AGA TCG GTC CCA TCT AAT CAA CAT CAT AGG TCG        1536
Val Gln Arg Thr Arg Arg Ser Val Pro Ser Asn Gln His His Arg Ser
        500                 505                 510

CGG CGC AGC ACA ATA GAG GGG GGT ATA GAA ACC GTG AAC AAT GCA TCA        1584
Arg Arg Ser Thr Ile Glu Gly Gly Ile Glu Thr Val Asn Asn Ala Ser
            515                 520                 525

CTC CTC AAG ACC ACC TCA TCT GTG GAA TTC GCA ATG CTA CAA TTT GCC        1632
Leu Leu Lys Thr Thr Ser Ser Val Glu Phe Ala Met Leu Gln Phe Ala
        530                 535                 540

TAT GAC TAC ATA CAA GCC CAT GTA AAT GAA ATG TTG AGT CGG ATA GCC        1680
Tyr Asp Tyr Ile Gln Ala His Val Asn Glu Met Leu Ser Arg Ile Ala
545                 550                 555                 560

ACT GCC TGG TGT ACA CTT CAG AAC CGC GAA CAT GTG CTG TGG ACA GAG        1728
Thr Ala Trp Cys Thr Leu Gln Asn Arg Glu His Val Leu Trp Thr Glu
                565                 570                 575

ACC CTA AAA CTC AAT CCC GGT GGG GTG GTC TCG ATG GCC CTA GAA CGT        1776
Thr Leu Lys Leu Asn Pro Gly Gly Val Val Ser Met Ala Leu Glu Arg
        580                 585                 590

CGT GTA TCC GCG CGC CTA CTT GGA GAT GCC GTC GCC GTA ACA CAA TGT        1824
Arg Val Ser Ala Arg Leu Leu Gly Asp Ala Val Ala Val Thr Gln Cys
            595                 600                 605

GTT AAC ATT TCT AGC GGA CAT GTC TAT ATC CAA AAT TCT ATG CGG GTG        1872
Val Asn Ile Ser Ser Gly His Val Tyr Ile Gln Asn Ser Met Arg Val
        610                 615                 620

ACG GGT TCA TCA ACG ACA TGT TAC AGC CGC CCT CTT GTT TCC TTC CGT        1920
Thr Gly Ser Ser Thr Thr Cys Tyr Ser Arg Pro Leu Val Ser Phe Arg
625                 630                 635                 640

GCC CTC AAT GAC TCC GAA TAC ATA GAA GGA CAA CTA GGG GAA AAC AAT        1968
Ala Leu Asn Asp Ser Glu Tyr Ile Glu Gly Gln Leu Gly Glu Asn Asn
                645                 650                 655

GAA CTT CTC GTG GAA CGA AAA CTA ATT GAG CCT TGC ACT GTC AAT AAT        2016
Glu Leu Leu Val Glu Arg Lys Leu Ile Glu Pro Cys Thr Val Asn Asn
```

```
                    660              665              670
AAG CGG TAT TTT AAG TTT GGG GCA GAT TAT GTA TAT TTT GAG GAT TAT    2064
Lys Arg Tyr Phe Lys Phe Gly Ala Asp Tyr Val Tyr Phe Glu Asp Tyr
        675              680              685

GCG TAT GTC CGT AAA GTC CCG CTA TCG GAG ATA GAA CTG ATA AGT GCG    2112
Ala Tyr Val Arg Lys Val Pro Leu Ser Glu Ile Glu Leu Ile Ser Ala
        690              695              700

TAT GTG ATT AAA TCT ACT CTC CTA GAG GAT CGT GAA TTT CTC CAC TCA    2160
Tyr Val Ile Lys Ser Thr Leu Leu Glu Asp Arg Glu Phe Leu His Ser
705              710              715              720

AGT TAT ACA CGA GCT GAG CTG GAA GAT ACC GGC CCT TTT GAC TAC AGC    2208
Ser Tyr Thr Arg Ala Glu Leu Glu Asp Thr Gly Pro Phe Asp Tyr Ser
                725              730              735

GAG ATT CAA CGC CGC AAC CAA CTC CAC GCC TTA AAA TTT TAT GAT ATA    2256
Glu Ile Gln Arg Arg Asn Gln Leu His Ala Leu Lys Phe Tyr Asp Ile
        740              745              750

GAC AGC ATA GTC AGA GTG GAT AAT AAT CTT GTC ATC ATG CGT GGT ATG    2304
Asp Ser Ile Val Arg Val Asp Asn Asn Leu Val Ile Met Arg Gly Met
        755              760              765

GCA AAT TTT TTT CAG GGA CTC GGG GAT GTG GGG GCT GGT TTC GGC AAG    2352
Ala Asn Phe Phe Gln Gly Leu Gly Asp Val Gly Ala Gly Phe Gly Lys
        770              775              780

GTG GTC TTA GGG GCT GCG AGT GCG GTA ATC TCA ACA GTA TCA GGC GTA    2400
Val Val Leu Gly Ala Ala Ser Ala Val Ile Ser Thr Val Ser Gly Val
785              790              795              800

TCA TCA TTT CTA AAC AAC CCA TTT GGA GCA TTG GCC GTG GGA CTG TTA    2448
Ser Ser Phe Leu Asn Asn Pro Phe Gly Ala Leu Ala Val Gly Leu Leu
            805              810              815

ATA TTA GCT GGC ATC GTC GCA GCA TTC CTG GCA TAT CGC TAT ATA TCT    2496
Ile Leu Ala Gly Ile Val Ala Ala Phe Leu Ala Tyr Arg Tyr Ile Ser
            820              825              830

AGA TTA CGT GCA AAT CCA ATG AAA GCC TTA TAT CCT GTG ACG ACT AGG    2544
Arg Leu Arg Ala Asn Pro Met Lys Ala Leu Tyr Pro Val Thr Thr Arg
        835              840              845

AAT TTG AAA CAG ACG GCT AAG AGC CCC GCC TCA ACG GCT GGT GGG GAT    2592
Asn Leu Lys Gln Thr Ala Lys Ser Pro Ala Ser Thr Ala Gly Gly Asp
        850              855              860

AGC GAC CCG GGA GTC GAT GAC TTC GAT GAG GAA AAG CTA ATG CAG GCA    2640
Ser Asp Pro Gly Val Asp Asp Phe Asp Glu Glu Lys Leu Met Gln Ala
865              870              875              880

AGG GAG ATG ATA AAA TAT ATG TCC CTC GTA TCG GCT ATG GAG CAA CAA    2688
Arg Glu Met Ile Lys Tyr Met Ser Leu Val Ser Ala Met Glu Gln Gln
            885              890              895

GAA CAT AAG GCG ATG AAA AAG AAT AAG GGC CCA GCG ATC CTA ACG AGT    2736
Glu His Lys Ala Met Lys Lys Asn Lys Gly Pro Ala Ile Leu Thr Ser
        900              905              910

CAT CTC ACT AAC ATG GCC CTC CGT CGC CGT GGA CCT AAA TAC CAA CGC    2784
His Leu Thr Asn Met Ala Leu Arg Arg Arg Gly Pro Lys Tyr Gln Arg
        915              920              925

CTC AAT AAT CTT GAT AGC GGT GAT GAT ACT GAA ACA AAT CTT GTC        2829
Leu Asn Asn Leu Asp Ser Gly Asp Asp Thr Glu Thr Asn Leu Val
        930              935              940

(2) INFORMATION FOR SEQ ID NO:2:

(i) SEQUENCE CHARACTERISTICS:
        (A) LENGTH: 1119
        (B) TYPE: Nucleic Acid
        (C) STRANDEDNESS: Single
        (D) TOPOLOGY: Linear (ii) MOLECULE TYPE:
```

(A) DESCRIPTION: DNA (iii) HYPOTHETICAL: No (iv) ANTI-SENSE: No (vi) ORIGINAL SOURCE:
  (A) ORGANISM: Feline herpesvirus
  (B) STRAIN: 1
  (C) INDIVIDUAL ISOLATE: C-27
  (G) CELL TYPE: N/A (ix) FEATURE:
  (A) NAME/KEY:
  (B) LOCATION:
  (C) IDENTIFICATION METHOD: Sequencing
  (D) OTHER INFORMATION: DNA and deduced polypeptide (xi) SEQUENCE DESCRIPTION: SEQ ID NO:2:

```
ATG ACA CGT CTA CAT TTT TGG TGG TGT GGA ATC TTT GCG GTC CTG AAA       48
Met Thr Arg Leu His Phe Trp Trp Cys Gly Ile Phe Ala Val Leu Lys
              5                  10                  15

TAT CTG GTA TGT ACT TCA AGC CTT ACG ACC ACG CCA AAA ACA ACT ACG       96
Tyr Leu Val Cys Thr Ser Ser Leu Thr Thr Thr Pro Lys Thr Thr Thr
             20                  25                  30

GTT TAT GTG AAG GGA TTT AAT ATA CCT CCA CTA CGC TAC AAT TAT ACT      144
Val Tyr Val Lys Gly Phe Asn Ile Pro Pro Leu Arg Tyr Asn Tyr Thr
             35                  40                  45

CAA GCC AGA ATC GTG CCA AAA ATT CCC CAG GCG ATG GAT CCG AAG ATA      192
Gln Ala Arg Ile Val Pro Lys Ile Pro Gln Ala Met Asp Pro Lys Ile
 50                  55                  60

ACA GCT GAA GTA CGT TAT GTA ACA TCA ATG GAT TCA TGT GGG ATG GTG      240
Thr Ala Glu Val Arg Tyr Val Thr Ser Met Asp Ser Cys Gly Met Val
 65                  70                  75                  80

GCA TTG ATA TCA GAG CCG GAT ATA GAC GCT ACT ATT CGA ACC ATA CAA      288
Ala Leu Ile Ser Glu Pro Asp Ile Asp Ala Thr Ile Arg Thr Ile Gln
             85                  90                  95

CTA TCT CAA AAA AAA ACA TAT AAC GCG ACT ATA AGT TGG TTT AAG GTA      336
Leu Ser Gln Lys Lys Thr Tyr Asn Ala Thr Ile Ser Trp Phe Lys Val
            100                 105                 110

ACC CAG GGT TGT GAA TAC CCT ATG TTT CTT ATG GAT ATG AGA CTT TGT      384
Thr Gln Gly Cys Glu Tyr Pro Met Phe Leu Met Asp Met Arg Leu Cys
            115                 120                 125

GAT CCT AAA CGG GAA TTT GGA ATA TGT GCT TTA CGG TCG CCT TCA TAT      432
Asp Pro Lys Arg Glu Phe Gly Ile Cys Ala Leu Arg Ser Pro Ser Tyr
            130                 135                 140

TGG TTG GAA CCT TTA ACA AAG TAT ATG TTC CTA ACA GAC GAT GAA CTG      480
Trp Leu Glu Pro Leu Thr Lys Tyr Met Phe Leu Thr Asp Asp Glu Leu
145                 150                 155                 160

GGT TTG ATT ATG ATG GCC CCG GCC CAA TTT AAT CAA GGA CAA TAT CGA      528
Gly Leu Ile Met Met Ala Pro Ala Gln Phe Asn Gln Gly Gln Tyr Arg
                165                 170                 175

AGA GTT ATA ACC ATC GAT GGT TCC ATG TTT TAT ACA GAT TTT ATG GTA      576
Arg Val Ile Thr Ile Asp Gly Ser Met Phe Tyr Thr Asp Phe Met Val
            180                 185                 190

CAA CTA TCT CCA ACG CCA TGT TGG TTC GCA AAA CCC GAT AGA TAC GAA      624
Gln Leu Ser Pro Thr Pro Cys Trp Phe Ala Lys Pro Asp Arg Tyr Glu
            195                 200                 205

GAG ATT CTA CAT GAA TGG TGT CGA AAT GTT AAA ACT ATT GGC CTT GAT      672
Glu Ile Leu His Glu Trp Cys Arg Asn Val Lys Thr Ile Gly Leu Asp
210                 215                 220

GGA GCT CGT GAT TAC CAC TAT TAT TGG GTA CCC TAT AAC CCA CAA CCT      720
Gly Ala Arg Asp Tyr His Tyr Tyr Trp Val Pro Tyr Asn Pro Gln Pro
225                 230                 235                 240
```

```
CAC CAT AAA GCC GTA CTC TTA TAT TGG TAT CGG ACT CAT GGC CGA GAA    768
His His Lys Ala Val Leu Leu Tyr Trp Tyr Arg Thr His Gly Arg Glu
            245                 250                 255

CCC CCA GTA AGA TTC CAA GAG GCC ATT CGA TAT GAT CGT CCC GCC ATA    816
Pro Pro Val Arg Phe Gln Glu Ala Ile Arg Tyr Asp Arg Pro Ala Ile
            260                 265                 270

CCG TCT GGG AGT GAG GAT TCG AAA CGG TCC AAC GAC TCT AGA GGA GAA    864
Pro Ser Gly Ser Glu Asp Ser Lys Arg Ser Asn Asp Ser Arg Gly Glu
            275                 280                 285

TCG AGT GGA CCC AAT TGG ATA GAC ATT GAA AAT TAC ACT CCT AAA AAT    912
Ser Ser Gly Pro Asn Trp Ile Asp Ile Glu Asn Tyr Thr Pro Lys Asn
290                 295                 300

AAT GTG CCT ATT ATA ATA TCT GAC GAT GAC GTT CCT ACA GCC CCT CCC    960
Asn Val Pro Ile Ile Ile Ser Asp Asp Asp Val Pro Thr Ala Pro Pro
305                 310                 315                 320

AAG GGC ATG AAT AAT CAG TCA GTA GTG ATA CCC GCA ATC GTA CTA AGT   1008
Lys Gly Met Asn Asn Gln Ser Val Val Ile Pro Ala Ile Val Leu Ser
            325                 330                 335

TGT CTT ATA ATA GCA CTG ATT CTA GGA GTG ATA TAT TAT ATT TTG AGG   1056
Cys Leu Ile Ile Ala Leu Ile Leu Gly Val Ile Tyr Tyr Ile Leu Arg
            340                 345                 350

GTA AAG AGG TCT CGA TCA ACT GCA TAT CAA CAA CTT CCT ATA ATA CAT   1104
Val Lys Arg Ser Arg Ser Thr Ala Tyr Gln Gln Leu Pro Ile Ile His
            355                 360                 365

ACA ACT CAC CAT CCT                                                1119
Thr Thr His His Pro
370
```

(2) INFORMATION FOR SEQ ID NO:3:

(i) SEQUENCE CHARACTERISTICS:
        (A) LENGTH: 179
        (B) TYPE: Amino Acid
        (C) STRANDEDNESS: Single
        (D) TOPOLOGY: Linear (ii) MOLECULE TYPE:
        (A) DESCRIPTION: Polypeptide (iii) HYPOTHETICAL: No (iv) ANTI-SENSE: No (vi) ORIGINAL SOURCE:
        (A) ORGANISM: Feline herpesvirus-1
        (B) STRAIN: 1
        (C) INDIVIDUAL ISOLATE: C-27
        (G) CELL TYPE: N/A (ix) FEATURE:
        (A) NAME/KEY:
        (B) LOCATION:
        (C) IDENTIFICATION METHOD: Deduced sequence
        (D) OTHER INFORMATION: ICP18.5

(xi) SEQUENCE DESCRIPTION: SEQ ID NO:3:

```
Phe Glu Leu Val Asn Gly Pro Leu Phe Asp His Asp Ser His Asn
                5                  10                  15

Phe Ala Gln Pro Pro Asn Thr Ala Phe Tyr Phe Ser Val Glu Asn Val
            20                  25                  30

Gly Leu Leu Pro His Leu Lys Glu Glu Leu Ala Gly Phe Met Leu Ser
            35                  40                  45

Ser Thr Arg Gly Gly Trp Thr Val Ser Lys Phe Gln Arg Phe Tyr Tyr
        50                  55                  60

Phe Gly Asp Asp Thr Ser Gly Val Thr Thr Thr Gln Arg Leu Ala Trp
```

```
                65                  70                  75
Lys Tyr Ile Arg Glu Leu Ile Leu Ala Ser Ala Ile Phe Ser Ser Val
 80                  85                  90                  95

Phe His Cys Gly Glu Val Lys Leu Ala Thr Leu Leu His Arg Thr Arg
                    100                 105                 110

Pro Ala Asn Thr Gly Thr Gln Ile Cys Pro Pro Gly Ile Tyr Leu Thr
                    115                 120                 125

Tyr Glu Glu Ser Cys Pro Leu Val Ala Ile Leu Gly Ser Gly Asp Glu
                130                 135                 140

Gly Val Val Gly Arg Asp Thr Val Ala Ile Phe Asp Arg Asp Val Phe
                145                 150                 155

Ser Leu Leu Tyr Ser Val Leu Gln Arg Leu Ala Pro Asp Met Val Thr
160                 165                 170                 175

Asp Arg Arg Asp (2) INFORMATION FOR SEQ ID NO:4:

(i) SEQUENCE CHARACTERISTICS:
        (A) LENGTH: 943
        (B) TYPE:  Amino Acid
        (C) STRANDEDNESS: Single
        (D) TOPOLOGY:  Linear (ii) MOLECULE TYPE:
        (A) DESCRIPTION: Polypeptide (iii) HYPOTHETICAL:  No (iv) ANTI-SENSE:  No (vi) ORIGINAL SOURCE:
        (A) ORGANISM:  Feline herpesvirus-1
        (B) STRAIN:  1
        (C) INDIVIDUAL ISOLATE:  C-27
        (G) CELL TYPE:  N/A (ix) FEATURE:
        (A) NAME/KEY:
        (B) LOCATION:
        (C) IDENTIFICATION METHOD:  Deduced sequence
        (D) OTHER INFORMATION:  gB (xi) SEQUENCE DESCRIPTION: SEQ ID NO:4:

Met Ser Thr Arg Gly Asp Leu Gly Lys Arg Arg
                              5                  10

Gly Ser Arg Trp Gln Gly His Ser Gly Tyr Phe Arg Gln Arg Cys Phe
            15                  20                  25

Phe Pro Ser Leu Leu Gly Ile Ala Ala Thr Gly Ser Arg His Gly Asn
 30                  35                  40

Gly Ser Ser Gly Leu Thr Arg Leu Ala Arg Tyr Val Ser Phe Ile Trp
 45                  50                  55                  60

Ile Val Leu Phe Leu Val Gly Pro Arg Pro Val Glu Gly Gln Ser Gly
                 65                  70                  75

Ser Thr Ser Glu Gln Pro Arg Arg Thr Val Ala Thr Pro Glu Val Gly
                 80                  85                  90

Val His His Gln Asn Gln Leu Gln Ile Pro Pro Ile Cys Arg Tyr Glu
             95                  100                 105

Glu Ala Leu Arg Ala Ser Gln Ile Glu Ala Asn Gly Pro Ser Thr Phe
            110                 115                 120

Tyr Met Cys Pro Pro Ser Gly Ser Thr Val Val Arg Leu Glu Pro
125                 130                 135                 140

Pro Arg Ala Cys Pro Asp Tyr Lys Leu Gly Lys Asn Phe Thr Glu Gly
```

-continued

```
                145                 150                 155
Ile Ala Val Ile Phe Lys Glu Asn Ile Ala Pro Tyr Lys Phe Lys Ala
                    160                 165                 170
Asn Ile Tyr Tyr Lys Asn Ile Ile Met Thr Thr Val Trp Ser Gly Ser
            175                 180                 185
Ser Tyr Ala Val Thr Thr Asn Arg Tyr Thr Asp Arg Val Pro Val Lys
        190                 195                 200
Val Gln Glu Ile Thr Asp Leu Ile Asp Arg Arg Gly Met Cys Leu Ser
205                 210                 215                 220
Lys Ala Asp Tyr Val Arg Asn Asn Tyr Gln Phe Thr Ala Phe Asp Arg
                225                 230                 235
Asp Glu Asp Pro Arg Glu Leu Pro Leu Lys Pro Pro Ser Ser Thr Leu
            240                 245                 250
Ser Arg Val Arg Gly Trp His Thr Asn Glu Thr Tyr Thr Lys Ile Val
        255                 260                 265
Leu Leu Asp Phe His His Ser Gly Thr Ser Val Asn Cys Ile Val Glu
270                 275                 280
Glu Val Asp Ala Arg Ser Val Tyr Pro Tyr Asp Ser Phe Ala Ile Ser
285                 290                 295                 300
Thr Gly Asp Val Ile His Met Ser Pro Phe Phe Gly Leu Arg Asp Gly
                305                 310                 315
Ala His Val Glu His Thr Ser Tyr Ser Ser Asp Arg Phe Gln Gln Ile
            320                 325                 330
Glu Gly Tyr Tyr Pro Ile Asp Leu Asp Thr Asp Tyr Thr Gly Ala Pro
        335                 340                 345
Val Ser Arg Asn Phe Leu Glu Thr Pro His Val Thr Val Ala Trp Asn
350                 355                 360
Trp Thr Pro Lys Ser Gly Arg Val Cys Thr Leu Ala Lys Trp Arg Glu
365                 370                 375                 380
Ile Asp Glu Met Leu Pro Met Asn Ile Gly Ser Tyr Arg Phe Thr Ala
                385                 390                 395
Lys Thr Ile Ser Ala Thr Phe Ile Ser Asn Thr Ser Gln Phe Glu Ile
            400                 405                 410
Asn Arg Ile Arg Leu Gly Asp Cys Ala Thr Lys Glu Ala Ala Glu Ala
        415                 420                 425
Ile Asp Arg Ile Tyr Lys Ser Lys Tyr Ser Lys Thr His Ile Gln Thr
430                 435                 440
Gly Thr Leu Glu Thr Tyr Leu Ala Arg Gly Gly Phe Leu Ile Ala Phe
445                 450                 455                 460
Arg Pro Met Ile Ser Asn Glu Leu Ala Lys Leu Tyr Ile Asn Glu Leu
                465                 470                 475
Ala Arg Ser Asn Arg Thr Val Val Asp Leu Ser Ala Leu Leu Asn Pro
            480                 485                 490
Ser Gly Glu Thr Val Gln Arg Thr Arg Ser Val Pro Ser Asn Gln
        495                 500                 505
His His Arg Ser Arg Arg Ser Thr Ile Glu Gly Ile Glu Thr Val
        510                 515                 520
Asn Asn Ala Ser Leu Leu Lys Thr Thr Ser Ser Val Glu Phe Ala Met
525                 530                 535                 540
Leu Gln Phe Ala Tyr Asp Tyr Ile Gln Ala His Val Asn Glu Met Leu
                545                 550                 555
Ser Arg Ile Ala Thr Ala Trp Cys Thr Leu Gln Asn Arg Glu His Val
            560                 565                 570
```

| | | | | | | | | | | | |
|---|---|---|---|---|---|---|---|---|---|---|---|
| Leu | Trp | Thr | Glu | Thr | Leu | Lys | Leu | Asn | Pro | Gly | Gly | Val | Val | Ser | Met |
| | | 575 | | | | 580 | | | | 585 | |

Leu Trp Thr Glu Thr Leu Lys Leu Asn Pro Gly Gly Val Val Ser Met
            575                 580                 585

Ala Leu Glu Arg Arg Val Ser Ala Arg Leu Leu Gly Asp Ala Val Ala
            590                 595                 600

Val Thr Gln Cys Val Asn Ile Ser Ser Gly His Val Tyr Ile Gln Asn
605                 610                 615                 620

Ser Met Arg Val Thr Gly Ser Ser Thr Thr Cys Tyr Ser Arg Pro Leu
            625                 630                 635

Val Ser Phe Arg Ala Leu Asn Asp Ser Glu Tyr Ile Glu Gly Gln Leu
            640                 645                 650

Gly Glu Asn Asn Glu Leu Leu Val Glu Arg Lys Leu Ile Glu Pro Cys
            655                 660                 665

Thr Val Asn Asn Lys Arg Tyr Phe Lys Phe Gly Ala Asp Tyr Val Tyr
            670                 675                 680

Phe Glu Asp Tyr Ala Tyr Val Arg Lys Val Pro Leu Ser Glu Ile Glu
685                 690                 695                 700

Leu Ile Ser Ala Tyr Val Ile Lys Ser Thr Leu Leu Glu Asp Arg Glu
            705                 710                 715

Phe Leu His Ser Ser Tyr Thr Arg Ala Glu Leu Glu Asp Thr Gly Pro
            720                 725                 730

Phe Asp Tyr Ser Glu Ile Gln Arg Arg Asn Gln Leu His Ala Leu Lys
            735                 740                 745

Phe Tyr Asp Ile Asp Ser Ile Val Arg Val Asp Asn Asn Leu Val Ile
            750                 755                 760

Met Arg Gly Met Ala Asn Phe Phe Gln Gly Leu Gly Asp Val Gly Ala
765                 770                 775                 780

Gly Phe Gly Lys Val Val Leu Gly Ala Ala Ser Ala Val Ile Ser Thr
            785                 790                 795

Val Ser Gly Val Ser Ser Phe Leu Asn Asn Pro Phe Gly Ala Leu Ala
            800                 805                 810

Val Gly Leu Leu Ile Leu Ala Gly Ile Val Ala Ala Phe Leu Ala Tyr
            815                 820                 825

Arg Tyr Ile Ser Arg Leu Arg Ala Asn Pro Met Lys Ala Leu Tyr Pro
            830                 835                 840

Val Thr Thr Arg Asn Leu Lys Gln Thr Ala Lys Ser Pro Ala Ser Thr
845                 850                 855                 860

Ala Gly Gly Asp Ser Asp Pro Gly Val Asp Asp Phe Asp Glu Glu Lys
            865                 870                 875

Leu Met Gln Ala Arg Glu Met Ile Lys Tyr Met Ser Leu Val Ser Ala
            880                 885                 890

Met Glu Gln Gln Glu His Lys Ala Met Lys Lys Asn Lys Gly Pro Ala
            895                 900                 905

Ile Leu Thr Ser His Leu Thr Asn Met Ala Leu Arg Arg Arg Gly Pro
            910                 915                 920

Lys Tyr Gln Arg Leu Asn Asn Leu Asp Ser Gly Asp Asp Thr Glu Thr
925                 930                 935                 940

Asn Leu Val (2) INFORMATION FOR SEQ ID NO:5:

(i) SEQUENCE CHARACTERISTICS:
        (A) LENGTH: 3339
        (B) TYPE: Nucleic Acid
        (C) STRANDEDNESS: Double
        (D) TOPOLOGY: Linear (ii) MOLECULE TYPE:
    (A) DESCRIPTION: DNA (iii) HYPOTHETICAL: No (iv) ANTI-SENSE: No (vi) ORIGINAL SOURCE:
    (A) ORGANISM: Feline herpesvirus-1
    (B) STRAIN: 1
    (C) INDIVIDUAL ISOLATE: C-27
    (G) CELL TYPE: N/A (ix) FEATURE:
    (A) NAME/KEY:
    (B) LOCATION:
    (C) IDENTIFICATION METHOD: Sequencing
    (D) OTHER INFORMATION: DNA encoding ICP18.5 and gB (xi) SEQUENCE DESCRIPTION: SEQ ID NO:5:

```
 TT TTT GAG CTG GTG AAC GGG CCT CTA TTC GAC CAC GAC AGT CAT AAC      47

TTT GCC CAA CCC CCC AAC ACA GCG TTT TAT TTC AGT GTT GAG AAC GTT      95

GGT CTG CTT CCA CAT TTA AAA GAA GAA TTG GCG GGA TTT ATG TTA AG     143

TCC ACC CGG GGT GGG TGG ACG GTG AGT AAA TTT CAA AGA TTT TAC TA     191

TTC GGT GAT GAT ACG TCT GGC GTC ACA ACA ACT CAG CGG TTG GCT TG     239

AAA TAT ATC CGT GAG CTC ATT CTA GCA TCT GCC ATA TTT TCC TCC GT     287

TTT CAC TGC GGT GAG GTG AAG CTT GCT ACG CTC TTG CAT CGC ACA CG     335

CCG GCT AAT ACA GGT ACC CAG ATC TGC CCA CCC GGC ATT TAT CTA AC     383

TAC GAA GAA TCATG TCC ACT CGT GGC GAT CTT GGG AAG CGG CGA CGA      430

GGG AGT CGT TGG CAG GGA CAC AGT GGC TAT TTT CGA CAG AGA TGT TT     478

TTC CCT TCT CTA CTC GGT ATT GCA GCG ACT GGC TCC AGA CAT GGT AA     526

GGA TCG TCG GGA TTA ACC AGA CTA GCT AGA TAT GTT TCA TTT ATC TG     574

ATC GTA CTA TTC TTA GTC GGT CCC CGT CCA GTA GAG GGT CAA TCT GG     622

AGC ACA TCG GAA CAA CCC CGG CGG ACT GTA GCT ACC CCT GAG GTA GG     670

GTA CAC CAC CAA AAC CAA CTA CAG ATC CCA CCG ATA TGT CGA TAT GA     718

GAA GCT CTC CGT GCG TCC CAA ATA GAG GCT AAC GGA CCA TCG ACT TT     766

TAT ATG TGT CCA CCA CCT TCA GGA TCT ACT GTC GTG CGT TTA GAG CC     814

CCA CGG GCC TGT CCA GAT TAT AAA CTA GGG AAA AAT TTT ACC GAG GG     862

ATA GCT GTA ATA TTT AAA GAA AAT ATA GCG CCA TAT AAA TTC AAG GC     910

AAT ATA TAC TAT AAA AAC ATT ATT ATG ACA ACG GTA TGG TCT GGG AG     958

TCC TAT GCC GTT ACA ACC AAC CGA TAT ACA GAC AGG GTT CCC GTG A     1006

GTT CAA GAG ATT ACA GAT CTC ATA GAT AGA CGG GGT ATG TGC CTC T     1054

AAA GCT GAT TAC GTT CGT AAC AAT TAT CAA TTT ACG GCC TTT GAT C     1102

GAC GAG GAT CCC AGA GAA CTG CCT CTG AAA CCT CCA AGT TCA ACA C     1150

TCC AGA GTC CGT GGA TGG CAC ACC AAT GAA ACA TAC ACA AAG ATC G     1198

CTG CTG GAT TTC CAC CAC TCT GGG ACC TCT GTA AAT TGC ATC GTA G     1246

GAA GTG GAT GCA AGA TCT GTA TAT CCA TAT GAC TCA TTT GCT ATC T     1294

ACT GGT GAC GTG ATT CAC ATG TCT CCA TTC TTT GGG CTG AGG GAT G     1342

GCC CAT GTA GAA CAT ACT AGT TAT TCT TCA GAC AGA TTT CAA CAA A     1390

GAG GGA TAC TAT CCA ATA GAC TTG GAT ACC GAT TAC ACT GGG GCA C     1438
```

```
GTT TCT CGC AAT TTT TTG GAA ACT CCG CAT GTG ACA GTG GCC TGG A      1486

TGG ACC CCA AAG TCT GGT CGG GTA TGT ACC TTA GCC AAA TGG AGG G      1534

ATA GAT GAA ATG CTA CCG ATG AAT ATA GGC TCC TAT AGA TTT ACA G      1582

AAG ACC ATA TCC GCT ACT TTC ATC TCC AAT ACT TCA CAA TTT GAA A      1630

AAT CGT ATC CGT TTG GGG GAC TGT GCC ACC AAG GAG GCA GCC GAA G      1678

ATA GAC CGG ATT TAT AAG AGT AAA TAT AGT AAA ACT CAT ATT CAG A      1726

GGA ACC CTG GAG ACC TAC CTA GCC CGT GGG GGA TTT CTA ATA GCT T      1774

CGT CCC ATG ATC AGC AAC GAA CTA GCA AAG TTA TAT ATC AAT GAA T      1822

GCA CGT TCC AAT CGC ACG GTA GTG GAT CTC AGT GCA CTC CTC AAT C      1870

TCT GGG GAA ACA GTA CAA CGA ACT AGA AGA TCG GTC CCA TCT AAT C      1918

CAT CAT AGG TCG CGG CGC AGC ACA ATA GAG GGG GGT ATA GAA ACC G      1966

AAC AAT GCA TCA CTC CTC AAG ACC ACC TCA TCT GTG GAA TTC GCA A      2014

CTA CAA TTT GCC TAT GAC TAC ATA CAA GCC CAT GTA AAT GAA ATG T      2062

AGT CGG ATA GCC ACT GCC TGG TGT ACA CTT CAG AAC CGC GAA CAT G      2110

CTG TGG ACA GAG ACC CTA AAA CTC AAT CCC GGT GGG GTG GTC TCG A      2158

GCC CTA GAA CGT CGT GTA TCC GCG CGC CTA CTT GGA GAT GCC GTC G      2206

GTA ACA CAA TGT GTT AAC ATT TCT AGC GGA CAT GTC TAT ATC CAA A      2254

TCT ATG CGG GTG ACG GGT TCA TCA ACG ACA TGT TAC AGC CGC CCT C      2302

GTT TCC TTC CGT GCC CTC AAT GAC TCC GAA TAC ATA GAA GGA CAA C      2350

GGG GAA AAC AAT GAA CTT CTC GTG GAA CGA AAA CTA ATT GAG CCT T      2398

ACT GTC AAT AAT AAG CGG TAT TTT AAG TTT GGG GCA GAT TAT GTA T      2446

TTT GAG GAT TAT GCG TAT GTC CGT AAA GTC CCG CTA TCG GAG ATA G      2494

CTG ATA AGT GCG TAT GTG ATT AAA TCT ACT CTC CTA GAG GAT CGT G      2542

TTT CTC CAC TCA AGT TAT ACA CGA GCT GAG CTG GAA GAT ACC GGC C      2590

TTT GAC TAC AGC GAG ATT CAA CGC CGC AAC CAA CTC CAC GCC TTA A      2638

TTT TAT GAT ATA GAC AGC ATA GTC AGA GTG GAT AAT AAT CTT GTC A      2686

ATG CGT GGT ATG GCA AAT TTT TTT CAG GGA CTC GGG GAT GTG GGG G      2734

GGT TTC GGC AAG GTG GTC TTA GGG GCT CGG AGT GCG GTA ATC TCA A      2782

GTA TCA GGC GTA TCA TCA TTT CTA AAC AAC CCA TTT GGA GCA TTG G      2830

GTG GGA CTG TTA ATA TTA GCT GGC ATC GTC GCA GCA TTC CTG GCA T      2878

CGC TAT ATA TCT AGA TTA CGT GCA AAT CCA ATG AAA GCC TTA TAT C      2926

GTG ACG ACT AGG AAT TTG AAA CAG ACG GCT AAG AGC CCC GCC TCA A      2974

GCT GGT GGG GAT AGC GAC CCG GGA GTC GAT GAC TTC GAT GAG GAA A      3022

CTA ATG CAG GCA GGG AGA TGA TAA AAA TAT ATG TCC TCG TAT CGG      3070

ATG GAG CAA CAA GAA CAT AAG GCG ATG AAA AAG AAT AAG GGC CCA G      3118

ATC CTA ACG AGT CAT CTC ACT AAC ATG GCC CTC CGT CGC CGT GGA C      3166

AAA TAC CAA CGC CTC AAT AAT CTT GAT AGC GGT GAT GAT ACT GAA A      3214

AAT CTT GTC TAA CCAACCAGAC CATCTCTAAA TTTTTATCCA CAAAAAAGT T      3269

AGATAAT AAATTTTGAT CTCAAAATAT CCTGTATGTC ATCATTCTCC GCCCATTCA     3326

GTCACGGGAA TTC                                                     3339
```

(2) INFORMATION FOR SEQ ID NO:6:

(i) SEQUENCE CHARACTERISTICS:
        (A) LENGTH: 6176
        (B) TYPE: Nucleic Acid
        (C) STRANDEDNESS: Double
        (D) TOPOLOGY: Linear (ii) MOLECULE TYPE:
        (A) DESCRIPTION: DNA (iii) HYPOTHETICAL: No (iv) ANTI-SENSE: No (vi) ORIGINAL SOURCE:
        (A) ORGANISM: Feline herpesvirus-1
        (B) STRAIN: 1
        (C) INDIVIDUAL ISOLATE: C-27
        (G) CELL TYPE: N/A (ix) FEATURE:
        (A) NAME/KEY:
        (B) LOCATION:
        (C) IDENTIFICATION METHOD: Sequencing
        (D) OTHER INFORMATION: DNA encoding PK, gG, gD,
           gI, gE (xi) SEQUENCE DESCRIPTION: SEQ ID NO:6:

```
GAA TTC CCA GGC GAC CCG ACT TCT AAA TTA ACT ATA GAC TTT ATT CAT      48

TAT GCC TCA TGT GTA AGA CAG CCT TAT ACA CGA TAC GAT TGT ATG TCA      96

AAA TAC GAT TTG CCG CTA GAT GGG GAG TTT GTA GTG CAT AAG ATG TTG     144

ACT TTC GAT GCC AAG TTC CGA CCA TCG GCC GCT GAA ATT CTA AAC TAT     192

CCA ATG TTT CGT GAT ACA TAG TTACATCATT ATCTATGGGT GGGACTTTCC AC     245

CAAGACAG TATAAAGTAT TTGGGACTCC ACAATAGCAT TCATCCTTCT TACCCTTCTA     303

CGAGTAAGAA CTTCAATCAC TCAACTTGGA AGAAAA ATG GGA AAT CGT ATA CAT     357

ATT TTA ATA TGC ATT GCA GCA TTC TAC ATA ACC ATC GCG GCT GCT AGG     405

AAT GCC CCA ATG GAT CTC TGT TAC GCC GAC CCC AGA GAT ACA TCA CCA     453

CAA CCC ATA GGA CAT CCT AAT TAT AAA CAA GTG AAT ATA ACG ATC CAC     501

TAC CCC GCA CCA AAG TGG GGA TAT GTT GAA CAT TCC AGT GGA TGT GAA     549

TTA CGT TTA TTG GAC CCG AGA GTT GAT GTG TCT CTT CAA GAT CAC CAG     597

AGA AGG GCA GAC GCT ACG ATT GCT TGG ACT TTT GAT CTC GGA ACA TGT     645

CAA ATA CCT ATC GCG TAT AGA GAA TAT TAT AAC TGT ACT GGG AAT TTA     693

ATA CCC TCC CCA GAA ACT TGC GAA GGG TAT TCC GCG ACC TCC ATA CGC     741

TTC GAA GGT CTA ACC ATC TAT ACC TTG GTA AAT ATA AGT CTA CTC CTT     789

CAA CCA GGA ATA TTC GAT TCC GGG AGT TTC CTG TAT TCA TTT ATA TAT     837

GGT CAA AAT AGA TAC AAT GGA CGT ATT ATA GTT CAT GTA GAA AAA AAT     885

ACT GAT TAT CCC TGC AAA ATG TAT CAT GGA CTC ATG GCT CCA TTT GAC     933

CAT CAT CCC CAA AGC CAC GTT GAA ACT CCG AAT GAT AAG AAT CAT CGT     981

AGA GGG CGG GGA TGT TTT CCC GAA TTG GTG GAA CCT GTT CTA TGG GT     1029

AAT ATC AGC AGT GAT CTT ATT GGT GGT CCA CCT TTC GAC TAT AAT CA     1077

GAA GAT GAG GCT GAT ATT GAG AGT GAT GAG CTC CCG GAG GAG ATA TA     1125

ATA ACT ACT CAG ATT GTC GTG CGA CTA ATA TGT TTG TTC CGA GAG AG     1173
```

-continued

```
CCC TCA GTC AAA GTT CTT GGT TCT CAA AGT CTA CTG GTT GGT AGT TT        1221
GGT TTC CAG ATA ATT ACT CAA CCC TGG CAA CTG AAG CAG AAT GAA AG        1269
TAT GAT GGA CTA AGA AAT GCC TCT CTT GAA CCC CGA CAC CTT GAC TC        1317
AGT AAC GAT CGT GAT CTA CTA GAT GAA ACT GAA ATG ATT GGA TCG AT        1365
ATT ACG ACT CCA CCA CCA ACC CAT CCA AAA GGT GTC AAT GGG GGT TT        1413
CTC CAA GAT CTA CCA ATT ATC GAG CCT ACG ACC GAA CCA TGC TTA GT        1461
CAT ACA AAG ATC ATT GGG ATC GGA ACA GTA GTC GTT GTA TTT TTG TT        1509
TTT ATT CTC ATA TCC CTA TGT GTT TAT ACT TGC GTT CTA CGA TCC CG        1557
ATC GGT ATG GTA GAT CGC GCC TAT GTG AAA CAA GTA CGA TTT AAT TC        1605
AAT CCA TCA TAT CAA CAG TTG ACA AGA TAC CCC CAA CCA TAA TAAACT        1654
ATT AAATTTAATT AAAGTCTCAT ATGTGGGCT GTGGGACGA GGGGCTGTGG GGA          1711
GAGGGG CTGTGGGGAC GAGGGGCTGT GGGGACGAGG GGCTGTGGGG ACGAGGGGCT        1768
TGGGGACGA GGGGCTGTGG GGACGAGGGG CTGTGGGGAC GAGGGGCTGT GGGGACGA       1826
G GCTGTGGGG ACGAGGGGCT GTGGGACGAT ACAACCGAT AAATGTCGTA TATGA         1883
ATGTG GTGTTAACAT AACACGGATT TTTAAGCACA CCACATGACA CACCCCCACG A       1940
AACGGTTA AATCACCAGC TATGTGAACT GCCCTCCATT CTACTCAAAT GAGTGGTGG       1998
GTGTGGCATA TTAGAACCAT TTCGTCTA ATG ATG ACA CGT CTA CAT TTT TGG       2050
TGG TGT GGA ATC TTT GCG GTC CTG AAA TAT CTG GTA TGT ACT TCA AG       2098
CTT ACG ACC ACG CCA AAA ACA ACT ACG GTT TAT GTG AAG GGA TTT AA       2146
ATA CCT CCA CTA CGC TAC AAT TAT ACT CAA GCC AGA ATC GTG CCA AA       2194
ATT CCC CAG GCG ATG GAT CCG AAG ATA ACA GCT GAA GTA CGT TAT GT       2242
ACA TCA ATG GAT TCA TGT GGG ATG GTG GCA TTG ATA TCA GAG CCG GA       2290
ATA GAC GCT ACT ATT CGA ACC ATA CAA CTA TCT CAA AAA AAA ACA TA       2338
AAC GCG ACT ATA AGT TGG TTT AAG GTA ACC CAG GGT TGT GAA TAC CC       2386
ATG TTT CTT ATG GAT ATG AGA CTT TGT GAT CCT AAA CGG GAA TTT GG       2434
ATA TGT GCT TTA CGG TCG CCT TCA TAT TGG TTG GAA CCT TTA ACA AA       2482
TAT ATG TTC CTA ACA GAC GAT GAA CTG GGT TTG ATT ATG ATG GCC CC       2530
GCC CAA TTT AAT CAA GGA CAA TAT CGA AGA GTT ATA ACC ATC GAT GG       2578
TCC ATG TTT TAT ACA GAT TTT ATG GTA CAA CTA TCT CCA ACG CCA TG       2626
TGG TTC GCA AAA CCC GAT AGA TAC GAA GAG ATT CTA CAT GAA TGG TG       2674
CGA AAT GTT AAA ACT ATT GGC CTT GAT GGA GCT CGT GAT TAC CAC TA       2722
TAT TGG GTA CCC TAT AAC CCA CAA CCT CAC CAT AAA GCC GTA CTC TT       2770
TAT TGG TAT CGG ACT CAT GGC CGA GAA CCC CCA GTA AGA TTC CAA GA       2818
GCC ATT CGA TAT GAT CGT CCC GCC ATA CCG TCT GGG AGT GAG GAT TC       2866
AAA CGG TCC AAC GAC TCT AGA GGA GAA TCG AGT GGA CCC AAT TGG AT       2914
GAC ATT GAA AAT TAC ACT CCT AAA AAT AAT GTG CCT ATT ATA ATA TC       2962
GAC GAT GAC GTT CCT ACA GCC CCT CCC AAG GGC ATG AAT AAT CAG TC       3010
GTA GTG ATA CCC GCA ATC GTA CTA AGT TGT CTT ATA ATA GCA CTG AT       3058
CTA GGA GTG ATA TAT TAT ATT TTG AGG GTA AAG AGG TCT CGA TCA AC       3106
GCA TAT CAA CAA CTT CCT ATA ATA CAT ACA ACT CAC CAT CCT TAA GT       3154
```

| | |
|---|---|
| CACATTC CAATCGAGTT GGTAGGGAAG ATATGAAGTG GGCGGTACCA ACCATCATAA | 3211 |
| AATAGGTTGG AGTCTGGACC AACGTTCACT CTTTTGAGTG TAAAGGACCA CAGCATA | 3269 |
| TA CTTAAT ATG TCG TCG ATA GCC TTC ATC TAT ATA TTG ATG GCG ATT | 3316 |
| GGA ACA GTT TAT GGG ATT GTG TAT CGT GGA GAT CAT GTA AGT CTT CA | 3364 |
| GTT GAT ACA AGC TCC GGC TTT GTA ATA TAT CCA ACA CTG GAG AAT TT | 3412 |
| ACG ATC TAC GGC CAT CTA ATC TTT CTC GAC GAC CAA CCA TTA CCA GT | 3460 |
| AAC AAT TAT AAT GGA ACC CTC GAG ATT ATA CAT TAC AAC CAT CAC TC | 3508 |
| TCT TGC TAT AAA ATC GTT CAA GTA ATA GAA TAT TCA TCA TGT CCA CG | 3556 |
| GTA CGC AAT AAT GCT TTC CGG TCC TGT CTC CAC AAG ACC TCT ATG CA | 3604 |
| CAT AAC GAT CAG CTT TCC ATA AAC ACA TCC GTT GAA ACG GGG ATG TT | 3652 |
| TTG ACA ATA ACA TCT CCG AAA ATG GAA GAT GGT GGA ATC TAC GCA CT | 3700 |
| CGG GTA AGA TTT AAC CAT AAT AAC AAA GCT GAT GTA TTT GGC CTT TC | 3748 |
| GTG TTT GTT TAC TCA TTC GAT ACG CGT GGT CAT CGA CAT CAT GCG GA | 3796 |
| GAA AAT TTG AAT GGT GAA ATT CTT ACT ACT CCA TCA CCG ATG GAA AC | 3844 |
| TAT GTT AAA GTT AAC ACA CCA TAT GAA TAT CAT ATG GTG ACA ACT CA | 3892 |
| ACA ACT TCT AAT AAA TCG ATG GAG TCT GAA CCA TCA AAT ACA TCA AT | 3940 |
| TCA TGC CAT ACA TTT CAA AAT GAC CCG AAT GAG GGT GAG ACT TTA TA | 3988 |
| ACA CAC TTA TTG AAC ATC GCT GGA AAT ATA ACA TAT GAT GAC ATG GT | 4036 |
| ATG GAT GGC ACC ACA TTG AAA CCC AGA TTA ATC GAT ATG GGA CTT AA | 4084 |
| TTG TCT GTT ACA TCT TCC TTT AAA AAT GGA AAC CAC GCA AAA ATG GA | 4132 |
| ACC AGA CAG AAA GGT GGG TTT CTG TTA TAG TAA TCT AAT CGC AGT TT | 4180 |
| ACT ACT CTT GCG GTC ATC GGA TCC ATC ATC AAT AGT GCA ATA CGC AA | 4228 |
| CAT ATA ATG GTC TGT GCT GGG CGG CGG ATC TAT ATA CCA AAC AAC GA | 4276 |
| GGG CGA CCA TCA ACG GAA ATG ACA CGG TTT ACT CGC CAG ACT AAA CC | 4324 |
| TCG AAT TCC ACC CCA ACC GAT GGC GTC TCT AGA AGT CAG TTA ACC GT | 4372 |
| ATT AAC GAA GAA ACC TAA TATATTTATA AACAAATAAA ATACTTTTCA AAATG | 4426 |
| ATAT CTGGTCATGT GTAATGTTGA CGCATAGTGG GTGGTGACCT AAGATTATAT TA | 4483 |
| AATGTAG AAGGTTTTAT GCCCAGTTCA CAGTATCTAC TGTGACCTAC CCCGGGGTGG | 4540 |
| TAATAACAAT ACTATCGAAT AGCCAACA ATG GGA CTG CTT GTT ACC ATC CTC | 4592 |
| GTG ATA TTA TTG ATT GTT ACT TCA TCA AGT TCT ACT ATT CAT CAA GT | 4640 |
| ACG ATG ACA GAA GGT GCC GCA CTT TTA GTC GAT GGG GAT GGG ATC GA | 4688 |
| CCA CCT TTA AAC AAA ACT TCA CAT TTT TTG CGA GGT TGG ACA TTT CT | 4736 |
| GAG ACT CCG AAA GGA TGT ACA GGA GAG GTG AGT GTT CTA AAA GTA TG | 4784 |
| ATA GAT CGT GGG GTA TGT CCG GAT GAT ATC GTT ATA AAT AAG AGA TG | 4832 |
| GGT CAC AAA ATG CTT GAA ACC CCA CTA GCG TTG GGC GAA TTT GGA AT | 4880 |
| TCT AAT AGT TCT CTC ATC AGA ACC AAA GAC GTA TAT TTC GTG AAT AA | 4928 |
| ACC GTG TTT CCA ATT CTC ACA CCC GAA AAA AGT GGC CTT GGT ATT CA | 4976 |
| GGG GCC ACT ACG AAT ATA TCC GGG ATA TAT ACC CTG CAT GAG CAC GG | 5024 |
| GAT AAT GGA TGG AGT CAT CAA TCT ACA TTT TTT GTG ACC GTA AAG GC | 5072 |
| AAA CAT CCC GGA CCA TCG TTA ACC CCA GCA CCG GTT CAC TTA ATA AC | 5120 |

-continued

```
CCA CAT CGC CAT GGG GCA CAT TTC CAC GTA AGA AAC TAT CAT TCG CA      5168

GTC TAC ATT CCG GGA GAT AAG TTC TTA TTA GAA ATG CAC CTC AAA TC      5216

GAT ATC TAT GAT CCA GAA TTT TCA GCA ACA ATA GAC TGG TAT TTT AT      5264

GAG ACT GAT ATA AAA TGC CCA GTT TTT AGA ATT TAT GAA ACT TGT AT      5312

TTT CAC CCC CAT GCC GCA TCC TGT CTA CAT CCG GAA GAT CCC TCA TG      5360

AGT TTT ACA TCA CCA CTT CGA GCG GTA TCT TTA ATT AAT AGA TTT TA      5408

CCA AAA TGC GAT CAC AGA TAT GCC GAT TGG ACA TCC AGA TGT ATC AA      5456

ACT CCA AGT ATA AAT CAT ATG CCA TAT ATC GAA CAG CCG GCC AAT AA      5504

GTG GAT CTA AAG TTT ATC AAT GTA CCC ACC AAC GCT TCT GGG TTG TA      5552

GTA TTC ATA CTT CGT TAT AAT GGA CAT CCG GAA GAA TGG ACC TAT AC      5600

CTC ATA TCA ACA GGA GCT AAA TTT TTG AAT GTG ATT AGG GAT CTG AC      5648

CGC CCA CGT CTT GGT AGT CAT CAA ATA GAG ACC GAT ATT AGC ACA TC      5696

TCC GAG TCG CCT ACC ACG GAG ACA CCA CGA AAC ATA CAT ATA ACG TG      5744

GCG AGA CGT TAT CTA AAG GTT ATC ATA GGA ATA ATT TGC GTA GCT GG      5792

ATC CTT TTG ATT GTA ATC TCT ATC ACA TGT TAT ATT CGA TTT CGT CA      5840

ATG CGA TAT AAA CCA TAT GAA GTG ATC AAC CCA TTC CCT GCG GTA TA      5888

ACC AGC ATT CCT AGT AAC GAT CCC GAC GAA CTC TAC TTT GAA CGT AT      5936

GCA TCG AAC GAC GAA GAA TCG GCA GAT GAT TCT TTT GAT GAA TCA GA      5984

GAG GAG GAG CCA TTG AAT AAT CAT CAT ATT TCA ACA ACC CAA CAT AC      6032

GAT ATT AAT CCA GAA AAA TCC GGA TCT GGG TAC AGT GTA TGG TTT CG      6080

GAT ACA GAA GAT ACA TCA CCT CAG CCC CTA CAC GCT CCT CCA GAT TA      6128

AGT CGC GTA GTT AAA AGA TTA AAG TCT ATT TTA AAA TGA CCC GTC GA      6176
```

(2) INFORMATION FOR SEQ ID NO:7:

(i) SEQUENCE CHARACTERISTICS:
        (A) LENGTH: 70
        (B) TYPE: Amino Acid
        (C) STRANDEDNESS: Single
        (D) TOPOLOGY: Linear (ii) MOLECULE TYPE:
        (A) DESCRIPTION: Polypeptide (iii) HYPOTHETICAL: No (iv) ANTI-SENSE: No (vi) ORIGINAL SOURCE:
        (A) ORGANISM: Feline herpesvirus-1
        (B) STRAIN: 1
        (C) INDIVIDUAL ISOLATE: C-27
        (G) CELL TYPE: N/A (ix) FEATURE:
        (A) NAME/KEY:
        (B) LOCATION:
        (C) IDENTIFICATION METHOD: Deduced sequence
        (D) OTHER INFORMATION: pK (xi) SEQUENCE DESCRIPTION: SEQ ID NO:7:

Glu Phe Pro Gly Asp Pro Thr Ser Lys Leu Thr Ile Asp Phe Ile
              5                  10                  15

Tyr Ala Ser Cys Val Arg Gln Pro Tyr Thr Arg Tyr Asp Cys Met
          20                  25                  30

```
Lys Tyr Asp Leu Pro Leu Asp Gly Glu Phe Val Val His Lys Met
        35                  40                  45

Thr Phe Asp Ala Lys Phe Arg Pro Ser Ala Ala Glu Ile Leu Asn
        50                  55                  60

Pro Met Phe Arg Asp Thr
65                  70

(2) INFORMATION FOR SEQ ID NO:8:

(i) SEQUENCE CHARACTERISTICS:
        (A) LENGTH: 435
        (B) TYPE: Amino Acid
        (C) STRANDEDNESS: Single
        (D) TOPOLOGY: Linear (ii) MOLECULE TYPE:
        (A) DESCRIPTION:

(iii) HYPOTHETICAL: No (iv) ANTI-SENSE: No (vi) ORIGINAL SOURCE:
        (A) ORGANISM: Feline herpesvirus-1
        (B) STRAIN: 1
        (C) INDIVIDUAL ISOLATE: C-27
        (G) CELL TYPE: N/A (ix) FEATURE:
        (A) NAME/KEY:
        (B) LOCATION:
        (C) IDENTIFICATION METHOD: Deduced Sequence
        (D) OTHER INFORMATION: gG (xi) SEQUENCE DESCRIPTION: SEQ ID NO:8:

Met Gly Asn Arg IleHis
                                                5

Ile Leu Ile Cys Ile Ala Ala Phe Tyr Ile Thr Ile Ala Ala Ala
        10                  15                  20

Asn Ala Pro Met Asp Leu Cys Tyr Ala Asp Pro Arg Asp Thr Ser
        25                  30                  35

Gln Pro Ile Gly His Pro Asn Tyr Lys Gln Val Asn Ile Thr Ile
        40                  45                  50

Tyr Pro Ala Pro Lys Trp Gly Tyr Val Glu His Ser Ser Gly Cys
        55                  60                  65                  70

Leu Arg Leu Leu Asp Pro Arg Val Asp Val Ser Leu Gln Asp His
        75                  80                  85

Arg Arg Ala Asp Ala Thr Ile Ala Trp Thr Phe Asp Leu Gly Thr
        90                  95                  100

Gln Ile Pro Ile Ala Tyr Arg Glu Tyr Tyr Asn Cys Thr Gly Asn
        105                 110                 115

Ile Pro Ser Pro Glu Thr Cys Glu Gly Tyr Ser Ala Thr Ser Ile
        120                 125                 130

Phe Glu Gly Leu Thr Ile Tyr Thr Leu Val Asn Ile Ser Leu Leu
135                 140                 145                 150

Gln Pro Gly Ile Phe Asp Ser Gly Ser Phe Leu Tyr Ser Phe Ile
        155                 160                 165

Gly Gln Asn Arg Tyr Asn Gly Arg Ile Ile Val His Val Glu Lys
        170                 175                 180

Thr Asp Tyr Pro Cys Lys Met Tyr His Gly Leu Met Ala Pro Phe
        185                 190                 195

His His Pro Gln Ser His Val Glu Thr Pro Asn Asp Lys Asn His
```

```
                200             205             210
    Arg Gly Arg Gly Cys Phe Pro Glu Leu Val Glu Pro Val Leu Trp
    215             220             225             230

Asn Ile Ser Ser Asp Leu Ile Gly Gly Pro Pro Phe Asp Tyr Asn
                235             240             245

Glu Asp Glu Ala Asp Ile Glu Ser Asp Glu Leu Pro Glu Glu Ile
                250             255             260

Ile Thr Thr Gln Ile Val Val Arg Leu Ile Cys Leu Phe Arg Glu
                265             270             275

Pro Ser Val Lys Val Leu Gly Ser Gln Ser Leu Leu Val Gly Ser
            280             285             290

Gly Phe Gln Ile Ile Thr Gln Pro Trp Gln Leu Lys Gln Asn Glu
    295             300             305             310

Tyr Asp Gly Leu Arg Asn Ala Ser Leu Glu Pro Arg His Leu Asp
                315             320             325

Ser Asn Asp Arg Asp Leu Leu Asp Glu Thr Glu Met Ile Gly Ser
                330             335             340

Ile Thr Thr Pro Pro Pro Thr His Pro Lys Gly Val Asn Gly Gly
            345             350             355

Leu Gln Asp Leu Pro Ile Ile Glu Pro Thr Thr Glu Pro Cys Leu
    360             365             370

His Thr Lys Ile Ile Gly Ile Gly Thr Val Val Val Phe Leu
    375             380             385             390

Phe Ile Leu Ile Ser Leu Cys Val Tyr Thr Cys Val Leu Arg Ser
                395             400             405

Ile Gly Met Val Asp Arg Ala Tyr Val Lys Gln Val Arg Phe Asn
                410             415             420

Asn Pro Ser Tyr Gln Gln Leu Thr Arg Tyr Pro Gln Pro
                425             430             435

(2) INFORMATION FOR SEQ ID NO:9:

(i) SEQUENCE CHARACTERISTICS:
        (A) LENGTH: 373
        (B) TYPE: Amino Acid
        (C) STRANDEDNESS: Single
        (D) TOPOLOGY: Linear (ii) MOLECULE TYPE:
        (A) DESCRIPTION: Polypeptide (iii) HYPOTHETICAL: No (iv) ANTI-SENSE: No (vi) ORIGINAL SOURCE:
        (A) ORGANISM: Feline herpesvirus-1
        (B) STRAIN: 1
        (C) INDIVIDUAL ISOLATE: C-27
        (G) CELL TYPE: N/A (ix) FEATURE:
        (A) NAME/KEY:
        (B) LOCATION:
        (C) IDENTIFICATION METHOD: Deduced Sequence
        (D) OTHER INFORMATION: gD (xi) SEQUENCE DESCRIPTION: SEQ ID NO:9:

Met Thr Arg Leu His Phe Trp
                            5

Trp Cys Gly Ile Phe Ala Val Leu Lys Tyr Leu Val Cys Thr Ser S
                10              15              20
```

```
            Leu Thr Thr Thr Pro Lys Thr Thr Val Tyr Val Lys Gly Phe A
                25              30              35

Ile Pro Pro Leu Arg Tyr Asn Tyr Thr Gln Ala Arg Ile Val Pro L
                40              45              50                      55

Ile Pro Gln Ala Met Asp Pro Lys Ile Thr Ala Glu Val Arg Tyr V
                            60              65                  70

Thr Ser Met Asp Ser Cys Gly Met Val Ala Leu Ile Ser Glu Pro A
                        75              80              85

Ile Asp Ala Thr Ile Arg Thr Ile Gln Leu Ser Gln Lys Lys Thr T
                        90              95              100

Asn Ala Thr Ile Ser Trp Phe Lys Val Thr Gln Gly Cys Glu Tyr P
                        105             110             115

Met Phe Leu Met Asp Met Arg Leu Cys Asp Pro Lys Arg Glu Phe G
                120             125             130             135

Ile Cys Ala Leu Arg Ser Pro Ser Tyr Trp Leu Glu Pro Leu Thr L
                            140             145             150

Tyr Met Phe Leu Thr Asp Asp Glu Leu Gly Leu Ile Met Met Ala P
                            155             160             165

Ala Gln Phe Asn Gln Gly Gln Tyr Arg Arg Val Ile Thr Ile Asp
                        170             175             180

Ser Met Phe Tyr Thr Asp Phe Met Val Gln Leu Ser Pro Thr Pro
                        185             190             195

Trp Phe Ala Lys Pro Asp Arg Tyr Glu Glu Ile Leu His Glu Trp
                200             205             210             215

Arg Asn Val Lys Thr Ile Gly Leu Asp Gly Ala Arg Asp Tyr His
                            220             225             230

Tyr Trp Val Pro Tyr Asn Pro Gln Pro His His Lys Ala Val Leu
                        235             240             245

Tyr Trp Tyr Arg Thr His Gly Arg Glu Pro Pro Val Arg Phe Gln
                        250             255             260

Ala Ile Arg Tyr Asp Arg Pro Ala Ile Pro Ser Gly Ser Glu Asp
                        265             270             275

Lys Arg Ser Asn Asp Ser Arg Gly Glu Ser Ser Gly Pro Asn Trp I
                280             285             290             295

Asp Ile Glu Asn Tyr Thr Pro Lys Asn Asn Val Pro Ile Ile Ile S
                            300             305             310

Asp Asp Asp Val Pro Thr Ala Pro Pro Lys Gly Met Asn Asn Gln S
                        315             320             325

Val Val Ile Pro Ala Ile Val Leu Ser Cys Leu Ile Ile Ala Leu I
                        330             335             340

Leu Gly Val Ile Tyr Tyr Ile Leu Arg Val Lys Arg Ser Arg Ser T
                345             350             355

Ala Tyr Gln Gln Leu Pro Ile Ile His Thr Thr His His Pro
                360             365             370

(2) INFORMATION FOR SEQ ID NO:10:

(i) SEQUENCE CHARACTERISTICS:
        (A) LENGTH: 370
        (B) TYPE: Amino Acid
        (C) STRANDEDNESS: Single
        (D) TOPOLOGY: Linear (ii) MOLECULE TYPE:
        (A) DESCRIPTION: Polypeptide (iii) HYPOTHETICAL: No
```

-continued (iv) ANTI-SENSE: No (vi) ORIGINAL SOURCE:
    (A) ORGANISM: Feline herpesvirus-1
    (B) STRAIN: 1
    (C) INDIVIDUAL ISOLATE: C-27
    (G) CELL TYPE: N/A (ix) FEATURE:
    (A) NAME/KEY:
    (B) LOCATION:
    (C) IDENTIFICATION METHOD: Deduced Sequence
    (D) OTHER INFORMATION: gI (xi) SEQUENCE DESCRIPTION: SEQ ID NO:10:

```
Met Ser Ser Ile Ala Phe Ile Tyr Ile Leu Met Ala Ile
                 5                  10

Gly Thr Val Tyr Gly Ile Val Tyr Arg Gly Asp His Val Ser Leu
            15                  20                  25

Val Asp Thr Ser Ser Gly Phe Val Ile Tyr Pro Thr Leu Glu Asn
30                  35                  40                  45

Thr Ile Tyr Gly His Leu Ile Phe Leu Asp Asp Gln Pro Leu Pro
                50                  55                  60

Asn Asn Tyr Asn Gly Thr Leu Glu Ile Ile His Tyr Asn His His
                65                  70                  75

Ser Cys Tyr Lys Ile Val Gln Val Ile Glu Tyr Ser Ser Cys Pro
        80                  85                  90

Val Arg Asn Asn Ala Phe Arg Ser Cys Leu His Lys Thr Ser Met
        95                  100                 105

Gln Tyr Asp Gln Leu Ser Ile Asn Thr Ser Val Glu Thr Gly Met
110                 115                 120                 125

Leu Thr Ile Thr Ser Pro Lys Met Glu Asp Gly Ile Tyr Ala
                130                 135                 140

Arg Val Arg Phe Asn His Asn Asn Lys Ala Asp Val Phe Gly Leu
            145                 150                 155

Val Phe Val Tyr Ser Phe Asp Thr Arg Gly His Arg His His Ala
        160                 165                 170

Glu Asn Leu Asn Gly Glu Ile Leu Thr Thr Pro Ser Pro Met Glu
    175                 180                 185

Tyr Val Lys Val Asn Thr Pro Ile Tyr Asp His Met Val Thr Thr
190                 195                 200                 205

Thr Thr Ser Asn Lys Ser Met Glu Ser Glu Pro Ser Asn Thr Ser
                210                 215                 220

Ser Cys His Thr Phe Gln Asn Asp Pro Asn Glu Gly Glu Thr Leu
            225                 230                 235

Thr His Leu Leu Asn Ile Ala Gly Asn Ile Thr Tyr Asp Asp Met
        240                 245                 250

Met Asp Gly Thr Thr Leu Lys Pro Arg Leu Ile Asp Met Gly Leu
    255                 260                 265

Leu Ser Val Thr Ser Ser Phe Lys Asn Gly Asn His Ala Lys Met
270                 275                 280                 285

Thr Arg Gln Lys Gly Gly Phe Cys Tyr Ser Asn Leu Asn Arg Ser
                290                 295                 300

Thr Thr Leu Ala Val Ile Gly Ser Ile Asn Ser Ala Ile Arg
            305                 310                 315

His Ile Met Val Cys Ala Gly Arg Arg Ile Tyr Ile Pro Asn Asn
        320                 325                 330

Gly Arg Pro Ser Thr Glu Met Thr Arg Phe Thr Arg Gln Thr Lys
```

```
                     335                 340                 345
          Ser Asn Ser Thr Pro Thr Asp Gly Val Ser Arg Ser Gln Leu Thr
                 350                 355                 360                 365

Ile Asn Glu Glu Thr
                 370
```

(2) INFORMATION FOR SEQ ID NO:11:

(i) SEQUENCE CHARACTERISTICS:
        (A) LENGTH: 532
        (B) TYPE: Amino Acid
        (C) STRANDEDNESS: Single
        (D) TOPOLOGY: Linear (ii) MOLECULE TYPE:
        (A) DESCRIPTION: Polypeptide (iii) HYPOTHETICAL: No (iv) ANTI-SENSE: No (vi) ORIGINAL SOURCE:
        (A) ORGANISM: Feline herpesvirus-1
        (B) STRAIN: 1
        (C) INDIVIDUAL ISOLATE: C-27
        (G) CELL TYPE: N/A (ix) FEATURE:
        (A) NAME/KEY:
        (B) LOCATION:
        (C) IDENTIFICATION METHOD: Deduced Sequence
        (D) OTHER INFORMATION: gE (xi) SEQUENCE DESCRIPTION: SEQ ID NO:11:

```
          Met Gly Leu Leu Val Thr Ile Leu
                          5

Val Ile Leu Leu Ile Val Thr Ser Ser Ser Thr Ile His Gln V
              10                  15                  20

Thr Met Thr Glu Gly Ala Ala Leu Val Asp Gly Asp Gly Ile A
          25                  30                  35                  40

Pro Pro Leu Asn Lys Thr Ser His Phe Leu Arg Gly Trp Thr Phe L
                      45                  50                  55

Glu Thr Pro Lys Gly Cys Thr Gly Glu Val Ser Val Leu Lys Val C
                      60                  65                  70

Ile Asp Arg Gly Val Cys Pro Asp Ile Val Ile Asn Lys Arg C
                  75                  80                  85

Gly His Lys Met Leu Glu Thr Pro Leu Ala Leu Gly Glu Phe Gly I
                  90                  95                  100

Ser Asn Ser Ser Leu Ile Arg Thr Lys Asp Val Tyr Phe Val Asn L
              105                 110                 115                 120

Thr Val Phe Pro Ile Leu Thr Pro Glu Lys Ser Gly Leu Gly Ile G
                      125                 130                 135

Gly Ala Thr Thr Asn Ile Ser Gly Ile Tyr Thr Leu His Glu His G
                      140                 145                 150

Asp Asn Gly Trp Ser His Gln Ser Thr Phe Val Thr Val Lys A
                  155                 160                 165

Lys His Pro Gly Pro Ser Leu Thr Pro Ala Pro Val His Leu Ile T
                  170                 175                 180

Pro His Arg His Gly Ala His Phe His Val Arg Asn Tyr His Ser H
              185                 190                 195                 200

Val Tyr Ile Pro Gly Asp Lys Phe Leu Leu Glu Met His Leu Lys S
                      205                 210                 215
```

```
Asp Ile Tyr Asp Pro Glu Phe Ser Ala Thr Ile Asp Trp Tyr Phe M
            220                 225                 230

Glu Thr Asp Ile Lys Cys Pro Val Phe Arg Ile Tyr Glu Thr Cys I
        235                 240                 245

Phe His Pro His Ala Ala Ser Cys Leu His Pro Glu Asp Pro Ser C
    250                 255                 260

Ser Phe Thr Ser Pro Leu Arg Ala Val Ser Leu Ile Asn Arg Phe T
265                 270                 275                 280

Pro Lys Cys Asp His Arg Tyr Ala Asp Trp Thr Ser Arg Cys Ile A
                285                 290                 295

Thr Pro Ser Ile Asn His Met Pro Tyr Ile Glu Gln Pro Ala Asn A
            300                 305                 310

Val Asp Leu Lys Phe Ile Asn Val Pro Thr Asn Ala Ser Gly Leu T
            315                 320                 325

Val Phe Ile Leu Arg Tyr Asn Gly His Pro Glu Glu Trp Thr Tyr T
            330                 335                 340

Leu Ile Ser Thr Gly Ala Lys Phe Leu Asn Val Ile Arg Asp Leu T
345                 350                 355                 360

Arg Pro Arg Leu Gly Ser His Gln Ile Glu Thr Asp Ile Ser Thr S
                365                 370                 375

Ser Glu Ser Pro Thr Thr Glu Thr Pro Arg Asn Ile His Ile Thr T
            380                 385                 390

Ala Arg Arg Tyr Leu Lys Val Ile Ile Gly Ile Ile Cys Val Ala G
        395                 400                 405

Ile Leu Leu Ile Val Ile Ser Ile Thr Cys Tyr Ile Arg Phe Arg H
        410                 415                 420

Met Arg Tyr Lys Pro Tyr Glu Asn Val Ile Pro Phe Pro Ala Val
425                 430                 435                 440

Thr Ser Ile Pro Ser Asn Asp Pro Asp Glu Leu Tyr Phe Glu Arg
                445                 450                 455

Ala Ser Asn Asp Glu Glu Ser Ala Asp Asp Ser Phe Asp Glu Ser
            460                 465                 470

Glu Glu Glu Pro Leu Asn Asn His His Ile Ser Thr Thr Gln His
        475                 480                 485

Asp Ile Asn Pro Glu Lys Ser Gly Ser Gly Tyr Ser Val Trp Phe
    490                 495                 500

Asp Thr Glu Asp Thr Ser Pro Gln Pro Leu His Ala Pro Pro Asp
505                 510                 515                 520

Ser Arg Val Val Lys Arg Leu Lys Ser Ile Leu Lys
                525                 530
```

RECOMBINANT POXVIRUS VACCINE AGAINST FELINE RHINOTRACHEITIS

This application is a continuation of application Ser. No. 08/096,183 filed on Jul. 26, 1993, now abandoned.

BACKGROUND OF THE INVENTION (1) Field of the Invention The present invention relates to a recombinant poxvirus vaccine against feline herpesvirus type 1 (FHV-1). In particular the present invention relates to a recombinant raccoon poxvirus containing genes encoding a gB and/or gD precursor polypeptide from FHV-1.

(2) Prior Art

Feline viral rhinotracheitis (FVR) is caused by feline herpesvirus-1 (FHV-1). Feline herpesvirus (FHV-1), is a member of the genus alphaherpes virinae. This widespread virus is responsible for 40–45% of all respiratory infections of Felidae (the cat family). Most cats receiving veterinary care are vaccinated against this disease. Several existing modified-live (MLV) and inactivated vaccines (IV) against the disease have either residual virulence (MLV) or suffer from a lack of immunogenicity. Furthermore, none of the existing parenterally administered MLV or IV can protect vaccinated cats from infection with virulent virus (as opposed to the disease) when exposed to it. This automatically leads to latent infections, which are epidemiologically very important because of the ease and frequency by which latent FHV-1 is reactivated and spread by asymptomatic, latently infected carriers.

Several million domesticated cats that are kept as house pets in the U.S. receive annual vaccinations for FVR. The need for an improved vaccine is substantial.

The superior immunogenicity typically achieved with other vaccinia-based recombinants (Blacklaws, B., et al., Virology 177:727–736 (1990)) is an indicator that recombinants could be more effective and safer vaccines than existing preparations.

It has been previously demonstrated that there is a significant host immune response to viral glycoproteins during FHV-1 infection (Maes, R., et al., J. Virology 51:259–262 (1984)). The temporal development of immunity against FHV-1 glycoproteins in cats inoculated with FHV-1 on the oral, nasal and conjunctival mucosa has also been defined. Thus, the concurrent detection of virus-neutralizing antibody and glycoprotein-specific immunoprecipitins implied that FHV-1 glycoproteins were important in the induction of virus-neutralizing antibodies to FHV-1 in cats (Burgener, D. and Maes, R., American J. Vet. Res. 49:1673–1676 (1988); and Rota, P., et al., Virology 154:168–179 (1986)).

Over the last ten years, a large amount of information has accumulated concerning the immunity induced by the glycoproteins of the alphaherpesviruses HSV-1, PRV, EHV-1, MDV and BHV-1 and other herpesviruses (i.e. EBV, HCMV, HVS). The genome of herpes simplex virus-type 1 (HSV-1) codes for at least 10 antigenically distinct glycoproteins: gB, gC, gD, gE, gG, gH, gI, gJ, gK and gL (Spear, P., Glycoproteins specified by herpes simplex viruses. In "The Herpesviruses" (B. Roizman, ED.) Vol. 3 pp 315–356. Plenum, N.Y. (1984); and Hutchinson, L., et al., J. Virology 66: 2240–2250 (1992)). It has been established that these glycoproteins can be classified as either essential or nonessential for replication of the virus. Because of their biological role in virion adsorption and eggression from infected cells, viral glycoproteins are generally conserved throughout related subfamilies. Based on extensive work with HSV-1 and the animal herpesviruses, it has been defined that glycoproteins B and D are major immunogens, eliciting high titers of virus neutralizing (VN) antibodies and providing protective immunity in vaccinated animals against lethal challenge. So far, HSV-1 is the best model for the comparison of the immune response induced by various glycoproteins of a specific herpesvirus (Blacklaw, B., et al., Virology 177:727–736 (1990)). Individual HSV-1 glycoproteins (gB, gD, gH, gI, gE and gG) expressed in vaccinia virus were evaluated for their ability to (1) elicit neutralizing antibody titers, (2) increase the rate of HSV-1 clearance and (3) protect against lethal challenge and latency. Vaccinia recombinants expressing gB and gD were reported to be superior in eliciting high titers of VN-antibodies and full protection from the establishment of latency.

Glycoprotein B homologs have been mapped within the genomes of 14 herpesviruses: herpes simplex virus-1, herpes simplex virus-2, varicella-zoster virus, Epstein-Barr virus, human cytomegalovirus, equine herpesvirus-1, equine herpesvirus-4, bovine herpesvirus-1, bovine herpesvirus-2, pseudorabies virus, Marek's disease virus, herpesvirus saimiri, infectious laryngotracheitis virus and simian agent type 8 virus. This conservation is not surprising since gB, as well as glycoproteins D, H, K and L, have been shown to be essential for production of enveloped viruses (Spear, P., Glycoproteins specified by herpes simplex viruses. In "The Herpesviruses" (B. Roizman, ED.) Vol. 3 pp 315–356. Plenum, N.Y. (1984); Hutchinson, L., et al., J. Virology 66: 2240–2250 (1992); and MacLean, C., et al., J. Gen. Virology 72: 897–906 (1991)).

HSV-1 gB and also the gB homolog of PRV (gII) have been shown to form a dimeric protein on the surface of virions and infected cells. Furthermore, glycoprotein B has been implicated in the penetration of the host cell membrane and also in cell-to-cell spread of virus by fusion. It appears that a homolog gB in FHV-1 acts in the same way.

Glycoprotein D of HSV-1 has also been reported to be essential for penetration of the nucleocapsid into susceptible cells (Fuller and Spear, J. of Virology 55:475–482 (1985); Spear et al., Herpes simplex virus:pathway of entry into cells. In "Cell Biology of Virus Entry, Replication and Pathogenesis" pp. 163–175 (1989); Johnson et al., J. of Virology 64: 2569–2576 (1990)). Although genes encoding gD homologs are generally conserved throughout herpesvirinae, VZV and the distal related herpesvirus, channel catfish herpesvirus do not contain gD homologs (Davison, A. and Scott, J., J. Gen. Virology 67: 1759–1816 (1986); Davison, A., Virology 186: 9–14 (1992)). Early studies with monospecific gD antisera or monoclonal antibodies have indicated that gD plays a role in virus penetration and cell fusion (Noble, A., et al., Virology 129: 218–224 (1983)). In one study by (Johnson, D., et al., J. of Virology 62: 4605–4612 (1988)) UV-inactivated (gD+) virions were reported to block the entry of WT-HSV-1 or HSV-2 into cells, whereas UV-inactivated virions which are phenotypically gD- were unable to block WT-HSV-1 or HSV-2 entry. Furthermore, mutant (gD-) virions were shown to be able to adsorb to cellular membranes but could not penetrate into the cells.

Besides their biological significance, these two glycoproteins are the major immunodominant polypeptides of herpesviruses, capable of the induction of protective immunity. Of all the HSV-1 glycoproteins, only antibodies to glycoprotein D and B can crossreact with the two types of simplex viruses (Marchioli, C., et al., J. of Virology 61: 3977–3982 (1987)). It has also been demonstrated that gD of HSV-1 induces the most potent monoclonal antibodies with the highest affinity for the HSV-1 virion (Para, M., et al., J.

of Virology 55: 483–487 (1985); Iglesias, G., et al., Vet. Micro. 24: 1–10 (1990)). Furthermore, anti-gD monoclonal antibodies have been routinely generated from animals immunized with crude virion preps of HSV-1.

There is good evidence that glycoprotein B is as important an immunogen as gD. In HCMV seropositive individuals, for example, 40–70% of total virus-neutralizing activity in serum has been reported to be directed against gB (Britt, W., et al., J. of Virology 64: 1079–1085 (1990)). Such a preferential reactivity of human sera for a single virion component is unique, due to the fact herpesviruses contain many glycoproteins.

Both glycoproteins D and B of HSV-1, PRV and EHV-1 have been reported to protect mice from lethal challenge (Long, D., et al., Infection and Immunity 37:761–763 (1984)). In one study, mice immunized with gD, affinity-purified from cells infected with either HSV-1 or HSV-2, were protected from a lethal intraperitoneal (i.p) challenge by virus of either serotype (Eisenberg, R., et al., J. of Virology 56: 1014–1017 (1985)). Similarly, gp50 of pseudorabies virus, the gD homolog in the suid herpesvirus, has been reported to elicit VN-antibodies (Eloit, M., et al., J. of Gen. Virology 71:2425–2431 (1990)) and when expressed in vaccinia virus or Chinese hamster ovary cells, (Marchioli, C., et al. J. of Virology 61: 3977–3982 (1987)) protected immunized mice or rabbits from virulent challenge with PRV. In addition, a recombinant gp50 protects pigs, the natural host, from lethal challenge (Marchioli, C., et al. J. of Virology 61: 3977–3982 (1987); Riviere, M., et al., J. of Virology 66: 3424–3433 (1992)). Likewise, protection of mice immunized with recombinant adenoviruses expressing glycoprotein B of HSV-1, has also been demonstrated. Unlike in gD, correct glycosylation of gB appears to be essential for optimal immunogenicity. Mice immunized with recombinant gB isolated from mammalian cells, produced significantly higher titers of virus-neutralizing antibodies, when compared to animals immunized with recombinant gB isolate from procaryotes. An enhanced level of protection from lethal challenge was also demonstrated in vaccinates receiving the glycosylated (eukaryotic) recombinant polypeptide. In a study by van Drunen littel-van den Hurk, S., et al., J. of Gen. Virology 71: 2053–2063 (1990)), deglycoslyation of gI(gB) of BHV-1 resulted in a significant decrease in the production of serum neutralizing antibodies, due to modifications of three distinct carbohydrate containing continuous epitopes. Likewise, nonglycosylated HCMV gB produced in recombinant prokaryotic systems has been reported to be less immunogenic than the glycosylated protein produced in eukaryotes (Britt, W., et al., J. of Virology 64: 1079–1085 (1990)). In contrast, nonglycosylated forms of glycoprotein D, for example gIV of BHV-1, stimulate neutralizing antibodies at levels similar to those elicited by glycosylated forms. This comes as no surprise, since the nucleotide sequence of gp50 (gD) of PRV lacks potential N-linked glycosylation sites (Petrovskis, E., et al., J. of Virology 59: 216–223 (1986)). Recently, gD of HSV-1 has been expressed at high levels in baculoviruses. Although the recombinant protein was slightly smaller than the gD in HSV-1 infected Vero cells, due to differences in the glycosylation pattern of the two cell lines, the expressed protein was present on the membranes of SF9 cells and reacted with gD specific antibodies. Vaccination with the expressed protein resulted in the production of neutralizing antibodies to HSV-1 and complete protection against lethal HSV-1 challenge (Ghiasi, H., et al., Arch. Virology 121: 163–177 (1991)).

Because of these results, gD and gB of HSV-1 are the prime candidates for a subunit vaccines. The genes encoding gD and gB of various herpesviruses have been expressed in both prokaryotic and mammalian cells. Studies on mammalian cells expressing native and truncated gD polypeptides, along with synthetic peptides and V8 protease digestion products have enabled researchers to map its immunologically important continuous and discontinuous epitopes. Synthetic peptides representing one continuous epitope (amino acids 9–21) of gD(HSV-1) conjugated to ovalbumin or BSA, were reported to elicit high titers of antipeptide neutralizing antibodies in mice after immunization with adjuvants. Resistance to lethal challenge was also demonstrated in synthetic peptide-immunized mice (Eisenberg, R., et al., J. of Virology 56: 1014–1017 (1985)).

From the above, it is clear that humoral immunity to gD and gB appears to be a significant contributor to the clearance of the virus. However, this type of immunity is primarily important during the initial infection. Overall, cell-mediated immunity (CMI) appears to be more important. Not only is it essential in the acute phase of a herpesvirus infection but is also involved in virus clearance following reactivation or reinfection. The importance of CMI in resistance to HSV-1 is apparent by the fact that 80–90% of immunosuppressed patients have a high incidence of recurrence (Bernstein, D., et al., J. of Immunology 146:3571–3577 (1991)). Supporting the role of cell-mediated immunity are numerous reports of adoptive transfer experiments, conferring resistance to lethal HSV challenge. In a study by (Rooney, J., et al., J. of Virology 62: 1530–1534 (1988)), vaccinia recombinants containing the gD(HSV-1) gene under the control of an early vaccinia promoter were reported to elicit a better T-cell response than recombinants in which gD expression is controlled by a late vaccinia promoter. Both recombinant viruses produced potent neutralizing antibodies and protected immunized mice from both lethal HSV-1 challenge and latency establishment by the challenge virus for at least 6 weeks after immunization (Rooney, J., et al., J. of Virology 62: 1530–1534 (1988); Wachsman, M., et al., J. Gen. Virology 70:2513–2520 (1989); Wachsman, M., et al., J. of Inf. Dis. 159: 625–634 (1989)). However, reimmunization with the recombinants containing the early vaccinia promoter/gD construct resulted in a significant increase in neutralizing antibody titers lasting over 1 year. Vaccinia recombinants containing the late vaccinia promoter/gD gene fusion failed to protect from cutaneous disease following administration of a high dose of HSV-1. Protection against cutaneous lesions is associated with the induction of HSV-1 specific T-cell responses. Furthermore, proliferation of lymph node cells in response to HSV-1 antigens was demonstrated only in mice immunized with the Vac(early promoter)/gD- and not Vac(late promoter)/gD-constructs. It appears that temporal expression of glycoprotein genes in antigen presenting cells is important in the induction of immunity to herpes viral disease (Wachsman, M., et al., (1989)).

Additional evidence for the role of these glycoproteins in cell-mediated immunity response comes from studies involving immunized mice transplanted with cells expressing herpesvirus glycoproteins. Nakagama, H., et al., FASEB J. 5: 104–108 (1991) reported significant differences in lymphocyte infiltration and antigen clearance in syngeneic unimmunized mice, transplanted with (HSV-1) gD-transfected BALB/3T3 cells, as compared to mice immunized with HSV-1. In the later case, the transfected cells elicited massive lymphocyte infiltration of mainly THY1+ and CD8+ lymphocytes along with a small number of CD5+, CD4+, and B-lymphocytes in the HSV-1− immunized mice. In contrast, in unimmunized mice, little evidence of cellular infiltration could be detected and transplanted cells could be detected for as long as 7 days. In immunized animals however, the transplanted cells were mostly destroyed by day 4, despite the presence of anti-HSV-1 antibodies at the time of transplantation. Likewise, cells from the spleen and lymph nodes of gB-immunized mice have been reported to protect syngeneic mice against lethal challenge.

It is generally believed that reactivation of latent herpesvirus occurs more frequently than episodes of recurrent disease. Administration of gD or gB to latently infected animals, reduces the frequency of reactivation, the severity of recurrent disease and the duration of shedding (Bernstein, D., et al., J. of Immunology 146: 3571–3577 (1991)). In guinea pigs latently infected with HSV-2, the adoptive transfer of clones expressing either glycoprotein D or B, significantly reduced the number and severity of subsequent symptomatic recurrent infections with a concomitant reduction in cervicovaginal HSV-2 shedding. In this study the author concluded that the reduction in clinical disease was the result of lymphokine activated cellular immunity in which the transfer of HSV-1 gD or gB into latently infected animals resulted in the production of other cytokines by HSV-1 sensitized T-cells. This could further increase critical responses, such as natural killer cells, needed for the clearance of the reactivated virus. Further evidence for the involvement of lymphokine activity in CMI elicited by herpesvirus glycoproteins was provided by (Zarling, J., et al., J. of Immunology 136: 4669–4673 (1986)). Administration of gD or gB, expressed in mammalian cells to HSV-1 seropositive individuals stimulated proliferation of their peripheral blood lymphocytes and interleukin-2 production by these cells. Interestingly, IL-2 can also significantly enhance cellular and humoral immunity in cows when included in either a gD subunit or MLV-vaccine (Reddy, P., et al., Vet. Immuno. Immunopath. 23: 62–74 (1989); Hughes, H., et al., Immunology 74:461–466 (1991)). Likewise, high antibody responses and cell mediated immunity to HSV-1 were recently reported in mice immunized with a recombinant expressing a glycoprotein D/Interleukin-2 fusion protein (Hinuma, S., et al., FEBS 288, 138–142 (1991)).

Objects

It is an object of the present invention to provide an approach for vaccination of cats against feline herpesvirus type 1 (FHV-1) using a recombinant vaccine that corrects the shortcomings of currently available commercial vaccines which lack immunogenicity, have an inability to prevent infection, have adjuvant induced side effects, have a potential reversion to virulence, or have a residual virulence.

It is further an object of the present invention to provide the recombinant viral vaccines expressing a single FHV-1 viral glycoprotein or two (2) glycoproteins.

It is further an object to provide novel live recombinant vaccines which express gB and gD of FHV-1 in a recombinant poxvirus vector that is safe for use in cats and which provides immunogenicity in cats.

It is particularly an object to provide recombinant raccoon poxviruses expressing the FHV-1 gB and/or gD genes.

Further, it is an object to immunize cats with recombinant raccoon poxviruses, which when exposed to virulent FHV-1, provide superior protection against clinical signs and shedding of the virulent virus.

These and other objects will become increasingly apparent by reference to the following description and the drawings.

BRIEF DESCRIPTION OF THE DRAWINGS

FIGS. 1A and 1B show the results of low stringency hybridization experiments with HSV-1 (gB)-specific probes and blotted FHV-1 DNA. (FIG. 1A) the position of the XhoI-NcoI restriction sites within the genes encoding HSV-1 gB. (FIG. 1B) Southern blots containing restriction digested DNA isolated from a recombinant clone containing SalI fragment G (lanes 1–2) and FHV-1 infected CRFk's (lanes 3–12. Prior to electrophoresis the DNA was digested with the following restriction endonucleases: HindIII (lane 1) SalI (lane 2), BamHI (lane 3), EcoRI (lane 4), HindIII (lane 5), KpnI (lane 6), NcoI (lane 7), PstI (lane 8), XhoI (lane 9), XbaI (lane 10), SacI (lane 11) and EcoRV (lane 12).

FIGS. 2A, 2B and 2C show the genomic organization of the FHV-1 including the glycoprotein B gene. FIG. 2A shows the 134 Kb genome is represented as two unique sequences ($U_L$ and $U_S$) and two inverted repeat sequences ($IR_S$ and $TR_S$) flanking the $U_S$ region. FIG. 2B shows the SalI restriction map of FHV-1 (C-27) and a detailed restriction map of the 9.6 Kb SalI G fragment. Arrows indicate the location of the gB and ICP18.5 ORFs within the region sequenced. FIG. 2C shows the black boxes represent the gB-specific hybridization probes used to map the gB transcript.

FIGS. 3A and 3B show the nucleotide sequence and predicted amino acid sequence of the FHV-1 gB polypeptide and part of the FHV-1 gene product analogous to ICP18.5. Putative CAT (ATTG), TATA (AATATATC) boxes and poly (A) signal sequence (AATAAA) are shown in bold. Potential N-glycosylation sites are bracketed by two lines and the predicted hydrophobic N-terminal signal peptide and C-terminal transmembrane domain are overlined. Potential proteolytic cleavage recognition sites are indicated with asterisks.

FIGS. 4A and 4B show analyses of FHV-1 B polypeptides. FIG. 4A shows lysates from FHV-1 infected cells (lanes 1 and 4), lysates from FHV-1 virions (lanes 2 and 5) and lysates from mock-infected cells (lanes 3 and 6) were immunoprecipitated with monospecific polyclonal HSV-1 gB specific antisera R69 (lanes 1–3) and anti-gB1 (lanes 4–6). FIG. 4B shows the results of lysates from FHV-1 virions electroblotted onto nitrocellulose and probed with R69 (lane 1) and anti-gB1 (lane 2).

FIG. 5 shows hydrophilicity plot of the predicted gB protein. The hydropathy value was calculated by the methods of Kyte and Doolittle (Kyte, J. and Doolittle, R., J. of Molecular Biology 157:105–131 (1982)). The hydropathy window was seven amino acids, with a plus sign indicating increasing hydrophilicity and a minus sign representing increasing hydrophobicity.

FIG. 6 shows northern blot analysis of RNA extracted from FHV-1 infected CRFK cells. Total cytoplasmic RNA was isolated from uninfected and FHV-1 infected cells. The RNA was fractionated in an agarose-formaldehyde gel, transferred to nitrocellulose paper and hybridized with $^{32}P$-labeled probes (FIG. 1C). Lanes: 1–4, RNA extracted from FHV-1 infected cells; 5, RNA extracted from uninfected cells. The blots in lanes 1, 2, 3 and 4 were hybridized with $^{32}P$-labeled fragment A (SalI-EcoRI, 4.0 Kb), B (EcoRI-KpnI, 1.6 Kb), C (BamHI-EcoRI, 3.0 Kb) and D (KpnI-EcoRI, 3.1 Kb), respectively. The blot in lane 5 was hybridized with the 9.6 Kb SalI G fragment.

FIG. 7 show the evolutionary relatedness of FHV-1 to eleven other alphaherpesviruses. Amino acid sequences of glycoprotein B, the most conserved glycoprotein in all subfamilies of herpesvirinae, were analyzed for homology and aligned using the GAP and PILEUP programs of the University of Wisconsin (UWGCG) (Devereux, J., and Grinyer, I., Nucleic Acid Research 12: 387–395 (1984)). Dendrograms were drawn using the Phylogeny Interference Package (PHYLIP) (Felsenstein, J., Evolution 39: 783–791 (1985)).

FIGS. 8A, 8B, 8C, and 8D show the genomic organization of the FHV-1 unique short genes encoding a putative protein kinase and glycoproteins gG, gD, gI, and gE. FIG. 8A shows the 134 Kb genome is represented as two unique sequences ($U_L$ and $U_S$) and two inverted repeat sequences ($IR_S$ and $TR_S$) flanking the $U_S$ region. FIG. 8B shows the SalI and EcoRI restriction maps of FHV-1 (C-27). FIG. 8C shows a detailed restriction map of the unique short region along with the positions and transcriptional directions of the genes encoding the putative Pk, gG, gD, gI and gE. FIG. 8D shows the black boxes (1–6) representing the hybridization probes used to map the $U_S$ transcripts.

Figure 9A:
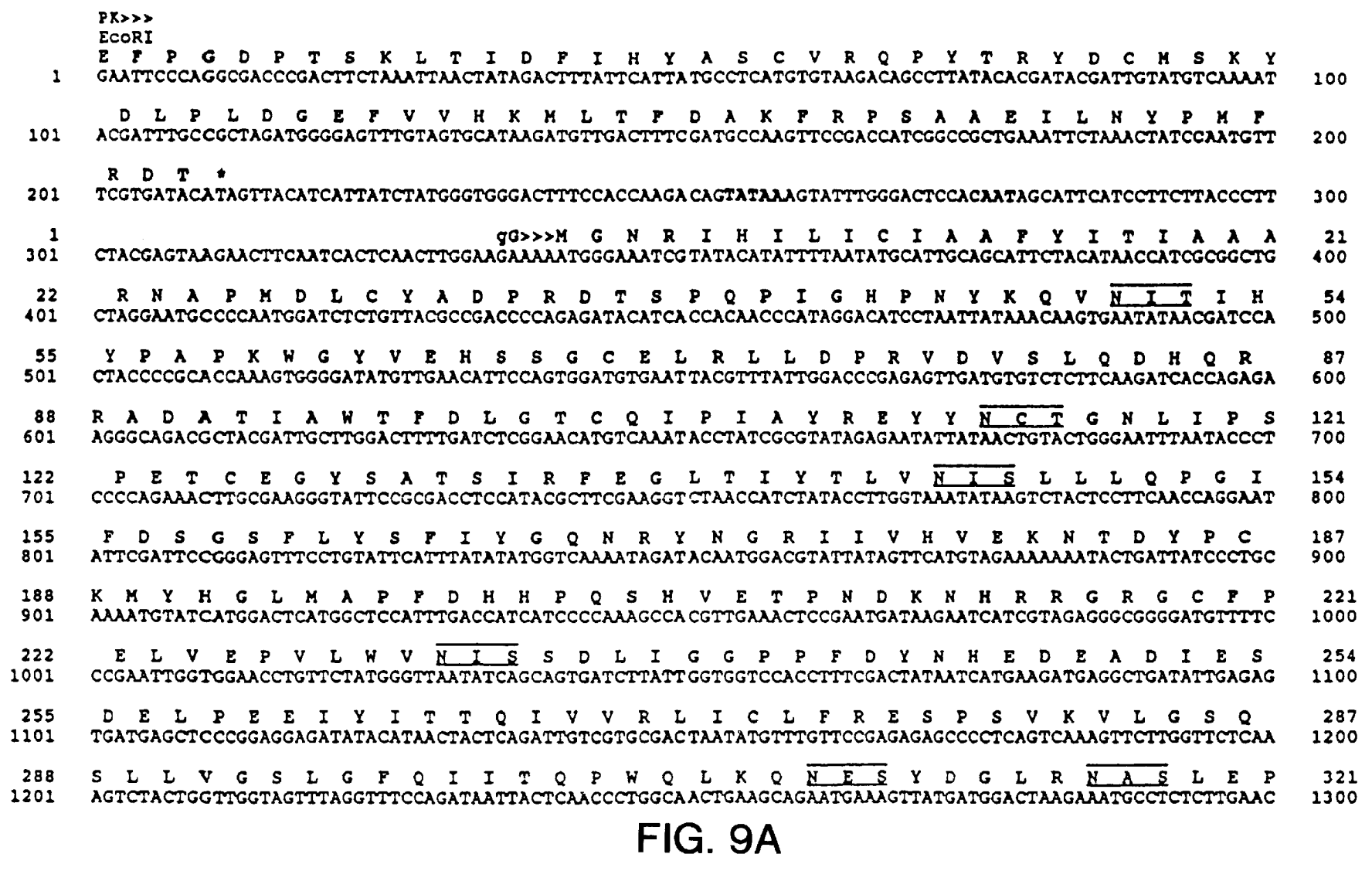
Figure 9B:
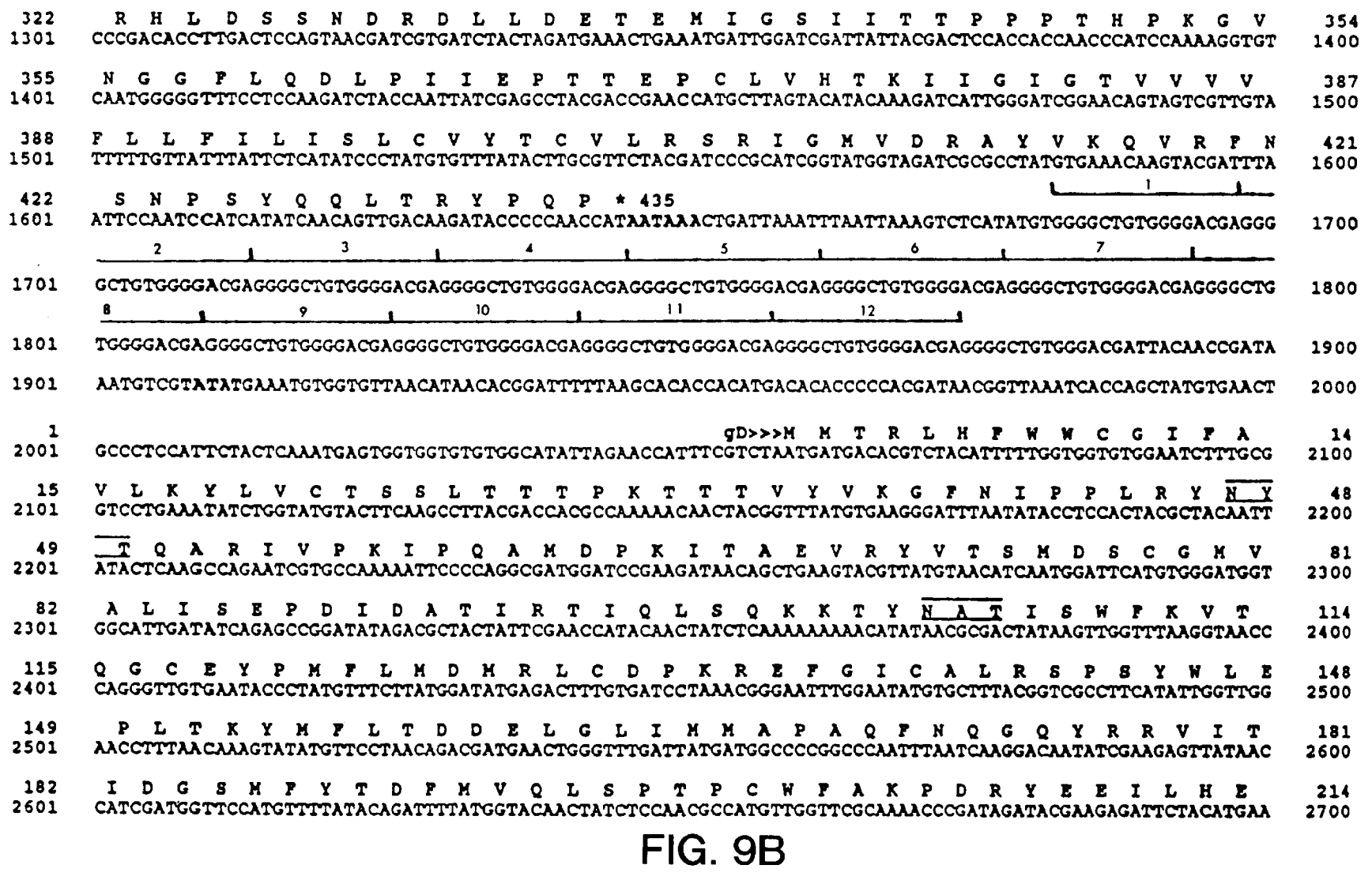
Figure 9C:
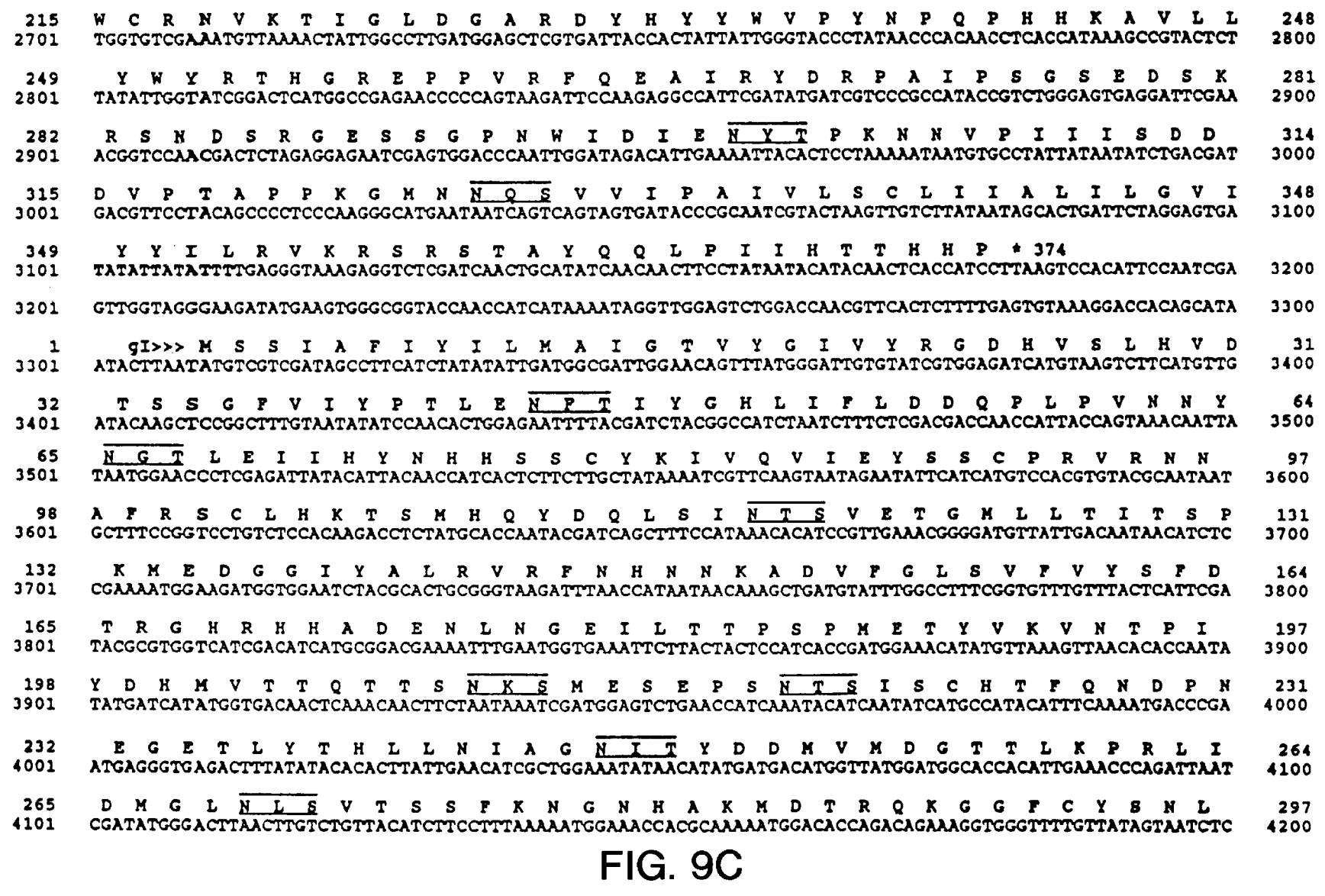
Figure 9D:
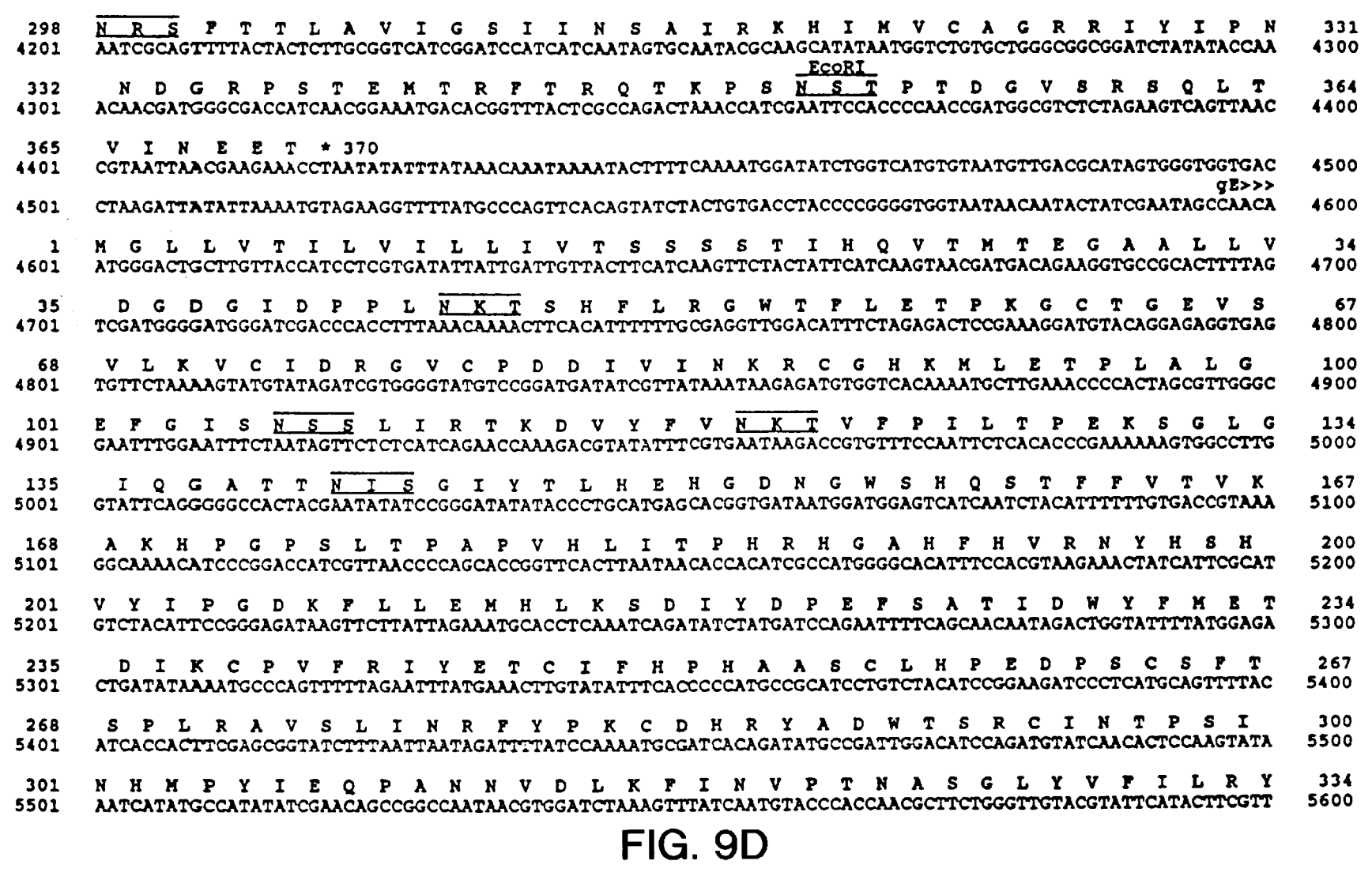
Figure 9E:
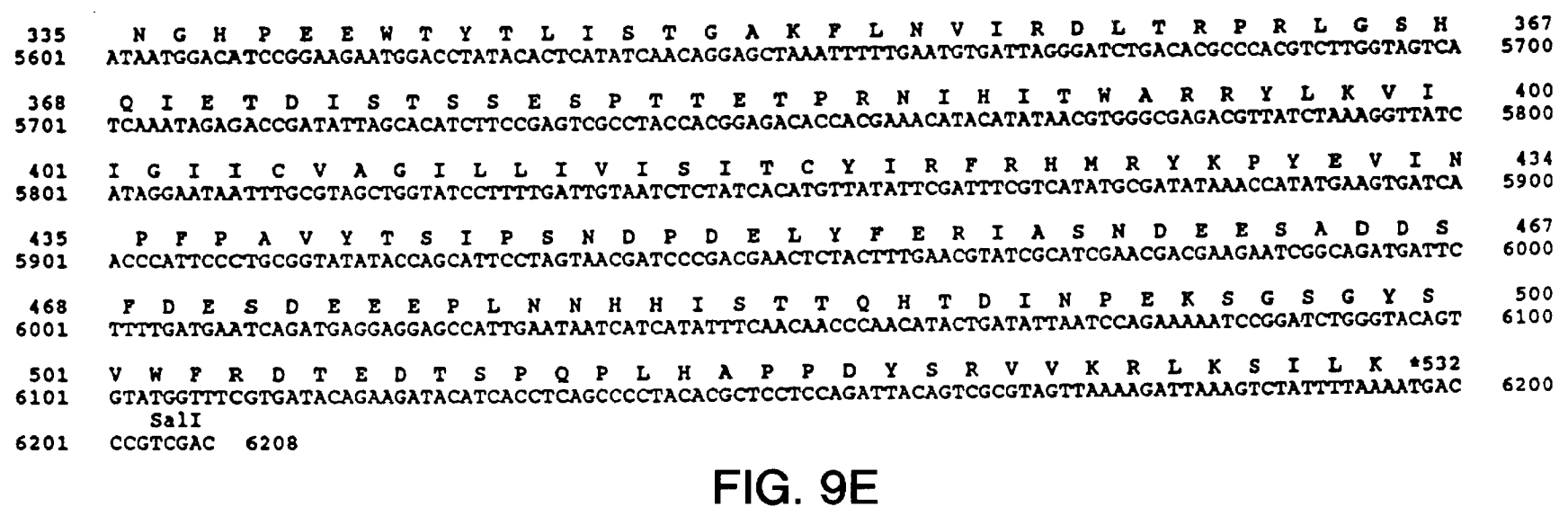

FIGS. 9A to 9E show the nucleotide sequence and predicted amino acid sequences of the FHV-1 polypeptides, gG, gD, gI and gE and part of the putative threonine/serine protein kinase. Cis-acting sites (CAAT, TATA) boxes and polyadenylation sites are shown in bold. Potential N-linked glycosylation sites are bracketed by two lines. Direct repeats of the sequence GGG GCT GTG GGG ACG A are indicated with a partitionary line.

FIG. 10 shows hydrophilicity plot of the predicted gD protein. The hydropathy value was calculated by the methods of Kyte and Doolittle (Kyte, J. and Doolittle, R., J. of Molecular Biology 157:105–131 (1982)). The hydropathy window was nine amino acids, with a plus sign indicating increasing hydrophobicity and a minus sign representing increasing hydrophilicity.

FIG. 11 shows northern blot analyses of RNA extracted from FHV-1 infected CRFK cells and hybridized with probes representative of the $U_S$glycoprotein genes. Total cytoplasmic RNA isolated from FHV-1 infected cells was separated in agarose/formaldehyde as described in methods. Strips blots were hybridized with radiolabeled restriction fragments as depicted in FIG. 8,D. Blots 1–6 were probed with the following restriction fragments: Blot 1, 0.16 Kb TaqI-TaqI (gG-specific), Blot 2, 2.3 Kb EcoRI-EcoRV (Pk/gG/gD-specific), Blot 3, 0.42 Kb RsaI-RsaI (gD-specific), Blot 4, 2.0 Kb EcoRV-EcoRI (gD/gI-specific), Blot 5, 0.85 Kb XhoI-EcoRI (gI-specific) and Blot 6, 1.8 Kb EcoRI-SalI (gI/gE specific).

FIGS. 12A and 12B show the results of the PCR-amplified gB and gD products. Presented are a photographs of an EtBr-stained agarose gel containing electrophoretically separated fragments from the amplification of 1.14 Kb gD and 2.8 Kb gB: (FIG. 12A) lanes 1–3 and (FIG. 12B) lanes 1–3, respectively. Molecular weight standards are in lanes 4 (A and B).

FIGS. 13A and 13B show restriction analysis of the gD PCR-product. (FIG. 13A) Computer-predicted restriction maps based on nucleotide sequencing of the gD gene. (FIG. 13B) Visualization of an agarose gel containing restriction endonuclease digested PCR-products. Prior to electrophoresis, these products were digested with the following enzymes: BamHI (lane 1), EcoRI (lane 2), ClaI (lane 3), SacI (lane 4) and KpnI (lane 5).

FIGS. 14A and 14B show the constructs of the recombinants plasmids pKGgD and pKGgB. Recombinants were generated via cloning restriction digested PCR-amplified products into the donor plasmid pKG19. Relative restriction sites are indicated along with the molecular size of each construct.

FIG. 15 shows the results of restriction analysis of the recombinant plasmid, pKGgD. Visualization of an EtBr-stained agarose gel containing digested recombinant plasmid, pKGgD. Prior to electrophoresis, the recombinant DNA was digested with restriction endonucleases XhoI and EcoRI (lanes 1–6; MW standard, lane 7).

FIGS. 16A and 16D show the results of restriction analysis of the recombinant donor plasmids, pKGgB and pKGrgB. Restriction endonuclease analyses of the PCR-amplified FHV-1 gB gene cloned into the donor plasmid pKG19. Recombinant plasmid (FIGS. 16A, 16C) pKGgB, contained an insert in the correct orientation with respect to the Vac $P_{7.5}$ promoter. The control plasmid (FIGS. 16B, 16D) pKGrgB, contained and inverted insert. Computer-generated restriction maps of the recombinant plasmids are shown with photographs of an EtBr-stained agarose gel containing electrophoretically separated fragments of the constructs.

FIGS. 17A, 17B, 17C, 17D, 17E and 17F show the results of the indirect fluorescence antibody assay of gB and gD synthesized in vaccinia or raccoon poxviruses infected Rat-2 cells. Photographs (FIGS. 17A–C) represent cells infected with Vaccinia virus and then transfected with DNA from plasmids; pKggB (FIG. 17A), pKGgD (FIG. 17B) and pKGrgB (FIG. 17C). Photographs (FIGS. 17D–F) represent cells infected with Raccoon poxvirus and then transfected with pKGgB (FIG. 17D), pKGgD (FIG. 17E),and pKGrgB (FIG. 17F). Fixed cells were treated with a rabbit anti-FHV-1 antibody, followed by a fluorescein isothiocyanate conjugated goat anti-rabbit antibody. The magnification was 250×.

FIG. 18 shows the results of western blot analyses of FHV-1 polypeptides with rabbit antisera against the vaccinia recombinants VVgB and VVgD. Denatured purified virions were separated using SDS-PAGE and electrophoretically transferred to Nytran. Rabbit anti-VVgB and anti-VVgD sera were used to probe blots A and B, respectively. A rabbit anti-FHV-1 sera was used to probe blot C. Mouse anti-rabbit alkaline phosphatase labelled conjugates were used as the report antibody.

DESCRIPTION OF PREFERRED EMBODIMENTS

Figure 1A:
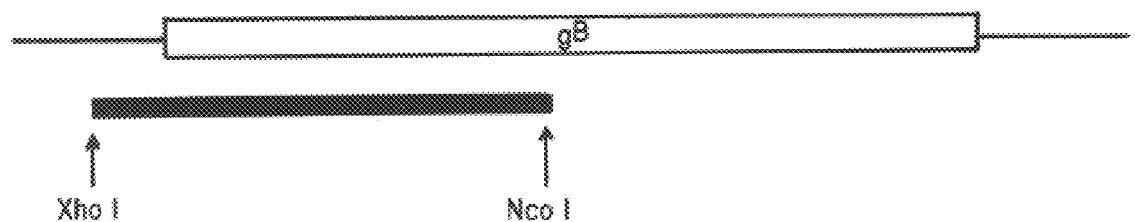

The present invention relates to a recombinant poxvirus containing foreign genes from a feline herpesvirus encoding a glycoprotein selected from the group consisting of gB as set forth in Seq ID NO:1, gD as set forth in Seq ID NO:2 and mixtures thereof which are exp Further still, the present invention relates to a method for producing a synthetic gene encoding a gB precursor polypeptide as set forth in Seq ID NO:1 which comprises: amplifying the FHV-1 DNA using PCR with oligonucleotides containing XhoI recognition sequences; providing a purified and isolated DNA encoding a gB precursor polypeptide with two XhoI DNA recognition sequences; digesting the amplified DNA with XhoI to produce the synthetic gene; and cloning the synthetic gene into the donor plasmid, pKG19.

Further still, the present invention relates to a method for producing a synthetic gene encoding a gD precursor polypeptide as set forth in Seq ID NO: 2 which comprises: amplifying the FHV-1 DNA using PCR with oligonucleotides containing XhoI and EcoRI recognition sequences; digesting the amplified DNA with XhoI and EcoRI to produce the synthetic gene; and cloning the synthetic gene into the donor plasmid, pKG19.

Finally, the present invention relates to a vaccine which comprises: a recombinant poxvirus containing foreign genes from a feline herpesvirus encoding a glycoprotein precursor polypeptide selected from the group consisting of a gB precursor polypeptide as set forth in Seq ID NO:1, a gD precursor polypeptide as set forth in Seq ID NO:2 and mixtures thereof which are expressed by the poxvirus. The DNA sequences for the precursor polypeptides are shown in FIGS. 3 and 9.

The vaccine is intended to be given orally, intranasally or intramuscularly. Oral and intradermal administration of the vaccine is preferred due to stimulation of local immunity. However, subcutaneous (SC) injections are recommended for cats from multiple cat households since the virus is contained within the tissue of the cat and thus is not likely to be shed.

The vaccine preferably contains between about $10^5$ and $10^7$ PFU of the poxvirus per dosage unit. Higher or lower amounts can be used depending upon the antigenicity of the vaccine.

The raccoon poxvirus is the preferred vector for the FHV-1 gB and gD DNA. Another vector which can be used is vaccinia virus.

HSV-1 gB and gD and have been identified and both genes encoding the polypeptide precursors have been completely sequenced (McGeoch, D., et al., J. Mol. Biol. 181:1–13 (1985); McGeoch, D., et al., J. Gen. Virology 69:1531–1551 (1988)). There is clear evidence that HSV-1 gB and gD induce both humoral antibodies and CMI (cell mediated immunity) responses.

Figure 3A:
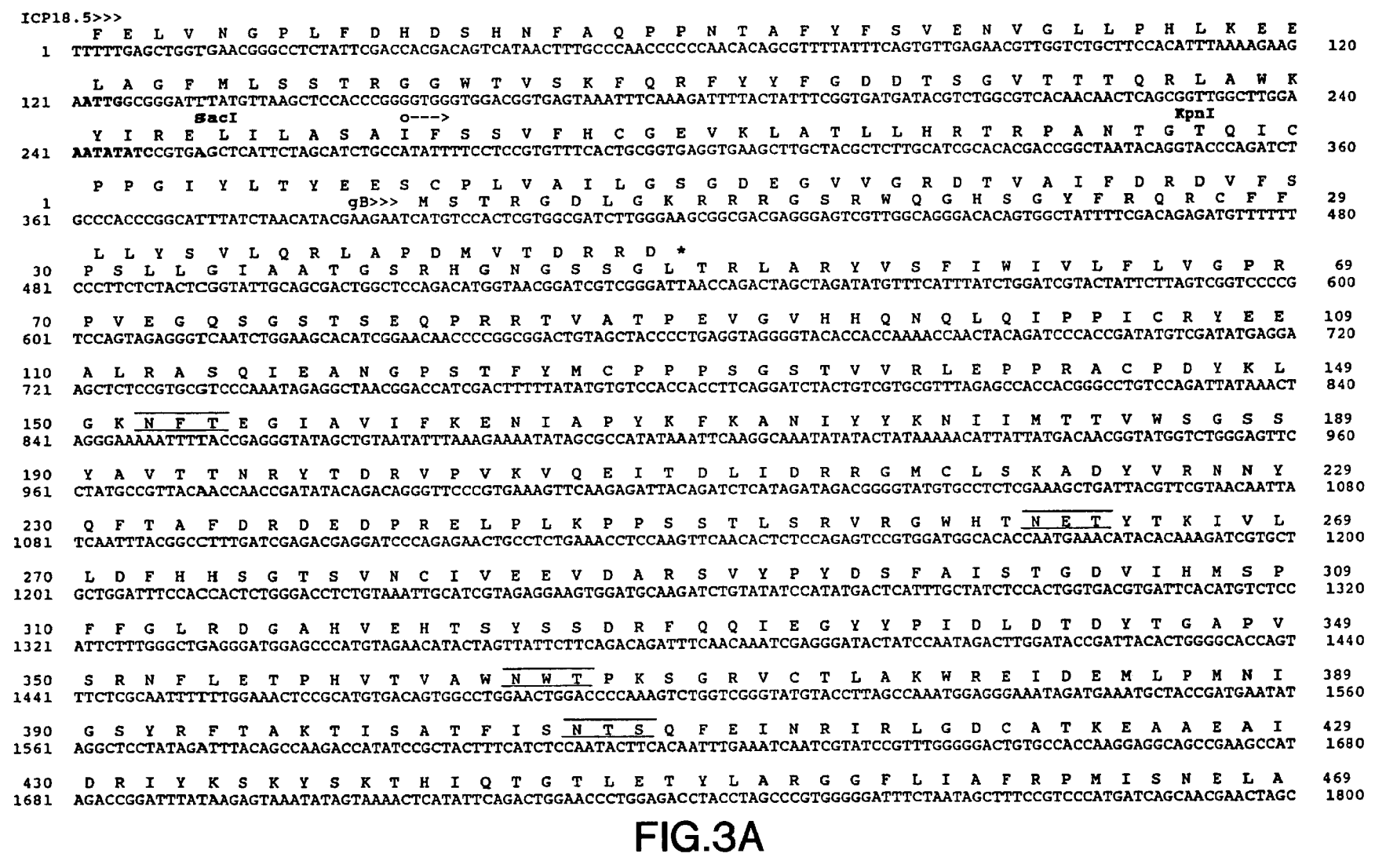
Figure 3B:
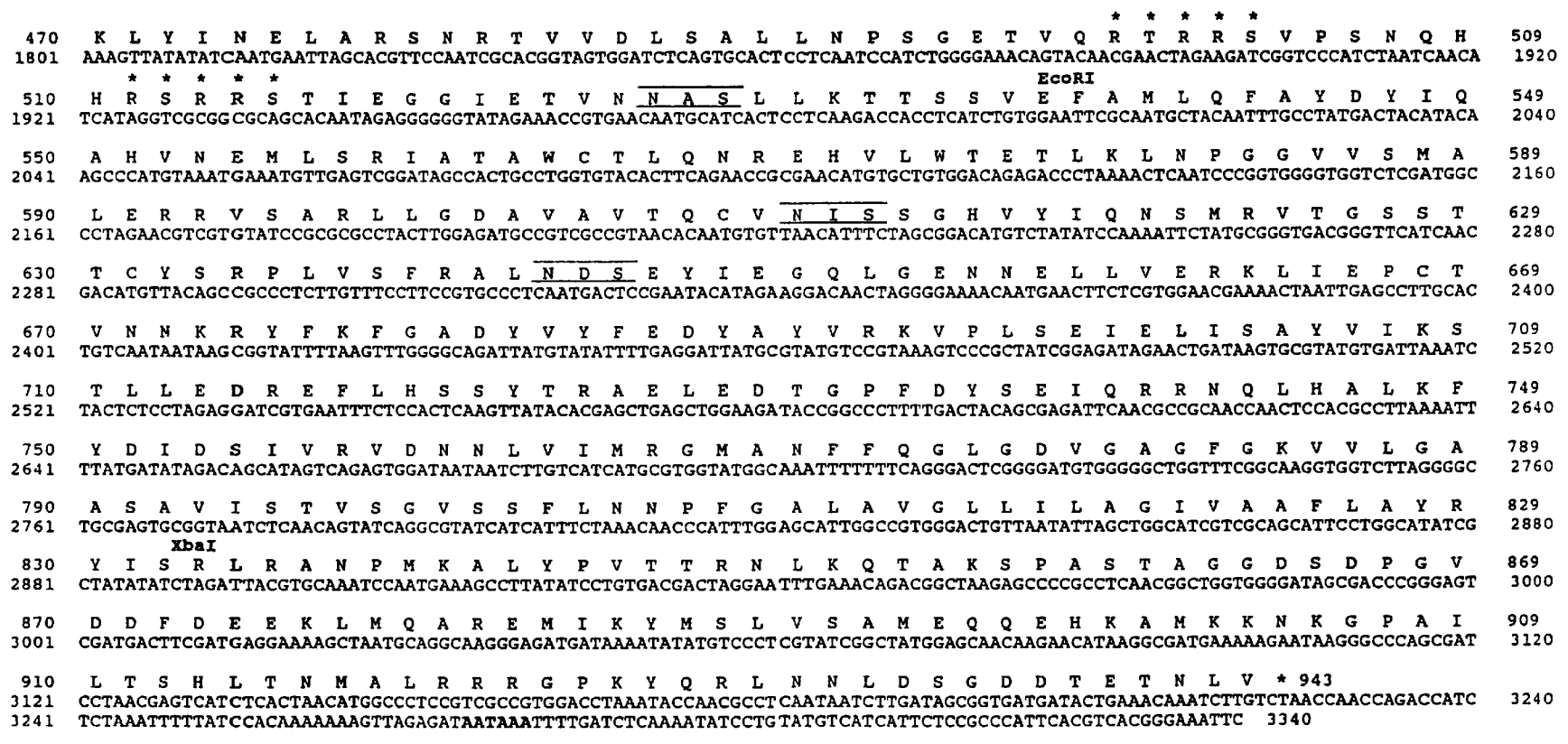

Like other alphaherpesviruses, FHV-1 contains homologs to glycoproteins B (gB) and D (gD) of HSV-1. In this invention, HSV-1 gB monospecific antisera reacted positively with three FHV-1 proteins (100, 64 and 58 Kd) from virion lysates using immunoprecipitation and immunoblot analyses. Reduced stringency hybridization experiments using a HSV-1 gB probe localized the FHV-1 gB gene to a 9.6 Kb SalI fragment in the unique long region of the genome. Northern analyses further localized the entire coding region within a 3.3 Kd SacI subfragment. This fragment was sequenced and analyzed for open reading frames as shown in FIGS. 3A and 3B. The predicted amino acid sequence of the 2,829 bp. ORF was shown to have a high degree of homology with gB analogs of HSV-1, EHV-1, BHV-1, EHV-4, and especially PRV. Two proteolytic cleavage sites RTRRS and RSRRS were also present in the predicted translation product. An evolutionary tree based on gB homologs from 12 alphaherpesviruses suggest Feline herpesvirus-1 evolved along similar lines as equine herpesvirus and pseudorabies.

In this intention, the gene encoding the feline herpesvirus type 1 glycoprotein D precursor polypeptide was identified by nucleotide sequencing a 6.2 Kb portion of the unique short region of FHV-1. Analyses of this sequence has revealed 5 open reading frames capable of encoding homologs to HSV-1 protein kinase and glycoproteins gG, gD, gI and gE. Hydropathic analysis of the predicted amino acid translation product from the gD gene of FHV-1 has shown that FHV-1 glycoprotein D exhibits features typical of a membrane-bound glycoprotein: a hydrophobic signal sequence at the amino-terminus, four potential N-linked glycosylation sites and a hydrophobic transmembrane domain near the carboxyl-terminus. The predicted translation product of the gD gene was also shown to have a high degree of homology with gD analogs of related alphaherpesviruses of the genus Varicellovirus. Northern analysis of RNA isolated from FHV-1 infected cells has indicated the presence of two gD transcripts. $^{32}$P-labelled DNA probes specific for the gD gene detected two major transcripts of 3.5 and 1.8 kilobases. It is proposed that the 1.8 Kb transcript represents the monocistronic transcripts encoding the gD precursor polypeptide. The larger 3.5 Kb transcript represents an overlapping transcript originating at the gD promoter and terminating at the polyadenylation site of the downstream gene. This transcriptional pattern is in agreement with the fact that no polyadenylation site was found immediately 3' of the gD open reading frame.

In this invention, glycoproteins B and D of FHV-1 were expressed in raccoon poxviruses and vaccinia viruses generating live vaccines against feline rhinotracheitis. To accomplish this, the FHV-1 gB and gD genes were amplified using PCR, digested with the appropriate restriction endonucleases and cloned into a donor plasmid containing the right and left termini of the vaccinia thymidine kinase gene. Rescue of these constructs into the genome of either raccoon or vaccinia poxviruses generated recombinants that reacted with rabbit anti-FHV-1 serum in an indirect fluorescent antibody test. High titers of virus neutralizing antibodies were generated in rabbits inoculated with vaccinia recombinants expressing either FHV-1 gB or gD. Antisera against the vaccinia recombinants reacted with their respective polypeptides (60 Kd, gB and 50 Kd, gD) on western blots containing FHV-1 viral polypeptides.

EXAMPLE 1

The aim of this example was to immunologically define the existence of an FHV-1 gB homolog, to map its genomic location and to define its nucleotide sequence. To accomplish this radiolabeled plasmids containing the 5' terminus of the HSV-1 gB gene were used to probe southern blots containing cloned fragment of FHV-1 DNA. The coding region of the FHV-1 gB homolog was localized within a 3.3 Kb SacI fragment in the unique long region of the FHV-1 genome. Two different rabbit antisera to HSV-1 gB reacted strongly with a 64 and 58 Kd and more faintly with a 100 Kd FHV-1 protein from virion lysates in immunoprecipitation and western blot analyses. The nucleotide sequence of FHV-1 gB is described along with immunoblot and immunoprecipitation analyses of FHV-1 polypeptides crossreacting with anti-HSV-1 gB antisera.

Material and Methods

Bacterial strains and vectors

*Escherichia coli* JM101 and JM109 available upon request from Michigan State University, East Lansing, Mich. were grown in LB medium and used to propagate pBluescript-KS (Stratagene, La Jolla, Calif.) and M13, series mp18 and mp19 (BRL, Gaithersburg, Md.).

Viruses, cells, and medium.

FHV-1 strain (C-27) was obtained from the American Type Culture Collection (ATCC VR 636 which is well known to those skilled in the art and is publicly available). Crandell Reese Feline Kidney (CRFK) cells were grown in Dulbecco's modified Eagle Medium, containing 10% heat-inactivated fetal bovine serum. The Crandell Reese Feline Kidney (CRFK) cells were infected with plaque-purified virions as described previously (Maes, R., et al., J. Virology 51:259–262 (1984)).

In-Vitro Labelling and Immunoprecipitation of FHV-1 Infected Cells

Radiolabelling and immunoprecipitation were performed as previously described (Maes, R., et al., J. Virology 51:259–262 (1984)). Briefly, cytoplasmic extracts were prepared in 1× PBS containing 1.0% Triton X-100, 0.5% sodium deoxycholate, and 0.1% SDS (PLB). Virion lysates were prepared from virions purified through 30% potassium tartrate cushions. Monospecific rabbit anti-HSV-1 gB sera (gB1 and R69) were obtained from Drs. N. Balachandran, Kansas State University and R. Eisenberg, University of Pennsylvania, respectively and are freely from these sources.

Western Blot Analyses

FHV-1 virions from infected CRFK cells were purified by rate zonal centrifugation through 10 to 40% potassium tartrate gradients (Talens, L. and Zee, Y., Proc. Soc. Exp. Biol. Med. 151: 132–135 (1976)). The resulting polypeptides were separated by SDS-PAGE. Immunoblotting was done according to procedures described by Ausubel et al., (Ausubel, F., et al., Current Protocols in Molecular Biology, John Wiley and Sons, New York (1988)), except that 5.0% low fat milk powder was substituted for the 3.0% BSA in all the washing solutions.

Recombinant DNA Methods

Recombinant plasmid containing the complete HSV-1 gB coding domain pST11 was kindly provided by Drs. Stanley Person (Pennsylvania State University) and are freely available upon request. The external coding domain of HSV-1 gB was excised from the plasmid pST11 as a NcoI-XhoI fragment, radiolabelled and used extensively as a probe in reduced-stringency hybridizations with blots containing cloned restriction fragments of FHV-1. Individual strip blots were hybridized at 45° C. in standard hybridization solution containing no formamide and washed under stringent conditions.

RNA Isolation and Northern Analyses

Total cellular RNA was extracted using the guanidinium isothiocyanate procedure (Ausubel et al., Current Protocols in Molecular Biology, John Wiley and Sons, New York (1988)). from mock infected or FHV-1 infected CRFK cells at a m.o.i. of >1.0 pfu/cell at 10 hours post-infection. Ten micrograms of RNA were electrophoresed in 1.2% formaldehyde gels, passively transferred to nitrocellulose and hybridized with radiolabeled probes.

DNA Isolation

Viral DNA was prepared as described previously (Rota, P., et al., Virology 154:168–179 (1986)). Plasmid DNA was isolated from bacteria by the alkaline lysis method (Sambrook, J., et al., Molecular Cloning: A Laboratory Manual. Vol. II Cold Spring Harbor, N.Y.: Cold Spring Harbor Laboratory (1989)). Single stranded DNA from M13 phage was isolated by pelleting the virions through a cushion containing 25% PEG in 3M NaCl. The pellets were then resuspended in TES buffer (20 mM Tris-HCl, pH 7.5, 20 mM NaCl, 1 mM EDTA) and lysed with equal volumes of water saturated phenol. The DNA was recovered after precipitation with sodium acetate and ethanol (Ausubel et al., 1988, cited above). Nucleic acid sequencing was performed by the dideoxy chain termination method (Sanger, F., et al., Proceedings of the National Academy of Science, U.S.A. 74, 5463–5467 (1977)) with the modified T7 DNA polymerase, Sequenase (US Biochemicals, Cleveland, Ohio) and with $^{35}$S dATP (New England Nuclear, Boston, Mass.) as the label. The analog deoxyinosine triphosphate (dITP) was often substituted for dGTP to minimize band compression. In most cases, single stranded M13 DNA was sequenced, but on occasion sodium hydroxide denatured double stranded Bluescript DNA was also used. Synthetic primers, along with the universal and reverse primers of M13 were used to rapidly generate sequencing data. The oligonucleotides used were synthesized on a 380B Applied Biosystems automated DNA synthesizer (Applied Biosystems, Foster City, Calif.) with a three column upgrade. Electrophoretically separated sequencing reaction products were visualized by autoradiography of dried 8% acrylamide/7 M urea gels using Kodak X-AR (Rochester, N.Y.) film. The sequences of both strands of viral DNA were determined at least twice from individual clones.

Computer Analyses of the DNA Sequence

DNA sequence management was performed on a VAX computer using versions 5.0 and 5.3 of the University of Wisconsin package (UWGCG, Madison, Wis.), (Deverex, J., et al., Nucleic Acids Research 12, 387–395 (1984)). Secondary structures of the predicted peptide were investigated using the methods of Chou and Fasman (Chou, P. and Fasman, G., Empirical predictions of protein conformation. Annual Review of Biochemistry 47: 251–275 (1978)). Graphic hydrophilicity analyses were generated by the method of Kyte and Doolittle (Kyte, J. and Doolittle, R., J. of Molecular Biology 157: 105–131 (1982)). Evolutionary relatedness of 12 alphaherpesviruses was analyzed using a multiple alignment of gB homologs generated by the LINEUP and PILEUP programs (UWGCG, Madison, Wis.). The TOFITCH program was used to make the infile for the Phylogeny Inference Package (PHYLIP), version 3.2 (Felsenstein, J., Evolution 39: 783–791 (1985)).

Results

Characterization of the FHV-1 gB protein

Initial evidence for a HSV-1 homolog of glycoprotein B consisted of detecting FHV-1 proteins by immunoprecipitation of lysates from infected cells and virion lysates with monospecific antisera to HSV-1 gB (anti-gB1 and R69). Immunoprecipitation of FHV-1 infected cells with either R69 or anti-gB1 sera indicated the presence of cross-reactive proteins with MW's of 120, 100, 64, 58, and 56 Kd. When virion lysates were immunoprecipitated with either antisera, two proteins of 64 and 58 Kd were detected. A third protein of 100 Kd was also detected on overexposed autoradiographs. It is noteworthy that the 100, 64 and 58 Kd proteins were immunoprecipitated exclusively from virion lysates while the 56 Kd protein was immunoprecipitated when infected cellular lysates were used.

Western blot analyses provided additional evidence that FHV-1 contains a gB homolog. FHV-1 proteins from KT-gradient purified virions were separated on denaturing gels and electroblotted onto nylon membranes. After incubation with either R69 or anti-gB1, three peptides with MW's of 100 (range 99–100), 64 (range 62–66) and 58 (range 60–57) Kd could be detected with $^{125}$I protein A.

Identification and sequence analysis of the FHV-1 gB gene

Figure 1B:
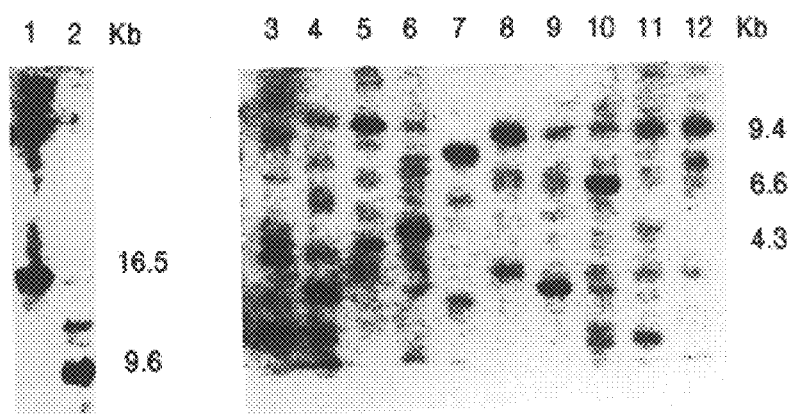

Evidence for a FHV-1 glycoprotein B gene initially came from southern analyses showing that a HSV-1 gB probe specific for the 5' end of the gene hybridized to an EMBL3/FHV-1 recombinant containing the 9.6 Kb SalI G fragment (FIG. 1). Southern analyses of FHV-1 DNA further localized the gene to a 3.3 Kb SacI subfragment of the larger SalI G clone. The nucleotide of this 3.3 Kb subfragment was then determined and analyzed for open reading frames containing amino acid stretches with similarity to gB homologs of other herpesviruses. These analyses (FIGS. 3A and 3B) revealed two overlapping open reading frames, coding for the glycoprotein B and ICP18.5 genes. An ORF of 2,829 nucleotides capable of encoding a gB translation product of 943 amino acids was identified and contained a TATA box (AATATATC), 148 nucleotides upstream of the initiation codon ATG. The sequence ATTG was also found approximately 113 base pairs 5' of the TATA box. This sequence may function as a CAAT box as speculated for HSV-1 gB and PRV gII (Hammerschmidt, W., et al., Virology 165: 406–418 (1988); and Robbins, A., et al., J. Virology 61: 2691–2701 (1987)). A potential Sp1 binding site, GGCGG was also found next to the CAT box (Gidoni, D., et al., Nature 12, 409–413 (1984)). Downstream of the ORF are two potential cis-acting elements. A polyadenylation signal, (AATAAA) was found 46 nucleotides downstream from the termination codon TAA and was followed by GT-rich sequences. Such GT-rich regions are similarly associated with many known RNA cleavage and polyadenylation sites (Birnstiel, M., et al., Cell 41: 349–358 (1985)).

An ORF encoding a polypeptide with homology to ICP18.5 of HSV-1 (UL28) was found to overlap the FHV-1 gB gene by 48 codons. A similar gene overlap has been reported for PRV, BHV-1, HVS, EHV-1, ILTV, EBV and EHV-4. ICP18.5 has been reported to be a nuclear protein and may be involved in capsid maturation (Pederson, N., et al., J. Virol. 65: 3746–3758 (1991); and Addison, C., et al., J. Gen. Virol. 71: 2377–2384 (1990)). Since no obvious polyadenylation signal was found 3' to the FHV-1 ICP18.5 ORF, the 3' terminus of this transcript may be coterminal with that of the gB mRNA.

Amino acid sequence and secondary structure of gB (FHV-1)

Figure 5:
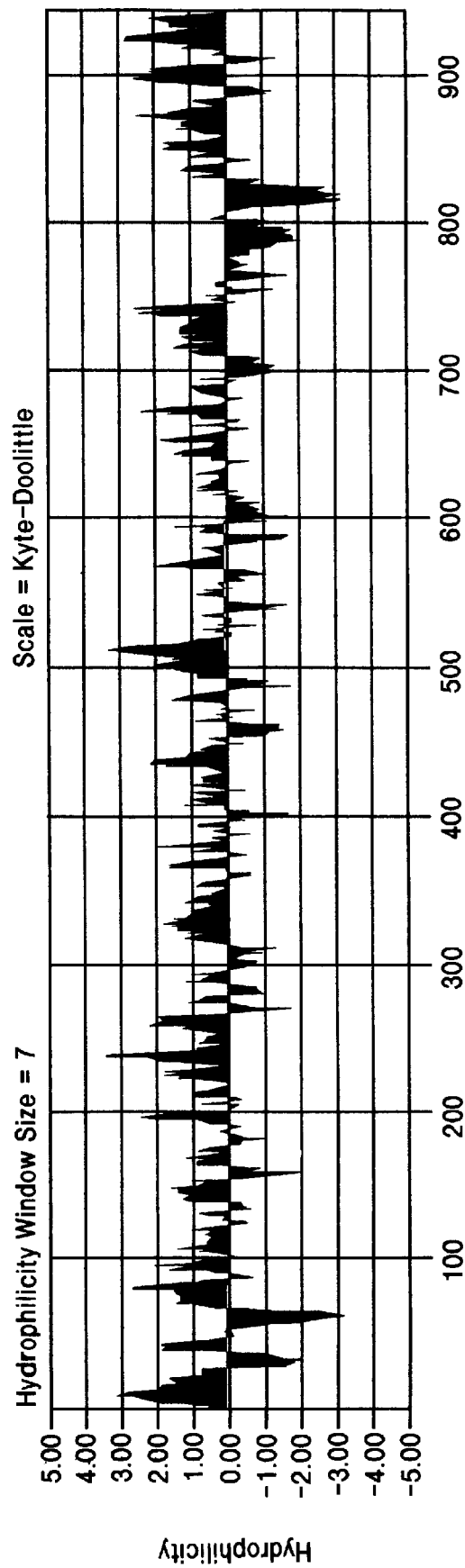

Hydrophilicity analyses of the 943 amino acid FHV-1 gB translation product indicated the presence of a hydrophilic surface domain at the amino terminus with 7 potential glycosylation sites. Two hydrophobic domains were also predicted at both ends of the polypeptide. A signal cleavage site (residues 58 to 66) consisting of 9 consecutive hydrophobic residues, FIWIVLFLV, followed by a helix-breaking residue glycine was found near the amino-terminus. This hydrophobic core was preceded by a region of positively charged arginine residues. Chou and Fasman analyses showed that the cleavage site is followed by a beta-turn (data not shown). Hydrophilicity plots (FIG. 5) also indicated a second hydrophobic domain (residues 758 to 827) located at the COOH-terminus). Three distinct hydrophobic peaks in this area fulfill the criteria for a transmembrane region. Three similar peaks have been reported in the corresponding regions of gB homologs of other herpesviruses. Based on Chou and Fasman analyses, this transmembrane domain was predicted to contain three antiparallel hydrophobic segments. Each segment, connected to the others by very short turn regions, transverses the membrane three times and provides the anchoring sequence for glycoprotein B.

A putative cytoplasmic domain (residues 828–911), characterized by a high hydrophilicity value, was predicted at the carboxyl-terminus and is typical of cytoplasmic regions of transmembrane glycoproteins.

Transcriptional analysis of the gB gene

Figure 2A:
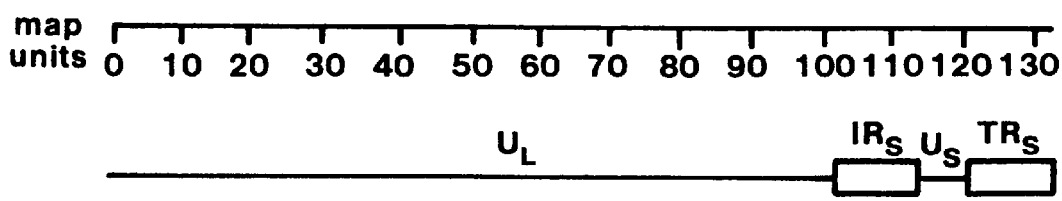
Figure 2B:
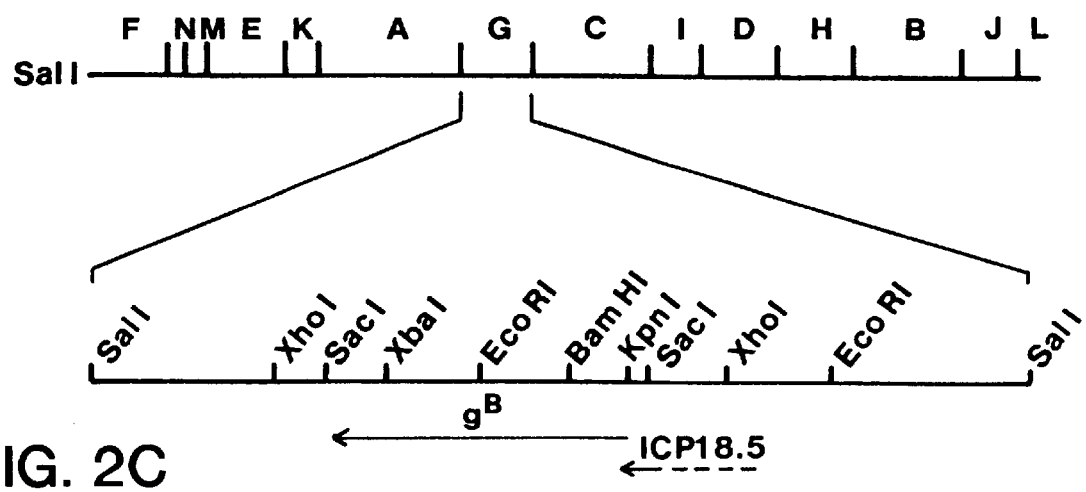
Figure 2C:
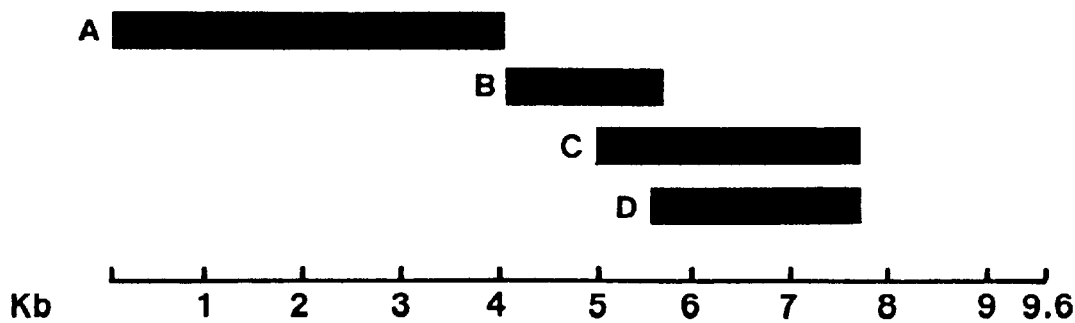
Figure 4A:
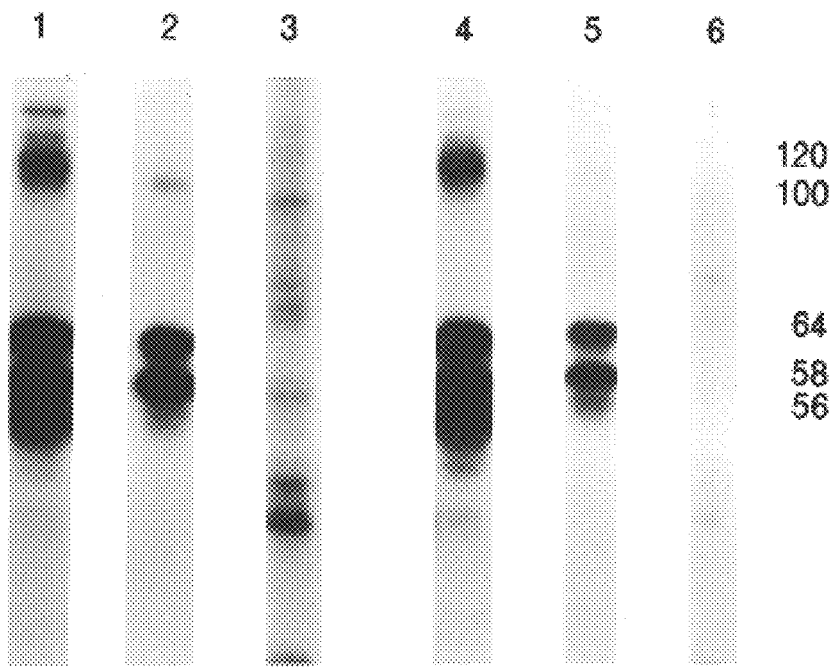
Figure 4B:
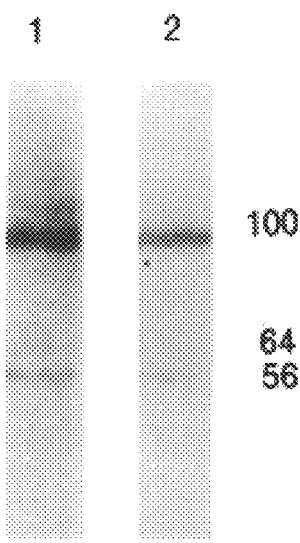
Figure 6:
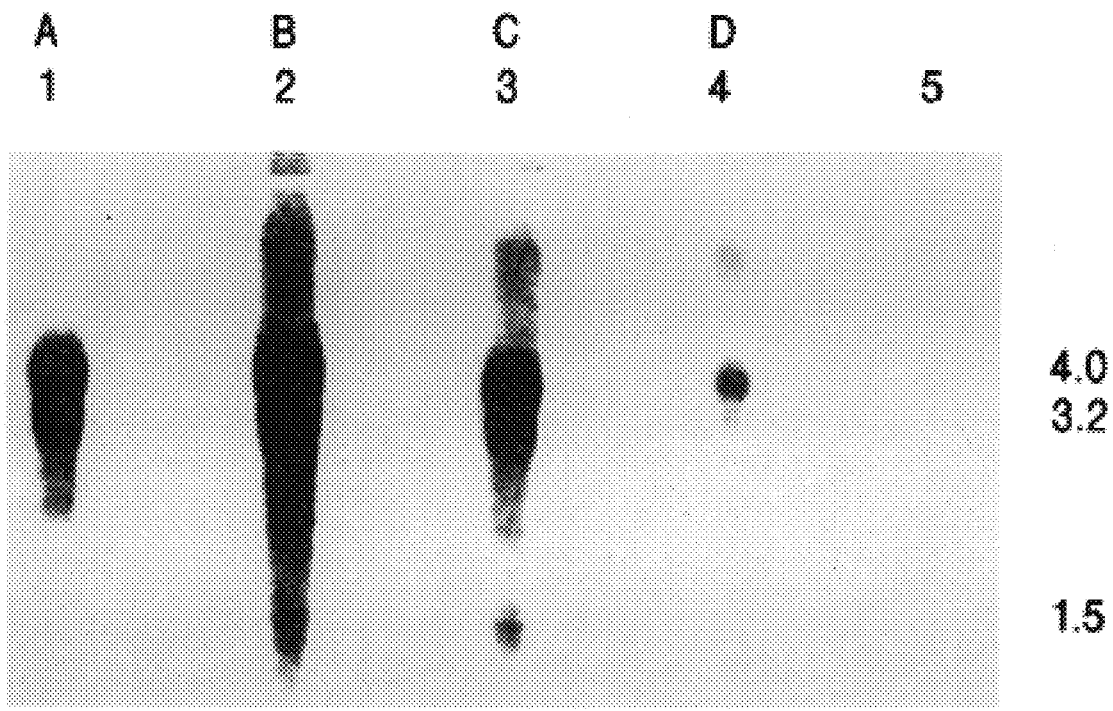
Figure 7:
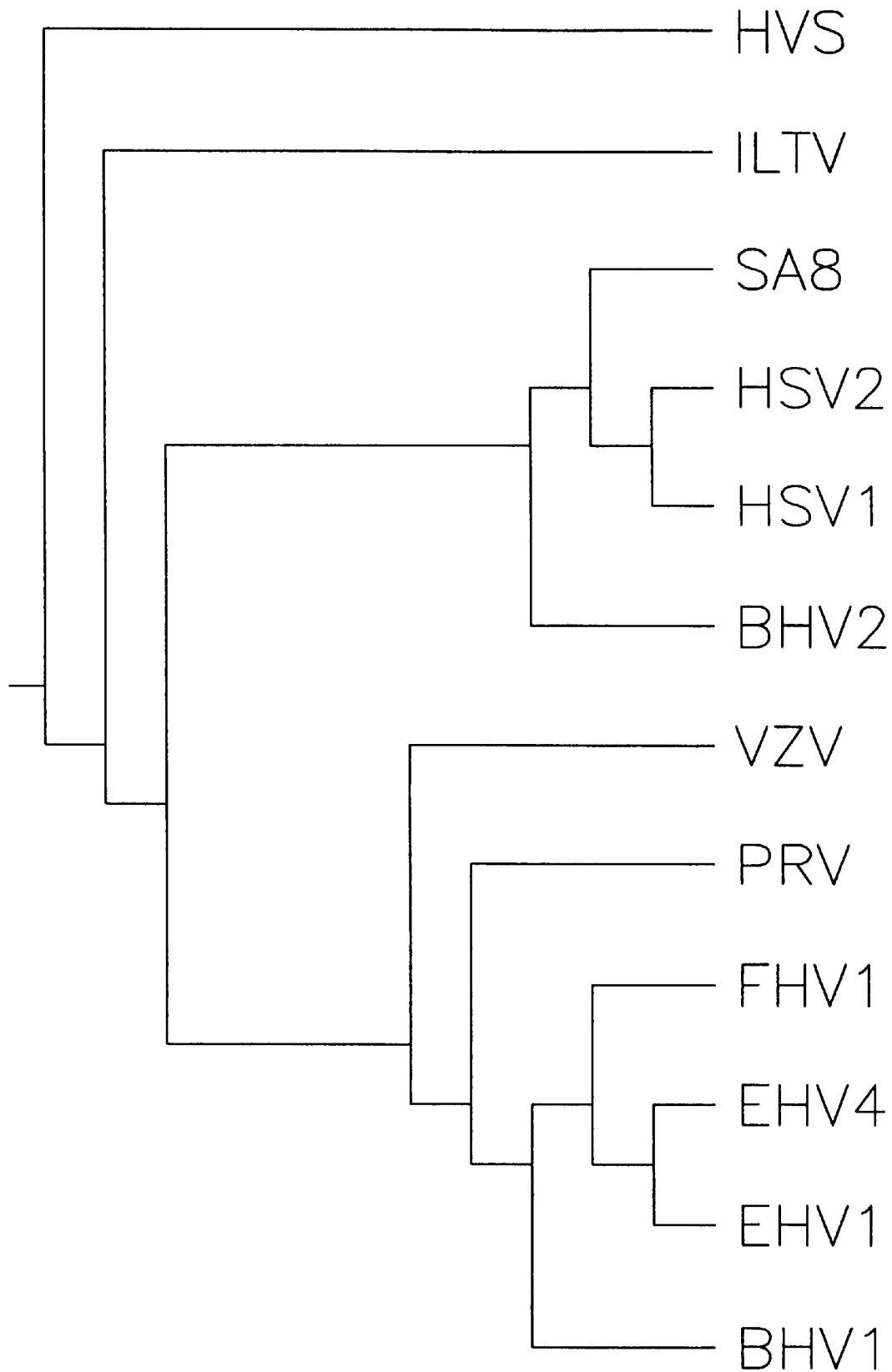
Figure 10:
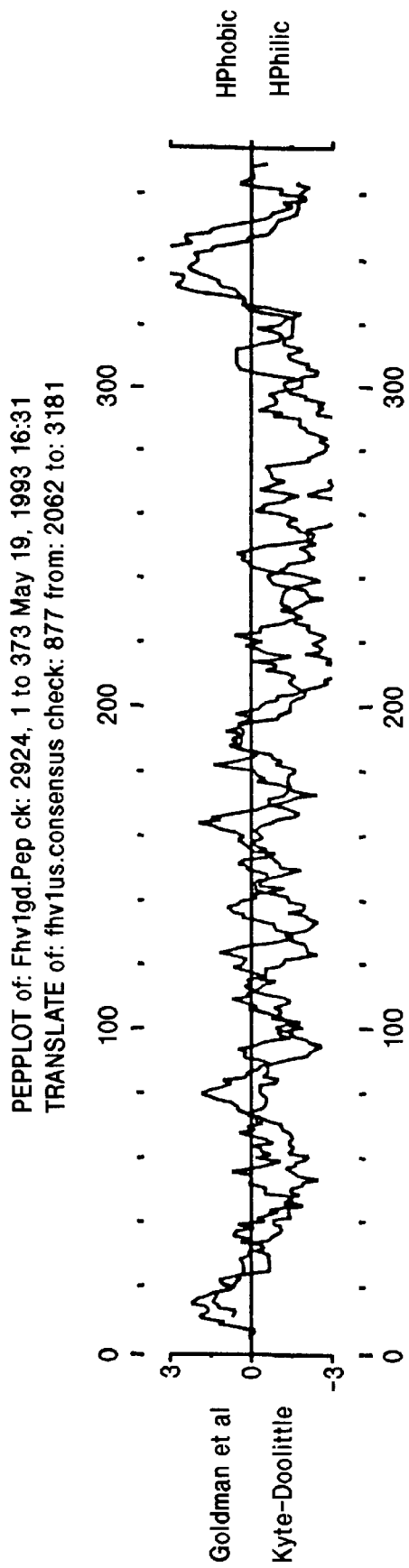

Northern blot analysis using four probes that span the entire FHV-1 gB gene (FIG. 2) has indicated the presence of 3 transcripts; 4.0, 3.2, and 1.5 Kb. As shown in FIG. 6, both the EcoRI-KpnI fragment (probe B) and the BamHI-EcoRI fragment (probe C) hybridized to the 4.0, 3.2 and 1.5 Kb transcripts, while the KpnI-EcoRI fragment (probe D) only hybridized to the 4.0 Kb transcript. These results indicate that the gB gene (3.2 Kb) is confined between the KpnI and SalI restriction sites and the transcription start site occurs between the KpnI and BamHI restriction sites. Thus the FHV-1 homolog of the HSV-1 gB gene was been identified using a 5' HSV-1 gB DNA probe in reduced-stringency hybridization experiments. The gene localized to a 3.3 Kb SacI subfragment of the larger SalI G fragment. Nucleotide sequencing of the SacI fragment has identified an open reading frame with characteristics typical of a glycoprotein gene. Based on the assumption that gB of FHV-1 contains 943 residues, cleavage of the signal peptide occurs after amino acid 69 and that 7 potential glycosylation sites are used, it is possible to calculate a MW of 114.5 Kd. If proteolytic cleavage occurs at amino acid 502, then two peptides with MW's of 60.5 and 54.0 Kd could result. If cleavage occurs at amino acid 513 then the two resulting peptides would have the MW's of 61.9 and 52.6 Kd. These numbers are in good agreement with the observed Mr values obtained by the immunoprecipitation and western blotting experiments.

EXAMPLE 2

In this example, the genomic location and the nucleotide sequence of the genes encoding a FHV-1 gD precursor polypeptide is described. To accomplish this, a 6.2 Kb portion of the $U_S$ region of the FHV-1 genome was determined. Analyses of this sequence has identified 5 open reading frames capable of encoding homologs to HSV-1 Pk, gG, gD, gI and gE. Homologs to these gene products have been found in a number of alphaherpesviruses (i.e. HSV-1, EHV-1, PRV, VZV, BHV-1 and MDV). Comparison at the amino acid level has indicated that the Us gene products of FHV-1 are most similar to those of EHV-1, except for glycoprotein D which shows more homology with gD of BHV-1. Hydropathic analyses of the predicted translation products has shown that FHV-1 glycoprotein D, I and E exhibit features typical of membrane-bound glycoprotein. Northern analyses of the FHV-1 Us genes have indicated the likelihood of numerous co-terminal transcripts.

Material and Methods

Viral and bacterial strains.

FHV-1 (strain C-27) was obtained from the American Type Culture Collection (ATCC VR 636 which is well known to those skilled in the art and is publicly available) and propagated in Crandell Reese Feline Kidney (CRFK) cells as described previously (Maes, R. K., et al., J. Virol. 51: 259–262 (1984)). Infectious cellular lysates were used as the source for viral DNA. *Escherichia coli* strain JM101 and JM109 available upon request from Michigan State University, E. Lansing, Mich., were grown in LB medium and used to propagate recombinant M13.

Cloning and DNA Sequencing This example includes the sequence for a portion of both strands of a 6,208 bp portion of the larger 14.5 Kb SalI B fragment (Rota, P., et al., Virology 154:168–179 (1986)). The 4.3 Kb EcoRI-EcoRI fragment and the adjacent 1.9 Kb EcoRI-SalI fragment located at the right terminus of the SalI B fragment were chosen for DNA sequence analysis. Hybridization analysis have indicated these two restriction fragments contain solely unique DNA.

For rapid generation of sequencing data, 4 individual M13 libraries were created using HAEIII, RSAI, TAQI and SAU3A restriction digestions of the 4.3 Kb EcoRI-EcoRI and 1.9 Kb EcoRI-SalI fragments. Single stranded DNA from recombinant M13 phage was isolated according to (Ausubel et al., Current protocols in molecular biology, John Wiley and Sons, New York, (1988)) and sequences using standard dideoxynucleotide chain termination reactions with the modified T7 polymerase, sequenase (US Biochemical, Cleveland, Ohio). $^{35}$S dATP (New England Nuclear, Boston, Mass.) was used as the label and dITP was used to resolve band compressions. Synthetic oligonucleotides, along with the Universal and 17'mer M13 primers were used to obtain sequencing information from both strands. Reaction products were electrophoretically separated and visualized by autoradiography of dried 8% acrylamide/7.0 M urea gels using Kodak X-AR (Rochester, N.Y.) film.

Analyses of Sequence Data

DNA sequences were compiled on a VAX computer using version 6.2 and 7.0 of the University of Wisconsin package UWGCG (UWGCG, Madison, Wis.). Hydrophilicity analysis of individual predicted translation products were generated by the method of (Kyte and Doolittle, J. of Molecular Biology 157:105–131, (1982)). Amino acid homology searches of the Swissprot (Release 18.0, 5/91) data bases were conducted using the FASTA program (UWGCG). The GAP, LINEUP, PILEUP programs were used to generate multiple alignments between FHV-1 Us predicted polypeptides and homologs found in related herpesviruses.

Results

Restriction map of the Unique Short Region of the FHV-1 Genome.

As shown in FIG. 8, the 14.5 Kb SalI B fragment contains 3 EcoRI restriction sites. A restriction map of the 4.3 Kb EcoRI-EcoRI and the 1.9 Kb EcoRI-SalI subfragments were constructed using EcoRI, XbaI, EcoRV, XhoI and SalI.

DNA Sequence analysis of 6.2 Kb of FHV-1 Us DNA

Sequence data obtained from the 6.2 Kb region of the SalI B fragment is presented in FIGS. 9A to 9E. Examination of the nucleotide sequence revealed the presence of 5 major open reading frames (ORF's). Open reading frame 3, capable of encoding a polypeptide of 373 amino acid residues, extends from nucleotide position 2062–3180 and encodes a precursor polypeptide to gD as shown in FIGS. 9A to 9E. Two potential initiation codons (CTAATGA and ATGATGA), next to each other can be used a start codons, although the later sequence has the critical purine at position −3. If this second initiation codon is used, then the expected polypeptide would be 373 amino acids long. A TATA-like element at position 1908 to 1912 is the only potential cis-acting promoter element. A stop codon TAA at position 3181–3183 is present, in the absence of any downstream polyadenylation signal. Hydropathy plots have indicated the presence of two hydrophobic sequences close to the amino and carboxyl termini. The first region FWWCGIFAVL (position 2077–2104) corresponds to the signal sequence and the second region VVIPAIVLSCLIIALILGVI near the carboxyl terminus could function as a membrane anchoring sequence. Four potential N-linked glycosylation sites are possible in the predicted translation product of ORF 3. An Mr of 46 Kd can be calculated, assuming cleavage of the nascent polypeptide occurs between $Ala_{13}$ and $Val_{14}$.

Comparison of the amino acid sequence of ORF 3 with proteins in the Swissprot data base has revealed extensive homology with gD analogs of other alphaherpesviruses. FASTA scores greater than 400 were achieved when these analyses include gD of bovine herpesvirus type 1, pseudorabies virus and equine herpesvirus type 1.

Analysis of transcripts encoding gD of FHV-1.

Figure 11:
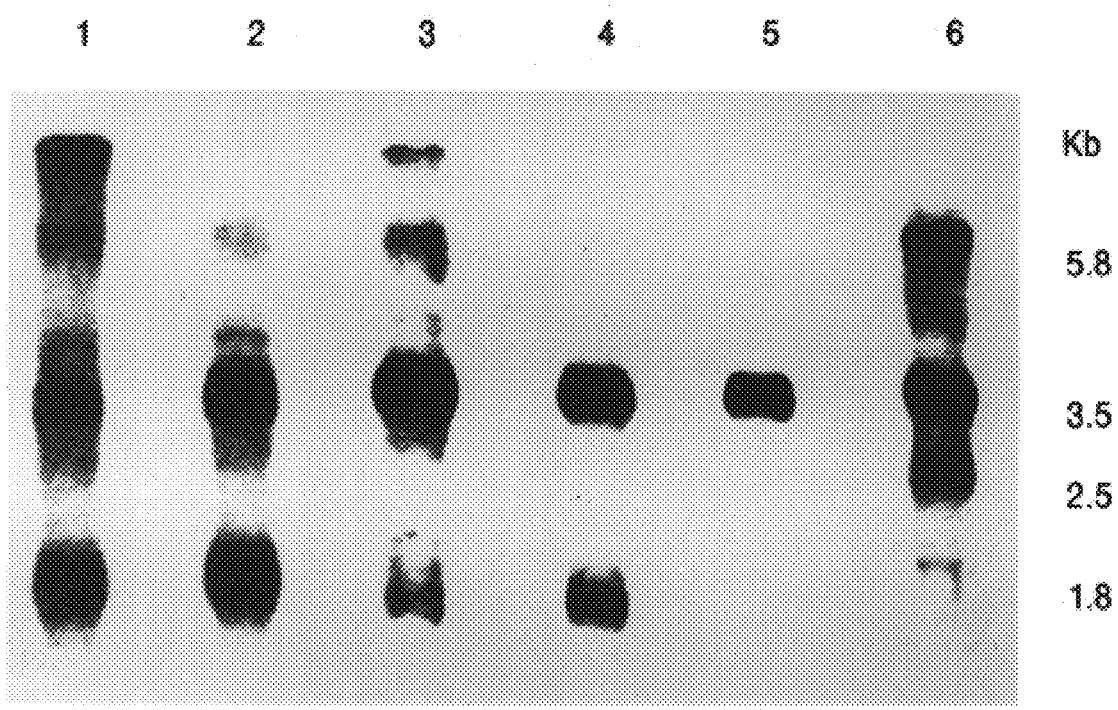
Figure 12A:
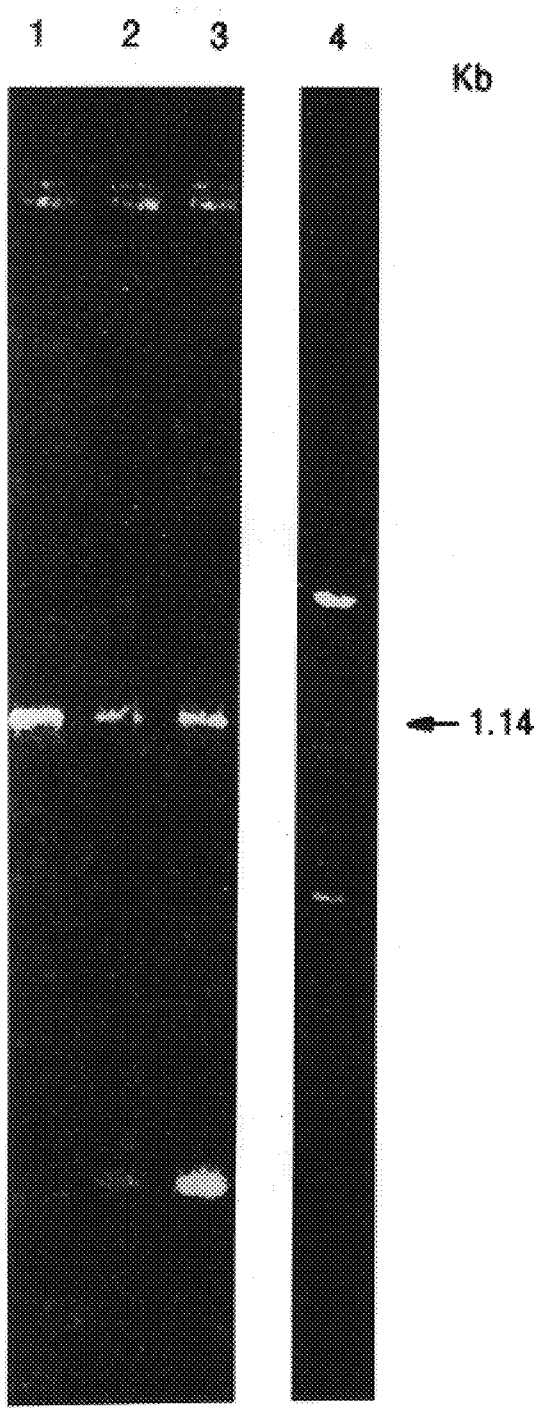
Figure 12B:
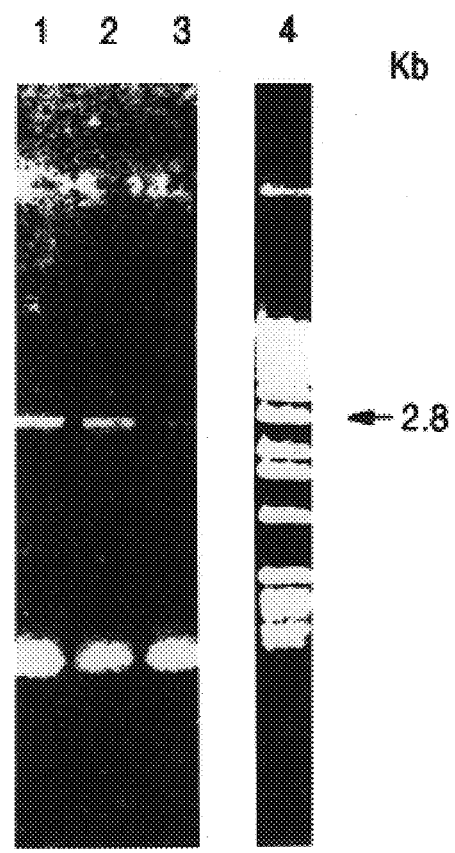
Figures 13A, 13B:
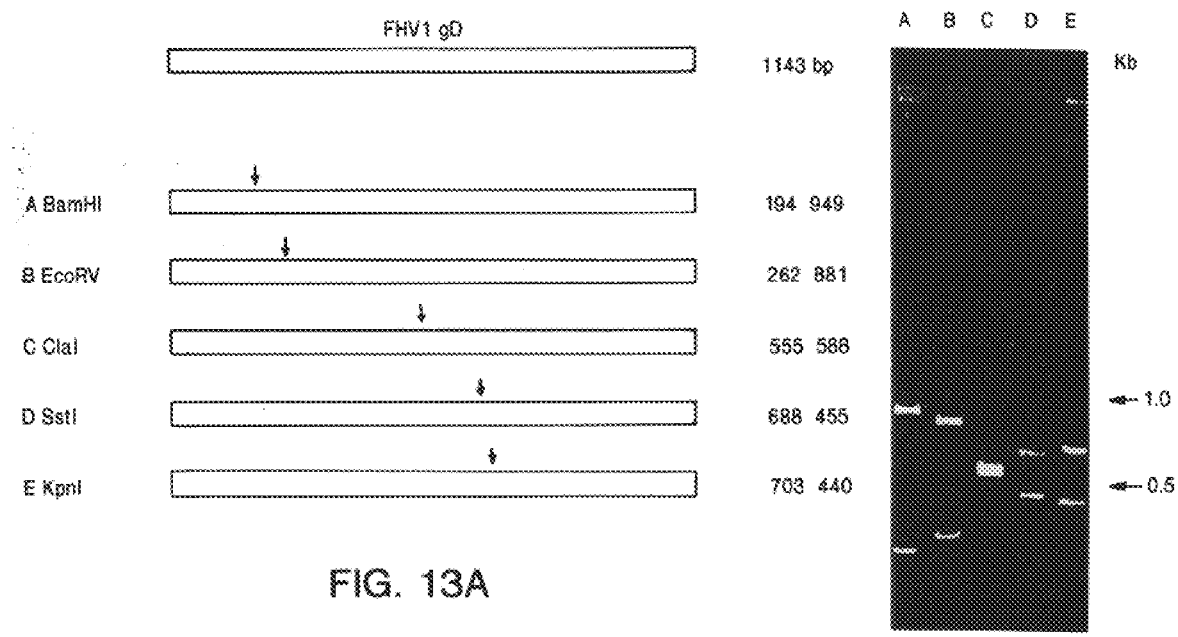
Figures 14A, 14B:
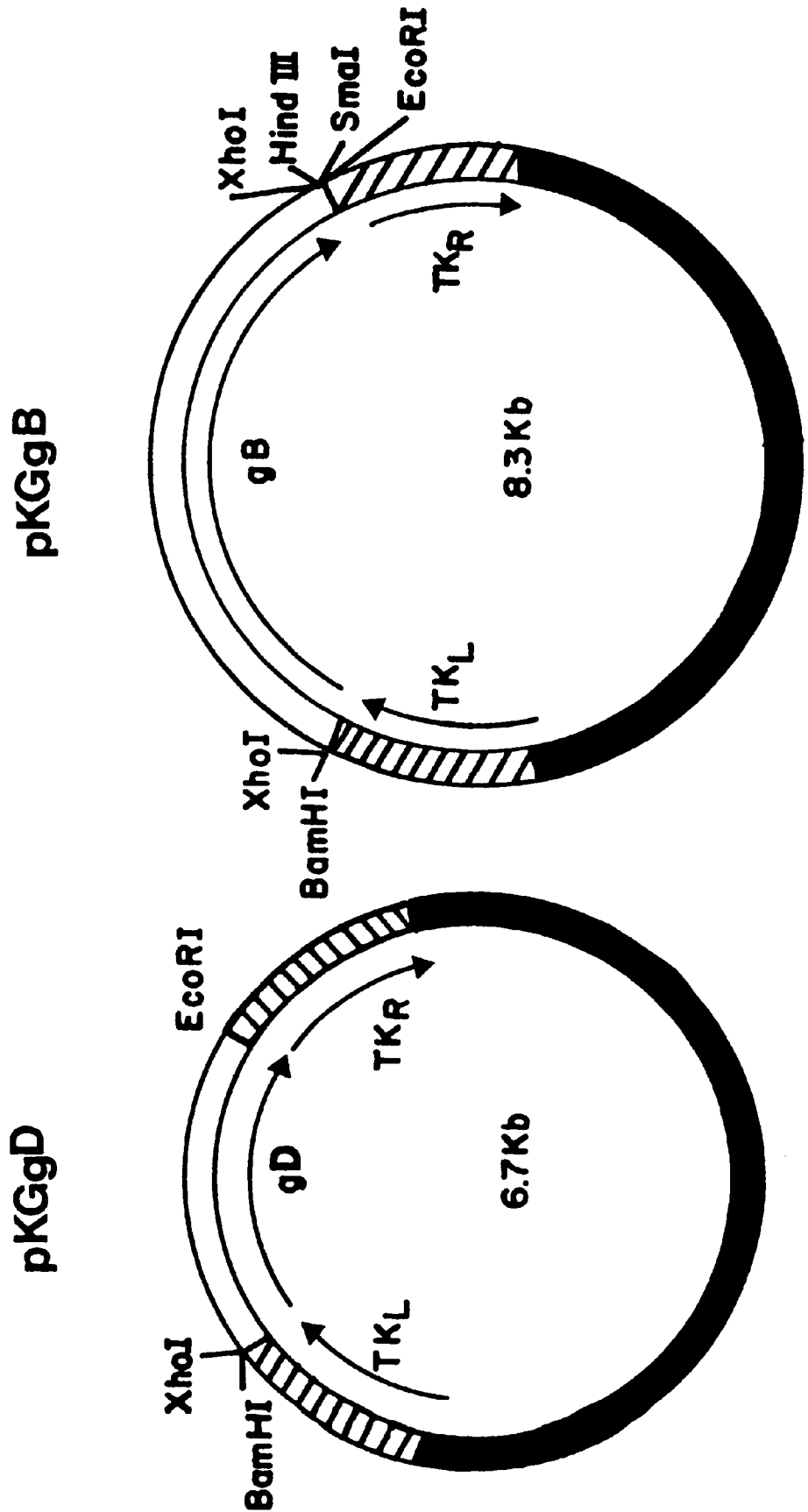
Figure 15:
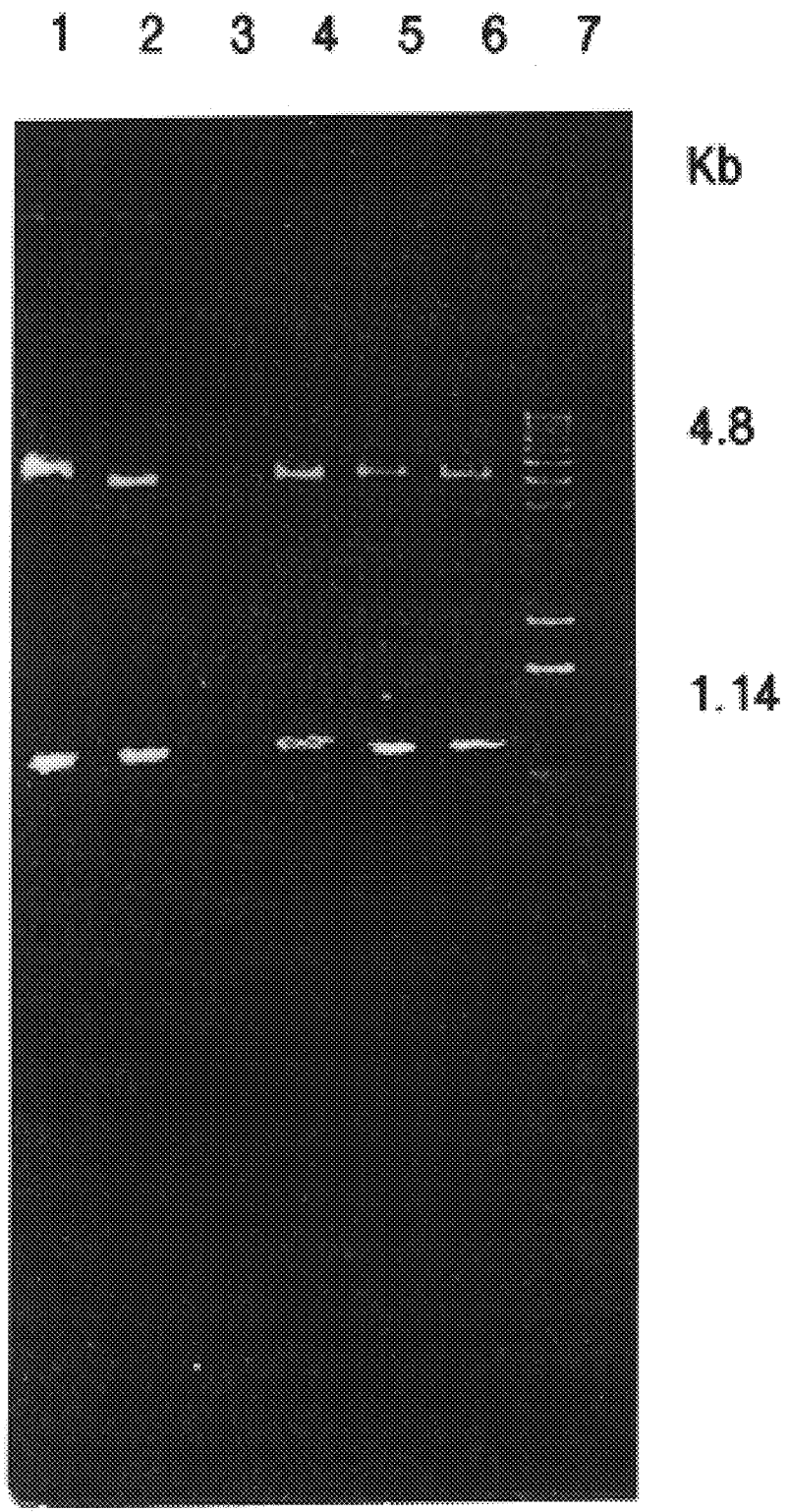
Figure 17A:
Figure 17B:
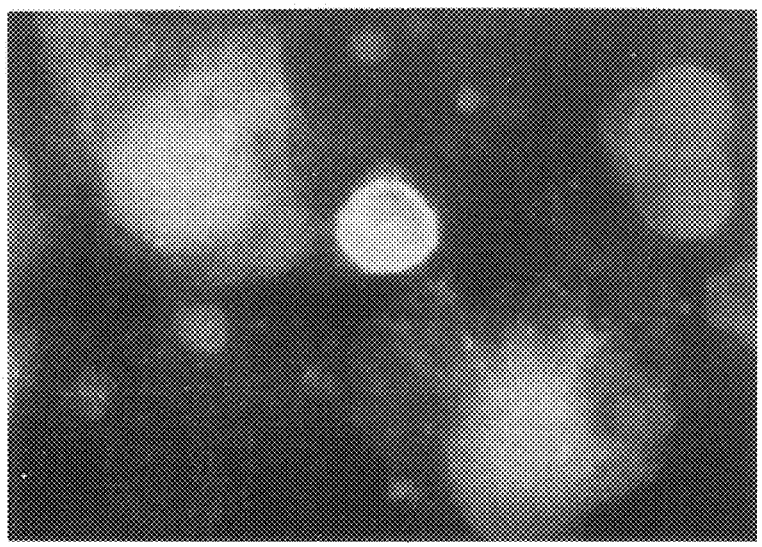
Figure 17C:
Figure 17D:
Figure 17E:
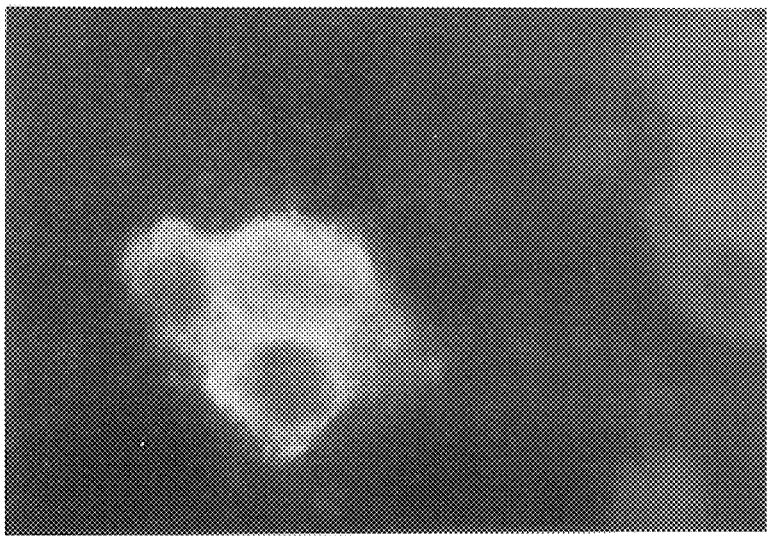
Figure 17F:

Northern analyses, using probes specific for the gD gene have indicated the likelihood of co-terminal transcripts. As shown in FIG. 11, two transcripts (3.5 and 1.8 Kb) were detected using the gD-specific probe. The 1.8 Kb transcript is thought to encode a monocistronic transcripts specifying gD. It is not known if this transcript is polyadenylated, since no polyadenlyation sites was found immediately 3' to the gD ORF. It is likely that the 3.5 Kb transcript terminates at the polyadenylation site located 3' to the downstream gene encoding glycoprotein I.

EXAMPLE 3

The aim of this example was to construct recombinant orthopoxviruses (i.e. raccoon poxviruses and vaccinia virus) expressing FHV-1 glycoproteins B and D. Selection of raccoon poxvirus as a vector was based upon a report that high titers of neutralizing antibodies were generated in cats infected with raccoon poxvirus. Furthermore, no adverse reactions were observed in the vaccinated cats (Scott, F., Raccoon poxvirus in the cat-candidate carrier virus for recombinant vaccines. In: the proceedings of the 69th conference of research workers in animal disease. Chicago, Ill. (1988)).

The FHV-1 gB/gD raccoon poxvirus recombinants are expected to be more immunogenic than MLV vaccines. In addition they should elicit better protection against reinfection and subsequent latency establishment. Poxvirus recombinants will also offer additional savings in storage and shipment costs of FVR vaccine, due to the higher stability of these recombinants over MLV vaccines.

Material and Methods

Cells and Viruses.

Crandell Reese Feline Kidney (CRFK) were cultured in Eagle minimum essential medium (MEM) supplemented with 10% fetal bovine serum (FBS) and used to propagate FHV-1, strain C-27. Rat-2 and human 143B cells, both thymidine kinase negative (TK-), were grown in the same medium. Vaccinia virus strain WR, raccoon poxvirus and recombinant viruses derived from both were propagated on Rat-2 cells in the presence of 25 ug/ml of 5-bromo-2'deoxyuridine (BUdR).

PCR-amplification and Plasmid Construction

The complete coding sequences of FHV-1 glycoproteins B and D were amplified using flanking oligonucleotides specific for the 5' and 3' ends of each gene. Oligonucleotides were synthesized using a 380B Applied biosystems DNA synthesizer (Applied Biosystems, Foster City, Calif.).

The gene encoding glycoprotein B was amplified using two oligonucleotides, 5' TAC CTC GAG TCA TGT CCA CTC GTG GCG ATC 3' and 5' GGT CTC GAG GGT TAG ACA AGA TTT G 3'. Each primer contained an XhoI recognition sequence which facilitated the cloning of the amplified 2.8 Kb product. The template (100 ng) was boiled for 2 minutes and 50 pmoles of each primer was allowed to anneal. The conditions for 37 cycles of amplification were as follows: 2 minutes at 53° C., 5 minutes at 72° C. and 1 minute at 95° C. One unit of pfu polymerase (Stratagene, La Jolla, Calif.) was used in the standard buffer.

To amplify the gene encoding gD of FHV-1, two gD-specific oligonucleotides, 5' CAT CTC GAG TAA TGA TGA CAC GTC TAC A 3' and 5' TGT GAA TTC AAG GAT GGT GAG TTG TA 3' were used. The latter oligonucleotide contained an XhoI recognition site, the former contained an EcoRI recognition site. Incorporation of these two restriction sites into the amplified PCR-product facilitated directional cloning. The buffer was identical to the one previously mentioned, while the PCR conditions differed slightly; 1 minute at 60° C., 2 minutes at 72° C. and 1 minute at 95° C. for 37 cycles with one unit of pfu polymerase (Stratagene, La Jolla, Calif.).

Both gB and gD PCR-amplified products were digested with the appropriate restriction endonucleases (XhoI for the gB gene and XhoI/EcoRI for the gD gene) and separately cloned into pKG19 (obtained from Dr. Paul Rota of the Centers for Disease Control in Atlanta, Ga. and freely available from this source).

Transfections and Selection

Recombinant plasmid DNA was purified using alkaline lysis (Ausubel et al., Current Protocols in Molecular Biology, John Wiley and Sons, New York, (1988)). Plasmid DNA was then used to transfect human 143 Tk-cells using the lipofectin method (BRL, Gaithersburg, Md.). One hour prior to transfection the cells, grown to 75% confluency in 35 mM plates, were infected with either vaccinia or raccoon poxvirus using a m.o.i. of <1.0. Lipid/DNA complexes were created by mixing 25 ul of $H_2O$, 25 ul of lipofectin (approx. 30 ug) and 50 ul of recombinant plasmid containing 20 ug. This mixture was incubated for 15 minutes at room temperature before addition to the infected cells. After absorption, transfected cells were pelleted using low-speed centrifugation and resuspended in 1.0 ml of Mandel's solution. Ten-fold serial dilutions of the viral supernatants were made and Rat 2 cells were infected for 1 hour at 37 C. Following this, 3.0 ml of 1% LMP agarose (45° C.) containing 1× MEM and 25 ug/ml BUdR was overlayed on the cells. After an incubation at 37° C. for 48 hours, 3.0 ml of neutral red was added and the cells were stained for <3.0 hours. Visible plaques were picked and resuspended in 500 ul of 1× Mandel's solution.

Detection of expressed glycoproteins

Indirect immunofluorescent antibody tests were carried out on transfected cells which were previously infected with either raccoon poxvirus or vaccinia virus. These cells designed to express either gB or gD in both raccoon poxvirus or vaccinia virus were cytocentrifuged onto glass slides. Cells were fixed with cold absolute methanol for 15 minutes and then blocked with 5% low-fat milk powder in 1× PBS for 1 hour. Expression of either FHV-1 gB or gD in these cells was assessed by the indirect fluorescent antibody test, using a rabbit hyperimmune serum against FHV-1 as the primary antibody and fluorescein labeled goat anti-rabbit serum as the reporter antibody.

Testing of the vaccinia poxvirus recombinants in rabbits

Experimental rabbits were inoculated intradermally with recombinant vaccinia poxviruses expressing either FHV-1 gB or FHV-1 gD. One month post-inoculation a blood sample was collected and the serum tested for the presence of virus neutralizing antibodies to FHV-1. A microtiter virus neutralization test was used for this purpose.

Western Blot Analyses

FHV-1 virions from infected CRFK cells were purified by rate zonal centrifugation through 10–40% potassium tartrate gradients (Talens, L. and Zee, Y., Proc. Soc. Exp. Biol. Med. 151: 132–135 (1976)). Purified virions were resuspended in 1× PBS and separated by SDS-PAGE. Immunoblotting was done according to procedures described by (Ausubel et al., Current Protocols in Molecular Biology, John Wiley and Sons, New York (1988)), using 5.0% low fat milk powder as a blocking agent. Alkaline phosphatase-labelled anti-rabbit conjugates along with the chromogens BCIP and NBT, were used to visualize the bands.

Virus Neutralization Assay

Antisera, each specific for the vaccinia recombinants (VVgB and VVgD), were assayed for the presence of virus-neutralizing antibodies by a microneutralization assay. Briefly, heat inactivated (56 C, 30') sera were used to make a two-fold dilution series. Approximately 100 $TCID_{50}$ of FHV-1 (C-27) was added to each dilution. The virus-serum mixtures were incubated for 1 hour at 37 C. CRFK cells (15,000) were added to each well and the plates were incubated at 37 C in an atmosphere of 5% $CO_2$ in air. The VN titers were expressed as the reciprocal of the highest serum dilution resulting in complete inhibition in CPE.

Results

Construction of recombinants vaccinia and raccoon poxviruses expressing glycoprotein B and D of FHV-1

The genomic locations of the genes encoding glycoproteins B and D of FHV-1 are illustrated in FIGS. 2 and 8. The gene encoding FHV-1 gB is located within a 3.3 Kb SacI subfragment of the larger SalI G. The SalI B (14.5 Kb) fragment from the unique short region encodes glycoprotein D. The gene is confined to a 1.5 Kb HincII-XhoI subfragment. These subfragments were purified and used as the templates for the amplification of both genes. Amplification of the gB and gD genes resulted in a 2.8 and 1.1 Kb PCR-product, respectively (FIG. 12). Restriction analyses of the gD PCR-product is presented in FIG. 13. Both amplified products were cloned into the vaccinia-thymidine kinase donor plasmid (pKG19) as depicted in FIG. 14. Restriction endonuclease analysis (FIGS. 15 and 16A to 16D) of the recombinants (pKGgD and pKGgB), respectively, verified the authenticity of the cloned gD gene (pKGgD) and indicated the two possible orientation of the cloned gB product.

Recombinant donor plasmids were transfected into vaccinia or raccoon poxvirus infected Human 143B Tk-cells. The number of BUdR resistant recombinants obtained was higher for vaccinia than the slower growing raccoon poxvirus. Actually, due to the slow growth of recombinants in the human cells and the fact that plaquing morphology was difficult to determine, RPV-recombinants were plaqued on Rat-2 Tk-cells. The Rat-2 cells formed a more single monolayer of cells, as compared to the human 143B cells, and RPV formed plaques in these cells within 4–5 days.

Expression of glycoproteins B and D in transfected Rat-2 cells

Transfected cells were analyzed for the expression of FHV-1 gB and gD using a indirect fluorescent antibody assay. As shown in FIG. 17, cytoplasmic staining was observed only in transfected cells previously infected with either vaccinia or raccoon poxviruses. Fluorescence was not observed in the controls. Cells infected with wild type vaccinia and raccoon poxvirus served as one form of negative control. The other control consisted of cells transfected with vaccinia or raccoon poxvirus donor plasmids containing an inverted gB genes with respect to the vaccinia 7.5 promoter.

Figure 18:
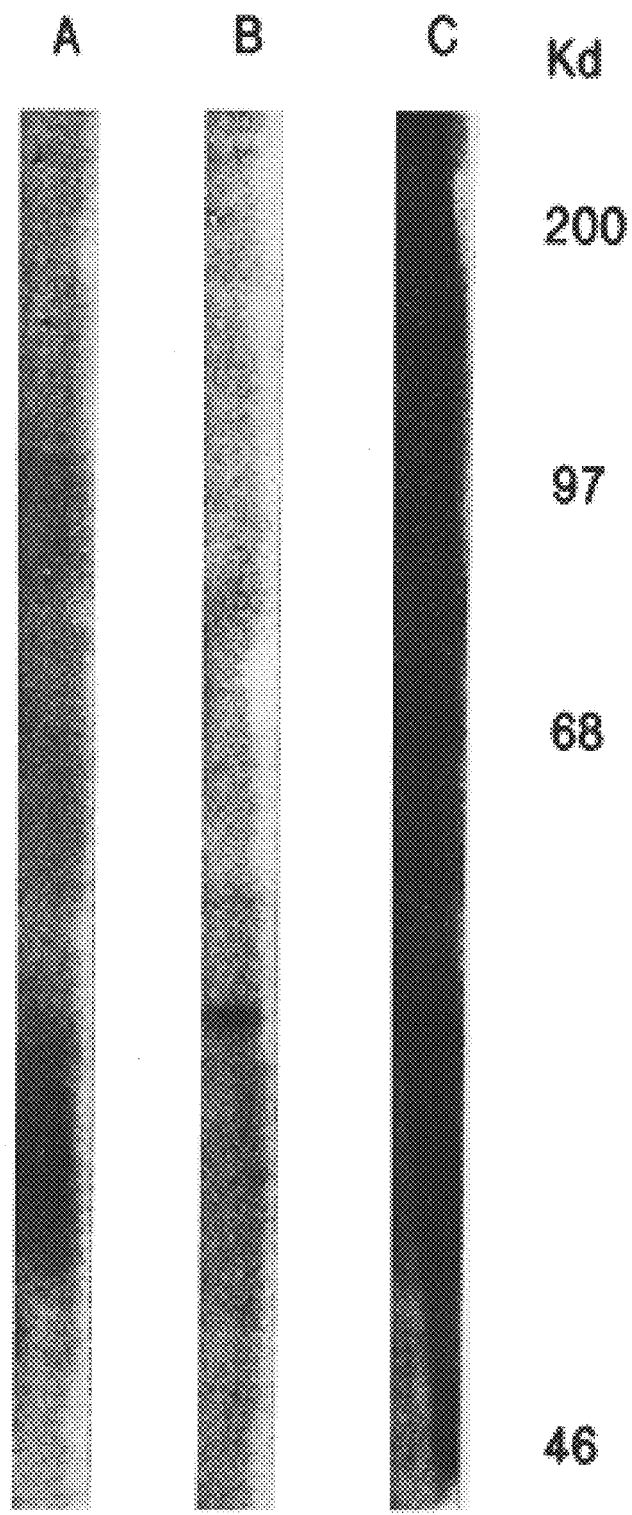

Western blot analyses (FIG. 18) were done with rabbit antisera against VVgB and VVgD and potassium tartrate-purified FHV-1 virions. Major immunodominant bands of 60 Kd (cleaved form of gB) and 50 Kd (gD) were detected at a 1/400 dilution of the polyclonal sera. FHV-1 proteins did not react with an antiserum specific for WT-vaccinia virus (Data not shown). Rabbits immunized with VVgB or VVgD had VN titers of 64 and 1024, respectively in a microneutralization assay.

EXAMPLE 4

Testing of the raccoon poxvirus recombinants in experimental cats

A group of 12 Specific Pathogen Free (SPF) cats are purchased from a commercial supplier. The experimental cats are housed in approved ULAR facilities and cared for by licensed ULAR personnel. Sera are collected from all cats at the onset of the experiment. Five cats are inoculated with the raccoon pox recombinant expressing FHV-1 gB (Room 1). A second group of 5 cats receive the raccoon pox recombinant gD (Room 2) and a third group of 2 cats are used as challenge controls. One month after vaccination all cats are bled and tested for the presence of virus neutralizing antibodies to FHV-1. The vaccinated cats and the controls are then exposed to a dose of virulent virus known to induce clinical signs of rhinotracheitis in the control cats. Nasal, conjunctival and oral swabs are collected from all the cats at 3-day intervals. The swabs are extracted and tested for the presence of FHV-1 by inoculation of a feline cell line (CRFK). Both raccoon poxvirus recombinants (RPVgB and RPVgD) induce virus neutralizing antibodies in experimental cats. The antibodies can be induced in cats, since rabbits are not susceptible to raccoon poxvirus. Both raccoon pox recombinants expressing FHV-1 gB or FHV-1 gD can both induce protection against clinical signs of the disease. The recombinant expressing gD can be more efficient than the gB recombinant in this respect. The minimum dose needed for protection is between about $10^3$ and $10^7$ PFU (Plaque Forming Units) per dosage. The gD and gB recombinants could act synergistically in inducing protection against clinical signs and shedding of the virulent challenge virus. Induced immune response to either FHV-1 gD or gB can be checked by immunoprecipitation of $^{14}C$-Glucosamine labelled FHV-1 with antisera from vaccinates (Maes, R., et al., J. of Virology 51: 259–262 (1984)).

It is intended that the foregoing description be only illustrative of the present invention and that the present invention be limited only by the hereinafter appended claims.

We claim:

1. A recombinant raccoon poxvirus containing and expressing a first gene encoding the feline herpesvirus gD glycoprotein precursor polypeptide as set forth in SEQ ID NO: 9 wherein the first gene is inserted into a second gene encoding thymidine kinase of the raccoon poxvirus.

2. A recombinant raccoon poxvirus containing and expressing a first gene encoding a gD glycoprotein precursor polypeptide from a feline herpesvirus, said gene containing nucleic acid sequence SEQ ID NO:2 wherein the first gene is inserted into a second gene encoding thymidine kinase of the raccoon poxvirus.

3. The recombinant raccoon poxvirus of any one of claims 1 or 2 with a gene encoding a gB precursor peptide as set forth in SEQ ID NO:4 is inserted into the second gene in addition to the gene encoding gD.

4. A vaccine which comprises:
a recombinant raccoon poxvirus containing and expressing a first gene encoding the feline herpesvirus gD glycoprotein precursor polypeptide as set forth in SEQ ID NO: 9 wherein the first gene is inserted into a second gene encoding thymidine kinase of the raccoon poxvirus.

5. The vaccine of claim 4 containing between about $10^3$ and $10^7$ PFU (Plaque Forming Units) of the recombinant poxvirus per dosage.

6. A vaccine which comprises a recombinant raccoon poxvirus containing a first genes from a feline herpesvirus encoding a gD glycoprotein precursor polypeptide and having the nucleic acid sequence as set forth in SEQ ID NO:2 wherein the first gene is inserted into a second gene encoding thymidine kinase of the raccoon poxvirus, which polypeptide is expressed by the poxvirus.

7. The vaccine of claim 6 containing between about $10^3$ and $10^7$ PFU (Plaque Forming Units) of the recombinant poxvirus per dosage.

8. The vaccine of any one of claims 4 or 6 with a gene encoding a gB precursor peptide as set forth in SEQ ID NO:4 is inserted into the second gene in addition to the gene encoding gD.

9. A method for inhibiting feline viral rhinotracheitis (FVR) in felines which comprises: vaccinating the feline with a recombinant raccoon poxvirus containing and expressing a gene encoding the feline herpesvirus gD glycoprotein precursor polypeptide as set forth in SEQ ID NO: 9 wherein the first gene is inserted into a second gene encoding thymidine kinase of the raccoon poxvirus.

10. The method of claim 9 wherein poxvirus is a live vaccine.

11. The method of claim 10 wherein the vaccine contains $10^3$ to $10^7$ PFU (Plaque Forming Units) of the poxvirus per dosage.

12. A method for inhibiting feline viral rhinotracheitis (FVR) in felines which comprises:

vaccinating the feline with a feline raccoon poxvirus containing a first gene encoding a gD glycoprotein precursor polypeptide and having the nucleic acid sequence as set forth in SEQ ID NO:2 which is expressed by the poxvirus to vaccinate against FVR, wherein the first gene is inserted into a second gene encoding thymidine kinase of the raccoon poxvirus.

13. The method of claim 12 wherein the poxvirus is a live vaccine.

14. The method of claim 13 wherein the vaccine contains $10^3$ to $10^7$ PFU (Plaque Forming Units) of the poxvirus per dosage.

15. The method of any one of claims 9 or 12 with a gene encoding a gB precursor peptide as set forth in SEQ ID NO:4 is inserted into the second gene in addition to the gene encoding gD.

* * * * *